(12) United States Patent
Genova et al.

(10) Patent No.: US 10,881,477 B1
(45) Date of Patent: Jan. 5, 2021

(54) STERILE BARRIER SYSTEMS FOR ROBOTIC SURGERY SYSTEMS

(71) Applicant: Titan Medical Inc., Toronto (CA)

(72) Inventors: Perry A. Genova, Chapel Hill, NC (US); Chad Clayton Walters, Apex, NC (US); Michael Edward Laut, Raleigh, NC (US); Steven Wayne Bockmann, Raleigh, NC (US)

(73) Assignee: Titan Medical Inc., Toronto (CA)

( * ) Notice: Subject to any disclaimer, the term of this patent is extended or adjusted under 35 U.S.C. 154(b) by 0 days.

(21) Appl. No.: 16/453,910

(22) Filed: Jun. 26, 2019

(51) Int. Cl.
*A61B 46/10* (2016.01)
*A61B 34/30* (2016.01)
*A61B 46/00* (2016.01)
*A61B 1/04* (2006.01)

(52) U.S. Cl.
CPC .............. *A61B 46/10* (2016.02); *A61B 34/30* (2016.02); *A61B 46/40* (2016.02); *A61B 1/04* (2013.01); *A61B 2034/301* (2016.02)

(58) Field of Classification Search
CPC combination set(s) only.
See application file for complete search history.

(56) References Cited

U.S. PATENT DOCUMENTS

| | | | |
|---|---|---|---|
| 5,591,119 A | 1/1997 | Adair | |
| 7,727,244 B2 | 6/2010 | Orban, III et al. | |
| 7,947,050 B2 | 5/2011 | Lee et al. | |
| 8,273,076 B2 | 9/2012 | Devengenzo et al. | |
| 10,278,683 B2 | 5/2019 | Robert | |
| 2002/0032451 A1* | 3/2002 | Tierney | G06Q 30/02 606/130 |
| 2006/0139753 A1 | 6/2006 | Moses | |
| 2006/0161137 A1* | 7/2006 | Orban, III | A61B 34/71 606/1 |
| 2011/0168189 A1 | 7/2011 | Cooper | |

(Continued)

FOREIGN PATENT DOCUMENTS

| | | |
|---|---|---|
| DE | 102015224986 A1 | 4/2017 |
| KR | 101105280 B1 | 1/2012 |
| WO | WO 2018013309 A1 | 1/2018 |

OTHER PUBLICATIONS

Priula S.R.L., "Medical packaging: Medical PE bags, poly bags for medical devices," downloaded Mar. 31, 2019 from www.priula.com/en/medical.html; 3 pages.

*Primary Examiner* — Scott Luan
(74) *Attorney, Agent, or Firm* — Knobbe, Martens, Olson & Bear LLP

(57) ABSTRACT

A sterile barrier system for a robotic surgery apparatus can include a drape coupler. The drape coupler can include an external surface configured to face a first surface of a first portion of the robotic surgery apparatus. The drape coupler can include at least one drape coupler fastener positioned at least partially on the external surface and configured to removably attach the drape coupler to the first surface. The drape coupler can be configured to at least partially cover the first surface. The system can include a drape made of a flexible material and coupled to the drape coupler, the drape configured to wrap around a second surface of the first portion of the robotic surgery apparatus, the second surface different from the first surface. The drape coupler and the drape can be sterile.

25 Claims, 48 Drawing Sheets

(56) References Cited

U.S. PATENT DOCUMENTS

2011/0277776 A1* 11/2011 McGrogan ......... A61B 17/3423
                                                                128/852
2016/0166348 A1    6/2016  Adams
2017/0086934 A1*  3/2017  Devengenzo .......... A61B 46/23
2019/0099232 A1*  4/2019  Soto ...................... A61B 46/10

* cited by examiner

Front

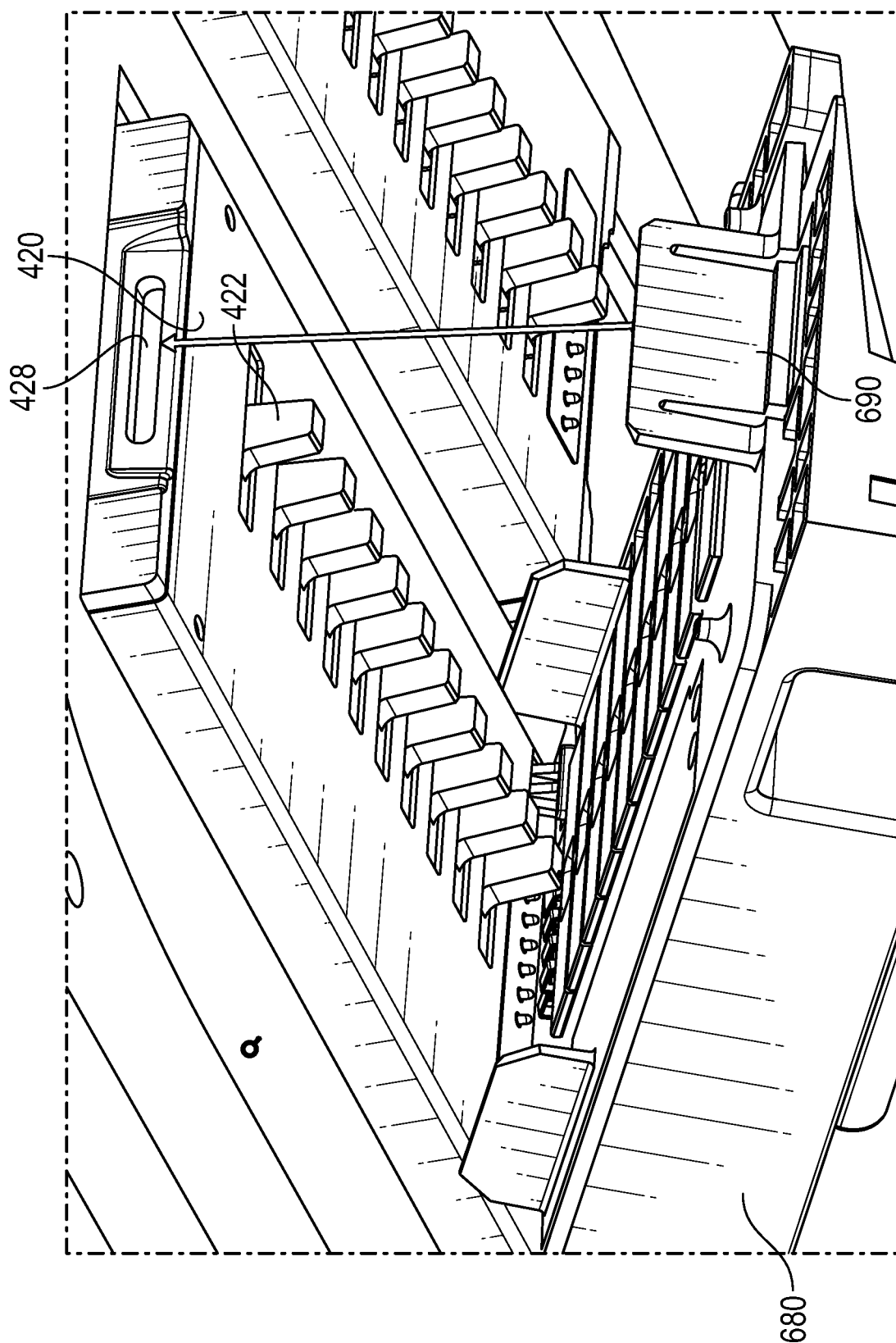

STERILE BARRIER SYSTEMS FOR ROBOTIC SURGERY SYSTEMS

TECHNICAL FIELD

This disclosure relates generally to robotic surgery systems and more particularly to sterile barrier systems and methods for such systems.

DESCRIPTION OF RELATED ART

Preventing surgical site infection in the operating room is one of the most important goals of a surgical team. Typically, the surgical team accomplishes this goal by creating and maintaining a sterile field, which can include environmental cleaning, disinfection, and sterilization of instruments. Creation and maintenance of the sterile field can impose the requirement that all items used within a sterile field remain sterile. When a robotic surgery system is used in the operating room, creation and maintenance of sterile field can present a number of challenges that have not been resolved by existing approaches. For example, due to the size and complexity, it may not be possible to sterilize the entire robotic surgery system. In many cases, partial sterilization may not be feasible or effective. The present disclosure overcomes these and other problems associated with known approaches for creating and maintaining sterility of a robotic surgery system used in the operating room.

SUMMARY

A sterile barrier system (or a sterile barrier) for a robotic surgery apparatus can include a drape coupler. The drape coupler can include an external surface configured to face a first surface of a first portion of the robotic surgery apparatus. The drape coupler can include at least one drape coupler fastener positioned at least partially on the external surface and configured to removably attach the drape coupler to the first surface. The drape coupler can be configured to at least partially cover the first surface. The system can include a drape made of a flexible material and coupled to the drape coupler, the drape configured to wrap around a second surface of the first portion of the robotic surgery apparatus, the second surface different from the first surface. The drape coupler and the drape can be sterile.

The system (or barrier) of any of the preceding paragraphs and/or any of the systems described herein can include one or more of the following features. The first portion of the robotic surgery apparatus can include a manipulator unit. The first surface can include a manipulating surface of the manipulator unit. The at least one drape coupler fastener can be configured to removably attach the drape coupler to the manipulating surface of the manipulator unit. The second surface can include at least one side surface of the manipulator unit. The drape can be configured to enclose the at least one side surface of the manipulator unit. The at least one drape coupler fastener can include ferromagnetic material configured to be attached to a magnet positioned on the first surface. The at least one drape coupler fastener can include a plurality of fasteners with ferromagnetic material and configured to be attached to a plurality of magnets positioned on the first surface. The drape can be coupled to the drape coupler along a perimeter of the drape coupler. The drape can include an opening configured to expose a surgical instrument interface of the first portion of the robotic surgery apparatus. The surgical instrument interface can be configured to cause actuation of a surgical instrument. The drape coupler can include at least one removable protector configured to cover the opening of the drape coupler.

The system (or barrier) of any of the preceding paragraphs and/or any of the systems described herein can include one or more of the following features. The drape coupler can include at least one region made at least partially of flexible material. The at least one region can be positioned adjacent to the opening and configured to collapse and expand. The at least one region can include first and second regions. The first region can be positioned adjacent to a first side of the opening. The second region can be positioned adjacent to a second side of the opening opposite the first side. The first and second regions can be configured to collapse and expand in response to movement of the opening. The at least one region can include an insert made at least partially of material that is more rigid than the material of the at least one region. The insert can be configured to cause the flexible material of the at least one region to fold when the at least one region is collapsed. The insert can include at least one tapered edge.

A kit can include a system (or barrier) of any of the preceding paragraphs and/or any of the systems described herein. A kit can include a sterile adapter configured to be received at (or fit into, or cover) the opening and to be removably attached to the surgical instrument interface. The sterile adapter can be configured to provide a sterile barrier between the surgical instrument interface and a surgical instrument.

The kit of the preceding paragraph and/or any of the kits described herein can include one or more of the following features. The sterile adapter can include a plurality of actuator covers configured to couple to a plurality of instrument actuators positioned on the surgical instrument interface. The actuator covers can be configured to move in at least one direction to facilitate at least one of movement or articulation of the surgical instrument mounted to the surgical instrument interface. The actuator covers can be positioned in a first position prior to positioning the cover on the surgical instrument interface. The actuator covers can be configured to be aligned in the first position. The sterile adapter can include a retainer surrounding the actuator covers. The retainer can be configured to maintain positioning of the actuator covers in the first position. The retainer can be removable to permit at least one of the actuator covers to be moved to a position different than the first position.

The system (or barrier) of any of the preceding paragraphs and/or any of the systems described herein can include one or more of the following features. The drape can include at least one drape fastener configured to removably attach the drape to a second surface of the first portion of the robotic surgery apparatus. The at least one drape fastener can include a bendable material and is configured to be wrapped around at least one protrusion on the second surface. The drape can include a first region including a first drape fastener and a second region including a second drape fastener. The first region can be configured to be positioned over the second region and fastened to the second region by attachment of the first drape fastener to the second drape fastener. The drape can include a cover made of a material more rigid than the flexible material of the drape. The cover can be configured to enclose a pin positioned on the second surface and configured to be inserted into an opening of at least one of a surgical instrument insertion device or a camera insertion device of the robotic surgery apparatus. The cover can be configured to provide a sterile barrier between the pin and the opening. The drape can include an insert made of a material more rigid than the flexible material of the drape. The insert can be configured to be positioned in an opening in the first portion of the robotic surgery apparatus that receives a portion of an endoscopic camera of the robotic surgery apparatus. The insert can be configured to provide a sterile barrier between the endoscopic camera and the first portion. The insert can include first and second elongated side surfaces connected at one end and not connected at an opposite end to form an opening. The opening can be configured to be inserted into the opening of the first portion and to receive the endoscopic camera.

The system (or barrier) of any of the preceding paragraphs and/or any of the systems described herein can include one or more of the following features. The drape can include a first pocket configured to receive and at least partially enclose a first hand of a user. The first pocket can be configured to facilitate positioning of the drape on (and/or, optionally, maintain sterility of the drape during attachment of the drape to) the first portion of the robotic surgery apparatus. The drape can include a second pocket configured to receive and at least partially enclose a second hand of a user. The second pocket can be configured to facilitate positioning of the drape on (and/or, optionally, maintain sterility of the drape during attachment of the drape to) the first portion of the robotic surgery apparatus. The second pocket can distinct from the first pocket. The first and second pockets can be positioned to allow a user to lift the drape away from the second surface while maintaining a sterile barrier for the first portion of the robotic surgery apparatus. The drape coupler can be made from material that is more rigid that the flexible material of the drape. The manipulator unit can be hexahedron shaped and the manipulating surface of the manipulator unit can be a bottom surface of the manipulator unit.

An instrument adapter for a robotic surgery apparatus can include a housing configured to receive and support an actuator housing of a surgical instrument. The actuator housing can include a plurality of surgical instrument actuators. The adapter can include a plurality of interface actuators configured to engage with the plurality of instrument actuators of the actuator housing and cause movement of the instrument actuators. Movement of the instrument actuators can cause movement of an end effector of the surgical instrument. The adapter can include a guide configured to receive the actuator housing of the surgical instrument and allow the actuator housing to move (for example, forward and backward, side to side, or otherwise from one position to another position) within the housing. The guide can be configured to allow the actuator housing to be positioned in the housing in a first orientation in which the interface actuators are not engaged with the instrument actuators of the surgical instrument, thereby facilitating removal of the actuator housing from the housing. The adapter can include a fastener configured to engage the actuator housing of the surgical instrument. The fastener can be configured to transition from a first position in which the actuator housing is positioned in the first orientation to a second position in which the actuator is positioned in a second orientation in which the interface actuators are engaged with the instrument actuators of the surgical instrument. The transition of the fastener from the first position to the second position can cause a rotation of the actuator housing.

The adapter of the preceding paragraph and/or any of the adapters described herein can include one or more of the following features. The guide can be configured to receive the actuator housing at an angle. A plane in which the guide is oriented can be tilted relative to a plane in which the interface actuators are oriented. Interface actuators can be oriented in a horizontal plane. The fastener can include a latch configured to be locked when the fastener is in the second position. The fastener can be configured to transition from the first position to the second position to cause rotation of the actuator housing. The fastener can include a protrusion configured to engage with an opening in the actuator housing of the surgical instrument and cause the actuator housing to be rotated. The guide can be configured to not support the actuator instrument housing when the housing is rotated. At least one of the interface actuators can include a distal end configured to face a corresponding instrument actuator opening and a proximal end opposite the distal end. The at least one interface actuator can be tapered toward the distal end. The interface actuators are configured to engage with the instrument actuators of the surgical instrument and move from a first position to a second position to cause the instrument actuators to correspondingly move from the first position to the second position. Movement of the instrument actuators can cause movement of the end effector. The adapter can be sterile.

The adapter of any of the preceding paragraphs and/or any of the adapters described herein can include one or more of the following features. The interface actuators can be positioned in a top portion of the housing. The guide can be positioned in a first portion of a side of the housing. The fastener can be positioned in a second portion of the side of the housing.

A manipulator unit of a robotic surgery apparatus can include a surgical actuation interface configured to receive the instrument adapter of any of the preceding paragraphs and/or any of the instrument adapters described herein.

A method of positioning a surgical instrument in a robotic surgery apparatus can include positioning an instrument interface on the robotic surgery apparatus. The instrument interface can include a housing including a plurality of interface actuators configured to cover (or covering) a plurality of instrument actuators of the robotic surgery apparatus. The method can include inserting an actuator housing of the surgical instrument into the housing of the instrument interface. The method can include rotating the actuator housing within the housing of the instrument interface to cause a plurality of instrument actuators of the surgical instrument to engage with the plurality of instrument actuators of the robotic surgery apparatus covered by the plurality of interface actuators of the instrument interface. Actuation of the instrument actuators of the robotic surgery apparatus can cause corresponding actuation of the instrument actuators. Actuation of the instrument actuators of the robotic surgery apparatus can cause movement of an end effector of the surgical instrument.

The method of the preceding paragraph and/or any of the methods described herein can include one or more of the following features. Inserting the actuator housing of the surgical instrument into the housing of the instrument interface can include inserting the actuator housing at an angle relative to a plane in which the interface actuators are oriented. Inserting the actuator housing at the angle can include guiding the actuator housing through a slot of the housing oriented in a plane that is at the angle relative to the plane in which the interface actuators are oriented. The method can include guiding the actuator housing past the slot of the housing into a portion of the housing adjacent to the slot. When the actuator housing is not rotated, the plurality of instrument actuators of the robotic surgery apparatus (which may be covered by the plurality of interface actuators of the instrument interface) may not be not engaged with the instrument actuators of the surgical instrument. Rotating the actuator housing can include operating a fastener of the instrument interface. Operating the fastener can include moving the fastener upward and locking a fastener latch. The method can include removing the actuator housing from the housing of the instrument interface by unlocking the latch. Unlocking the latch can cause the fastener to move downward and causes the actuator housing to rotate. Rotating the actuator housing can include rotating the actuator housing about an axis traversing a center of a shaft of the surgical instrument, the shaft connecting the actuator housing to the end effector. The instrument interface can be sterile.

An instrument adapter for a robotic surgery apparatus can include an adapter housing configured to receive and support an actuator housing of a surgical instrument. The actuator housing can include a plurality of surgical instrument actuators. The adapter can include a plurality of interface actuators configured to engage with the plurality of instrument actuators of the actuator housing and cause movement of the instrument actuators. Movement of the instrument actuators can cause movement of an end effector of the surgical instrument. The instrument adapter can be configured to facilitate the actuator housing of the surgical instrument to transition from a first orientation in which the interface actuators are not engaged with the instrument actuators of the surgical instrument to a second orientation in which the interface actuators are engaged with the instrument actuators.

The adapter of any of the preceding paragraphs and/or any of the adapters described herein can include one or more of the following features. Transition of the actuator housing from the first orientation to the second orientation can include rotation of the actuator housing. The adapter can include a guide configured to facilitate movement of the actuator housing at an angle. The guide can be oriented in a plane that is tilted relative to a plane in which the interface actuators are oriented. Interface actuators can be oriented in a horizontal plane. A length of the guide can be smaller than a length of the actuator housing of the surgical instrument. The adapter can include a fastener configured to engage the actuator housing of the surgical instrument and cause the actuator housing to transition from the first orientation to the second orientation. The fastener can include a protrusion configured to engage with a groove in the actuator housing of the surgical instrument. The adapter can be configured to facilitate the actuator housing of the surgical instrument to transition from the second orientation to the first orientation. The adapter can be sterile.

A method of preparing a robotic surgery apparatus for a medical procedure (or a method of draping the robotic surgery apparatus) can include covering a manipulator unit of the robotic surgery apparatus with a first sterile barrier. Covering the manipulator unit can include coupling a drape coupler of the first sterile barrier to a bottom surface of the manipulator unit. Covering the manipulator unit can include wrapping a drape of the first sterile barrier around side and top surfaces of the manipulator unit. The drape can be coupled to the drape coupler. The drape can be made of material that is more flexible than material of the drape coupler. The method can include covering an arm of the robotic surgery apparatus supporting the manipulator unit with a second sterile barrier that is distinct from the first sterile barrier. Covering the arm can include coupling the second sterile barrier to the arm. Covering the arm can include wrapping the second sterile barrier around the arm.

The method of any of the preceding paragraphs and/or any of the methods described herein can include one or more of the following features. The first and second sterile barriers can include sterile surfaces configured to face away from the robotic surgery apparatus. Covering the arm with the second sterile barrier can include covering a part of the drape of the first sterile barrier with the second sterile barrier. Covering the part of the drape of the first sterile barrier with the second sterile barrier can facilitate independent movement of the second sterile barrier without causing movement of the drape of the first sterile barrier. Covering the arm with the second sterile barrier can include coupling at least a part of the drape of the first sterile barrier with at least a part of the second sterile barrier. Coupling the drape coupler can include attaching at least one fastener of the drape coupler to at least one fastener positioned on the bottom surface of the manipulator unit. Coupling the second sterile barrier can include attaching at least one fastener of the second sterile barrier to at least one fastener of the arm. The at least one fastener can be positioned on a surface of the arm.

The method of any of the preceding paragraphs and/or any of the methods described herein can include one or more of the following features. Attaching the at least one fastener of the drape coupler to the at least one fastener positioned on the bottom surface of the manipulator unit can include causing magnetic coupling. Attaching the at least one fastener of the second sterile barrier to the at least one fastener of the arm can include causing magnetic coupling. The method can include coupling a sterile adapter to an instrument interface positioned on the bottom surface of the manipulator unit. The instrument interface can be configured to support and actuate an instrument. The method can include covering a pin of the manipulator unit with a sterile roller by positioning the roller on the pin. The pin and roller can be configured to cooperate to extend and retract a camera. The method can include removing first and second sterile barriers. The method can include covering a patient cart of the robotic surgery apparatus with a third sterile barrier. Covering can include coupling the third sterile barrier to the patient cart. Coupling the third sterile barrier to the patient cart can include attaching at least one fastener of the third sterile barrier to at least one fastener. The at least one fastener can be positioned on or adjacent to a surface of the patient cart. Attaching the at least one fastener of the third sterile barrier to the at least one fastener of the patient cart can include causing magnetic coupling. Wrapping the drape of the first sterile barrier around side and top surfaces of the manipulator unit can include coupling the drape to the top surface of the manipulator unit. Coupling the drape of the first sterile barrier to the top surface of the manipulator unit can include causing magnetic coupling.

A method of preparing a robotic surgery apparatus for a medical procedure (or a method of draping the robotic surgery apparatus) can include positioning a first sterile barrier on a first portion of the robotic surgery apparatus. Positioning the first sterile barrier can include coupling a drape coupler of the first sterile barrier to a surface of the first portion of the robotic surgery apparatus configured to support at least one surgical instrument of the robotic surgery apparatus. Positioning the first sterile barrier can include wrapping a drape of the first sterile barrier around one or more other surfaces of the first portion of the robotic surgery apparatus. The drape can be coupled to the drape coupler. The method can include positioning a second sterile barrier that is distinct from the first sterile barrier on a second portion of the robotic surgery apparatus adjacent to the first portion of the robotic surgery apparatus. Positioning the second sterile barrier can include coupling the second sterile barrier to the second portion. Positioning the second sterile barrier can include wrapping the second sterile barrier around the second portion.

The method of any of the preceding paragraphs and/or any of the methods described herein can include one or more of the following features. Material of the drape coupler can be more rigid than material of the drape of the first sterile barrier. Positioning the second sterile barrier can include covering a portion of the drape of the first sterile barrier with the second sterile barrier. Covering can facilitate independent movement of first and second sterile barriers. First and second sterile barriers can include sterile surfaces configured to face away from the robotic surgery apparatus. Coupling the drape coupler can include attaching at least one fastener of the drape coupler to at least one fastener positioned on the surface of the first portion of the robotic surgery apparatus. Coupling the drape coupler can coupling the second sterile barrier can include attaching at least one fastener of the second sterile barrier to at least one fastener of the second portion of the robotic surgery apparatus. The at least one fastener can be positioned on or adjacent to a surface of the second portion. The method can include coupling a sterile adapter to an instrument interface positioned on the surface of the first portion of the robotic surgery apparatus. The instrument interface can be configured to support and actuate the at least one surgical instrument. The method can include covering a pin of the first portion with a sterile cover by positioning the cover on the pin, the pin and cover configured to cooperate to extend and retract a camera. The method can include removing the first and second sterile barriers.

The method of any of the preceding paragraphs and/or any of the methods described herein can include one or more of the following features. The method can include positioning a third sterile barrier on a third portion of the robotic surgery apparatus. The positioning can include coupling the third sterile barrier to the third portion. Coupling the third sterile barrier to the third portion can include attaching at least one fastener of the third sterile barrier to at least one fastener of the third portion. The at least one fastener can be positioned on or adjacent to a surface of the third portion. Attaching the at least one fastener of the third sterile barrier to the at least one fastener of the third portion can include causing magnetic coupling.

A sterile barrier for a robotic surgery apparatus can include a drape made of a flexible material. The drape can include a first surface configured to face a component of the robotic surgery apparatus and a second surface opposite the first surface. The second surface can be sterile and configured to provide a sterile barrier for the component. The barrier can include a first pair of pockets positioned along a first edge of the second surface and configured to receive hands of a user. The first pair of pockets can be configured to facilitate positioning of the sterile barrier on the component. The first pair of pockets can be configured to facilitating maintaining sterility of the second surface of the drape when the drape is attached to the component (and, optionally, when the drape is at least partially wrapped around the component).

The barrier of any of the preceding paragraphs and/or any of the barriers described herein can include one or more of the following features. The barrier can include a plurality of fasteners positioned on the first surface of the drape. The fasteners can be configured to removably position the drape on the component. The fasteners can include ferromagnetic material configured to be attached to at least one magnet (and/or a plurality of magnets) positioned on (or adjacent to) a surface of the component. At least one of the fasteners can be positioned in a region of the drape that overlaps a pocket of the first pair of pockets. The first pair of pockets can include visual indicators, which may be positioned on interior surfaces of the first pair of pockets. The visual indicators can be configured to guide the user to insert the hands in a correct position into the first pair of pockets. The barrier can include a second pair of pockets positioned along the first edge of the second surface and configured to receive the hands of the user. The barrier can include a first fastener positioned on an exterior surface of a first pocket of the first pair of pockets. The exterior surface of the first pocket of the first pair of pockets can be part of the second surface of the drape. The barrier can include a second fastener positioned on an exterior surface of a second pocket of the first pair of pockets. The exterior surface of the second pocket of the first pair of pockets can be part of the second surface of the drape. The first and second fasteners can be configured to be attached to another pair of fasteners to retain the drape wrapped around a portion of the component.

The barrier of any of the preceding paragraphs and/or any of the barriers described herein can include one or more of the following features. The barrier can include a third fastener positioned on an exterior surface of a first pocket of the second pair of pockets. The barrier can include a fourth fastener positioned on an exterior surface of a second pocket of the second pair of pockets. The third and fourth fasteners can be configured to be attached to the first and second fasteners to retain the drape wrapped around the portion of the component. The barrier can include a drape coupler made of a material more rigid that the flexible material of the drape, wherein the drape is coupled to the drape coupler. The barrier can include at least one fastener configured to be wrapped around a protrusion of the component thereby tightening the drape around the protrusion. The barrier can include a second pocket positioned below a pocket of the first pair of pockets. The second pocket can be configured to receive a first portion of the hand of the user to facilitate wrapping the drape at least partially around the component. The second pocket can be configured to receive only the first portion of the hand but not the entire hand. The barrier can include a third pocket positioned along a second edge of the drape that is opposite the first edge of the drape along which the first pair of pockets is positioned. The third pocket can be configured to receive a second portion of the hand of the user to facilitate wrapping the drape at least partially around the component. The third pocket can be configured to receive only the second portion of the hand but not the entire hand.

A kit can include first and second sterile barriers of any of the preceding paragraphs and/or any of the sterile barriers described herein. The first sterile barrier can include a first drape. The second sterile can include a second drape. The first drape can be configured to cover the component. The second drape can be configured to cover a second component of the robotic surgery apparatus adjacent to the component. The second drape can be configured to cover a portion of the first drape.

The kit of the preceding paragraph and/or any of the kits described herein can include one or more of the following features. The second drape can include first and second fasteners, which can be positioned on opposite sides of the second drape. The first and second fasteners can be configured to be attached to each other to retain positioning of the second drape over the first drape. The kit can include at least one sterile cover configured to cover an instrument interface of the component. The instrument interface can be configured to support and actuate a surgical instrument. The kit can include at least one sterile roller configured to cover a pin of the component. The pin and roller can be configured to cooperate to extend and retract a camera. The kit can include a third sterile barrier including a third drape. The third drape can be configured to be positioned on a third component of the robotic surgery apparatus and/or to provide a sterile barrier for the third component.

A robotic surgery apparatus can include a component including a housing with an external surface. The apparatus can include a plurality of component fasteners positioned on the external surface of the housing. The plurality of component fasteners can be configured to couple with a plurality of drape fasteners of a sterile drape. The sterile drape can be configured to cover a portion of the surface of the housing and to provide a sterile barrier for the portion of the surface. A number of component fasteners in the plurality of component fasteners can exceed a number of drape fasteners in the plurality of drape fasteners, permitting the drape to be positioned on the housing of the component in a plurality of orientations and to cover a plurality of different portions of the surface of the housing. When the drape is positioned on the housing, at least one component fastener of the plurality of component fasteners may not be coupled to any of the drape fasteners of the plurality of drape fasteners.

The apparatus of any of the preceding paragraphs and/or any of the apparatuses described herein can include one or more of the following features. The component fasteners can be configured to support the drape. At least one component fastener can include a magnet. The external surface of the housing can include a recess. The magnet can be configured to be positioned in the recess. The recess can be configured to receive a drape fastener. The magnet can be configured to be positioned at a bottom of the recess. The recess can include at least one wall oriented substantially perpendicular to a surface of the magnet configured to couple with the drape fastener. The apparatus can include electronic circuitry configured to detect positioning and orientation of the drape. The electronic circuitry can be configured to determine if the drape is correctly positioned and generate an indication in response to a determination that the drape is not correctly positioned. The electronic circuitry can include at least one proximity sensor. The component can include a patient cart. The at least one component fastener can include indicia on a surface of the at least one component fastener. The indicia can be configured to facilitate coupling of a drape fastener.

A method of preparing a robotic surgery apparatus for a medical procedure (or a method of draping the robotic surgery apparatus) can include, from a plurality of sterile barrier positions, identifying a desired position of a sterile barrier on a component of the robotic surgery apparatus. The method can include covering at least a portion of a surface of the component with the sterile barrier by positioning the sterile barrier in the desired position. The positioning can include coupling a plurality of sterile barrier fasteners to a subset of a plurality of fasteners of the component.

The method of any of the preceding paragraphs and/or any of the methods described herein can include one or more of the following features. A number of the fasteners of the component can exceed a number of the sterile barrier fasteners. Positioning the sterile barrier can include not coupling any of the sterile barrier fasteners to at least one fastener of the component. The method can include removing the sterile barrier by decoupling the plurality of sterile barrier fasteners from the subset of the plurality of fasteners of the component. The method can include verifying that the sterile barrier is correctly positioned based on an output of an electronic circuitry of the robotic surgery apparatus. The electronic circuitry can be configured to detect if the sterile barrier is correctly positioned in the desired position and output an indication that the sterile barrier is not correctly positioned.

A robotic surgery apparatus can include a component including a housing with an external surface. The apparatus can include a component fastener positioned on the external surface of the housing. The component fastener can be configured to couple with a drape fastener of a sterile drape. The sterile drape can be configured to cover a portion of the surface of the housing and to provide a sterile barrier for the portion of the surface. At least one dimension of the component fastener can exceed at least one corresponding dimension of the drape fastener, permitting the drape to be positioned on the housing of the component in a plurality of orientations and to cover a plurality of different portions of the surface of the housing. The component fastener can be configured to support the drape.

The apparatus of any of the preceding paragraphs and/or any of the apparatuses described herein can include one or more of the following features. The at least one dimension can include length. The component fastener can be configured to support the drape.

A method of preparing a robotic surgery apparatus for a medical procedure (or a method of draping the robotic surgery apparatus) can include, from a plurality of sterile barrier positions, identifying a desired position of a sterile barrier on a component of the robotic surgery apparatus. The method can include covering at least a portion of a surface of the component with the sterile barrier by positioning the sterile barrier in the desired position. The positioning can include coupling a sterile barrier fastener to a component fastener of the component. At least one dimension of the component fastener can exceed at least one corresponding dimension of the drape fastener.

The method of any of the preceding paragraphs and/or any of the methods described herein can include one or more of the following features. The at least one dimension of the component fastener exceeding the at least one corresponding dimension of the drape fastener can permit the drape to be positioned in a plurality of orientations and to cover a plurality of different portions of the surface of the component. The at least one dimension can include length. The component fastener can be configured to support the drape.

Any of the sterile barriers and/or adapters of any of preceding paragraphs and/or described below can be used with any of the robotic surgery system components.

In some cases, a robotic surgery system as described and/or illustrated is provided. In some cases, one or more sterile barriers as described and/or illustrated are provided. In some cases, one or more sterile adapters as described and/or illustrated are provided. In some cases, one or more kits as described and/or illustrated are provided.

In some cases, a method of using and/or operating a robotic surgery system or any of its components as described and/or illustrated is provided. In some cases, methods of preparing a robotic surgery apparatus for a medical procedure as described and/or illustrated are provided. Any of such methods can include positioning one or more sterile barriers and/or adapters on any of the components of the robotic surgery system (or covering any of the components with any of the sterile barriers) as described and/or illustrated.

Any of the methods of any of the preceding paragraphs and/or described herein can be used with any of the sterile barriers, adapters, kits, and/or robotic surgery systems.

BRIEF DESCRIPTION OF THE DRAWINGS

Embodiments of the present disclosure will now be described hereinafter, by way of example only, with reference to the accompanying drawings in which.

DETAILED DESCRIPTION

Overview of Robotic Surgery System

Using a robotic surgery system in the operating room can require placing one or more components of the system within the sterile field in the operating room, while placing other components of the system outside the sterile field. Creating and maintaining the sterile field in the operating room when components of the robotic surgery system are present can be challenging. For example, non-sterile components of the system (such as, the workstation as described herein) may be placed outside the sterile field, and it is important to ensure that such components or connections between non-sterile and sterile components do not contaminate sterile items, personnel, or the patient within the sterile field. As another example, sterilizing the one or more components of the system positioned within the sterile field may not be practical due to the size and complexity of the one or more components. As described herein, one or more sterile barriers covering one or more components of the system can be utilized to create and maintain the sterile field.

Figure 1A:
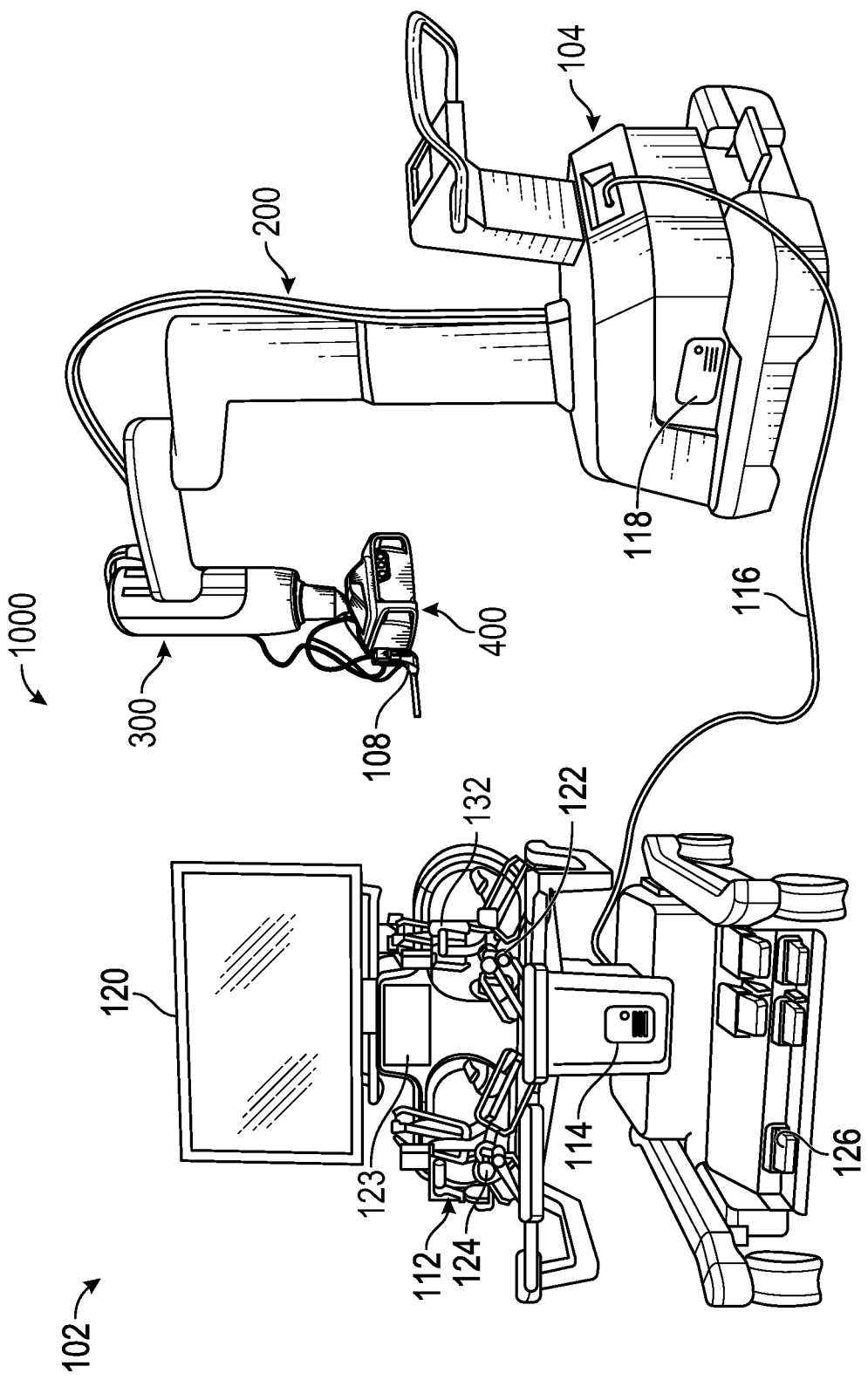
FIGS. 1A-1D illustrate a robotic surgery system.

Referring to FIG. 1A, a robotic surgery system is shown generally at 1000. In some implementations, the robotic surgery system 1000 can be configured to facilitate a medical procedure (for example, surgery) performed via one or more incisions. For a single incision, a single access port can be inserted into the incision to provide access for one or more instruments (sometimes referred to as surgical instruments, tools or surgical tools) or cameras (or other non-tissue manipulating equipment, including advanced visualization equipment).

The system 1000 can include a workstation 102 and a patient cart 104. One or more of the patient cart 104 or the workstation 102 can be moveable. The patient cart 104 can include a manipulator unit or central unit 400 to which one or more instrument insertion and visualization devices 108 can be attached or mounted. The central unit 400 can be supported by an elevating linkage assembly 300 (sometimes referred to as an arm) connected to a boom arm assembly 200 (sometimes referred to as a column) of the patient cart. The central unit 400 can be moveable, such as in three dimensions, to facilitate desired positioning of one or more surgical instruments or cameras. Movement of the central unit 400 can be facilitated by one or more of the arm 300 and column 200. For example, the column 200 can facilitate vertical positioning of the central unit 400, and the arm 300 can facilitate further vertical positioning in addition to lateral movement and rotation of the central unit 400.

The instrument insertion and visualization device 108, which can be removably mounted to the central unit 400, can support at least one surgical instrument and one or more cameras (not shown) that image a site of interest, such as a surgical site. The instrument insertion and visualization device 108 can support two or more instruments (not shown). The one or more cameras can include a primary camera and at least one secondary camera. The primary camera and the secondary camera may provide different viewing angles, perform different functions and/or produce different images. At least one of the primary camera and the secondary camera may be a two-dimensional (2D) or a three-dimensional (3D) camera.

The workstation 102 can include an input device 112 that receives operator input and produces input signals and may also be configured to generate feedback to the operator or user. The feedback can be visual, auditory, haptic, or the like. The input device 112 can be implemented using a haptic interface available from Force Dimension, of Switzerland, for example. The operator can be a surgeon.

The workstation 102 can further include electronic circuitry 114 in communication with the input device for receiving the input signals and generating control signals for controlling the robotic surgery system, which can be transmitted to the patient cart 104 via an interface cable 116. In some cases, data transmission can be wireless and the interface cable 116 may not be present. The electronic circuitry 114 can include one or more processors or controllers. The electronic circuitry 114 can function as a master for controlling movement of one or more surgical instruments or cameras mounted to the patient cart 104. The patient cart can include electronic circuitry 118, which can include one or more processors or controllers. The electronic circuitry 118 can function as a slave and be controlled by the electronic circuitry 114. Communication between the electronic circuitry 114 of the workstation 102 and the electronic circuitry 118 of the patient cart 104 may wired (such as, via the cable 116) or wireless. The workstation 102 may be located remotely from the patient cart 104, such as outside the operating room or in a non-sterile area of the operating room.

The input device can include a right input device 132 and a left input device 112 for controlling respective right and left instruments (not shown). The right input device 132 can include a right hand controller 122 (sometimes referred to as a hand grip or handpiece), and the left input device 112 can include a left hand controller 124. The right and left hand controllers 122 and 124 can be mechanically and/or electrically coupled to the respective input devices 132 and 112. Alternatively, the right and left hand controllers 122 and 124 may be wirelessly coupled to the respective input devices 132 and 112 or may be wireless coupled directly to the workstation 102. The right and left hand controllers 122 and 124 can be grasped by the operator's hands and moved to produce input signals at the respective input devices 132 and 112.

In some cases, when there are two instruments at the patient cart 104, the right and left hand controllers 122 and 124 may respectively control the two instruments. In some cases, when there are more than two instruments, the right and left hand controllers 122 and 124 may be used to select two of the multiple instruments that the operator wishes to use at any given time. In some cases, when there is only one instrument, one of the right and left hand controllers 122 and 124 may be used to select the single instrument.

The input devices 132 and 112 may generate input signals representing positions of the hand controllers 122 and 124 within an input device workspace (not shown). In some cases where the input devices 132 and 112 are coupled directly and wirelessly to the workstation, they would include the necessary sensors to allow wireless control such as an accelerometer, a gyroscope and/or magnetometer. In other cases, a wireless connection of the input devices 132 and 112 to the workstation 102 may be accomplished by the use of camera systems alone or in combination with the described sensors. Such sensors for wireless functionality may also be placed in each handpiece to be used in conjunction with the input devices 132 and 112 to independently verify the input device data. The electronic circuitry 114 can be in communication with the input devices 132 and 112 for receiving the input signals.

The electronic circuitry 118 of the patient cart 104 can receive control signals from the electronic circuitry 114 and produce slave control signals operable to control the instrument insertion and visualization device 108 and one or more instruments (and their respective end effectors) and/or cameras during a surgical procedure. The one or more instruments can include dexterous tools, such as grippers, needle drivers, staplers, dissectors, cutters, hooks, graspers, scissors, coagulators, irrigators, and suction devices used for performing a surgical procedure (such as a laparoscopic surgical procedure). While both master and slave electronic circuitry 114 and 118 are illustrated, in some cases a single electronic circuitry may be used to perform both master and slave functions.

The workstation 102 can also include a user interface, such as a display 120 in communication with the electronic circuitry 114 for displaying information (such as, body cavity images) for a region or site of interest (for example, a surgical site, a body cavity, or the like) and other information to the operator. The display 120 can display real time images or other graphical depictions of a surgical site produced by one or more cameras of the visualization device (not shown) and/or one or more cameras of the instrument insertion and visualization device 108. The workstation 102 may include right and left graphical depictions (not shown) displayed on the display 120 respectively for the right and left side instruments (not shown). The graphical depictions may be displayed at a peripheral region of the display 120 to prevent obscuring a live view of the surgical workspace also displayed on the display. The display 120 may further be operable to provide other visual feedback or instructions to the user.

The workstation 102 can include a second auxiliary display 123 to display auxiliary surgical information to the user, for example, patient medical charts, pre-operation images and surgical data. In some cases, the auxiliary display 123 may be a touch display and may also be configured to display graphics representing additional inputs for controlling the workstation 102, the patient cart 104, and/or specific functions thereof.

The workstation 102 can also include one or more controllers, such as one or more footswitches or pedals 126, for controlling the robotic surgery system. For example, one or more pedals 126 can include a clutch pedal that allows repositioning the hand controllers 122 or 124 without corresponding movement of the respective associated instrument. The clutch pedals 126 can provide input signals to the electronic circuitry 114, and the electronic circuitry may inhibit movement of the associated instrument while the footswitch 126 is depressed.

Figure 1B:
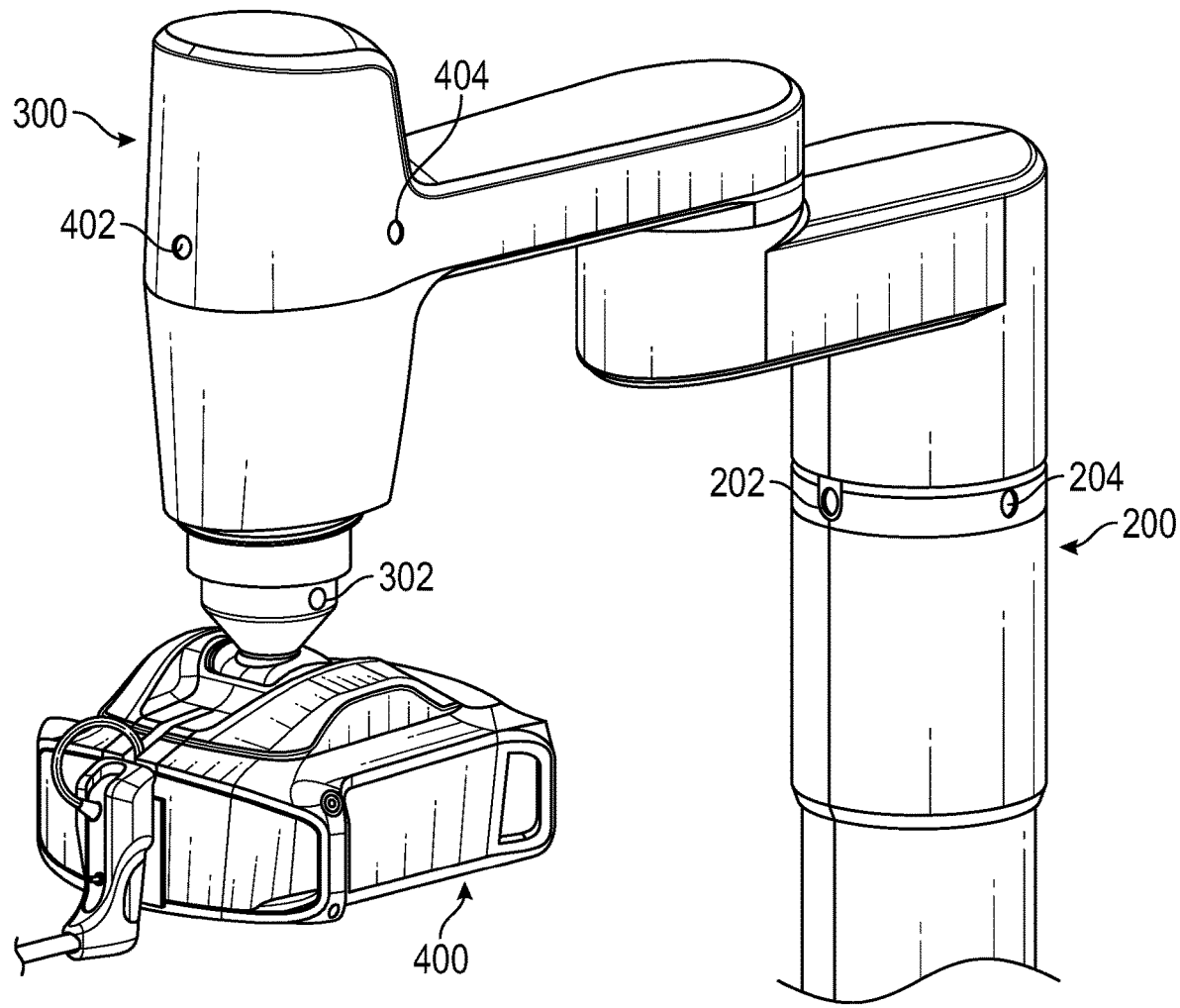
Figure 1C:
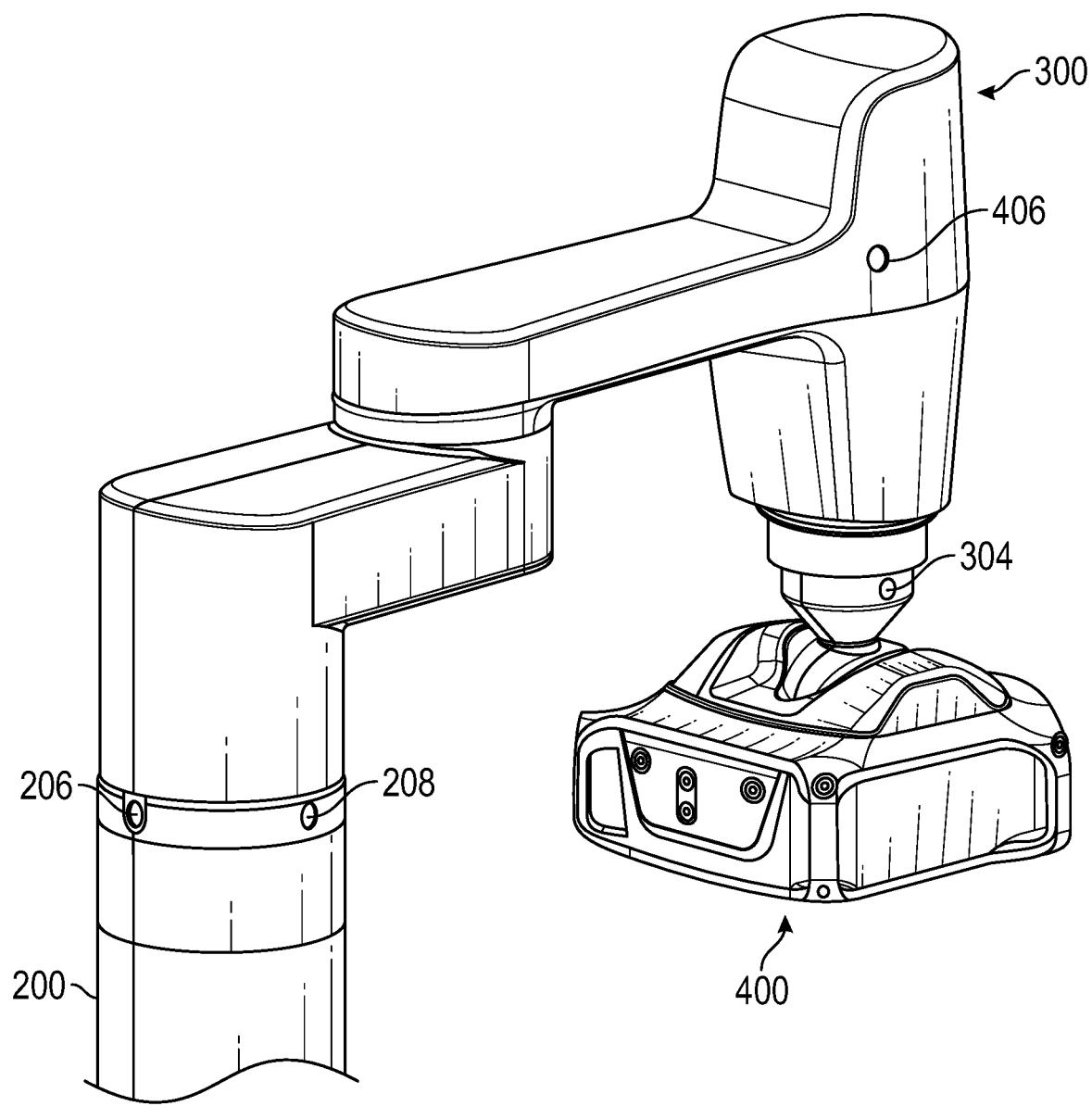

FIG. 1B illustrates a close-up front perspective view of a portion of the patient cart 104. The illustrated portion includes the central unit 400 (which can be shaped as a hexahedron), the arm 300, and an upper portion of the column 200. FIG. 1C illustrates a close-up rear perspective view of the portion of the patient cart 104 illustrated in FIG. 1B. The central unit 400 can include one or more attachments or fasteners 302 and 304, which can be positioned around the perimeter or circumference of the central unit as illustrated (such as, on opposite sides) and/or positioned around the perimeter or circumference of a lower portion of the arm 300 (proximate near where the central unit 400 is attached, mounted, connected or otherwise coupled to the arm). The arm 300 can include one or more attachments or fasteners 402, 404, and 406, which can be positioned around the perimeter or circumference of the arm as illustrated. Fastener 402 can be positioned in the middle (for example, in line or substantially in line with a center of the central unit 400). Fasteners 404 and 406 can be positioned on the sides. The column 200 can include one or more attachments or fasteners 202, 204, 206, and 208, which can be positioned on opposite sides (or otherwise spaced apart, for example, equally spaced apart) around the perimeter or circumference of the column as illustrated. As described herein, the one or more attachments can be configured to facilitate attachment (such as, removable attachment) of one or more sterile barriers, such as drapes, to cover (or enclose) the one or more components of the patient cart 104. For example, any of the fasteners can include a magnetic material for removably attaching or affixing a sterile barrier, such as a drape. Attachment may be formed when an attachment portion of the drape that includes a ferromagnetic material is brought into proximity of or into contact with a fastener. Any of the fasteners of the robotic surgery system components and/or sterile barriers can be circular, rectangular, square, or the like. In some cases, one or more of the fasteners may be three-dimensionally shaped in addition to having a shape. In some cases, the attachment portion of the drape that includes the ferromagnetic material may be three-dimensionally shaped. In some cases, there may be more or less fasteners positioned on the one or more of components 400, 300, and 200 than illustrated in FIGS. 1B-1C. In some cases, one or more fasteners can be positioned in different locations. In some cases, one or more fasteners can be positioned on or adjacent to the surface of the robotic surgery system component.

Figure 1D:
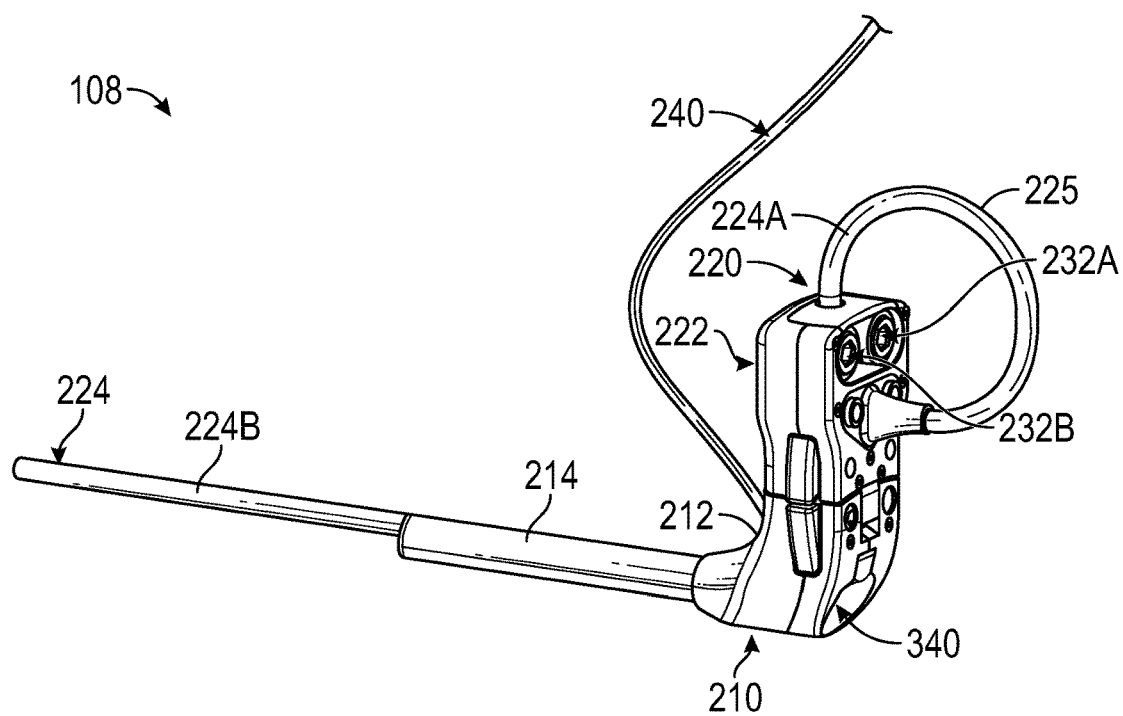

FIG. 1D illustrates the instrument insertion and visualization device 108. The instrument insertion and visualization device 108 can include an insertion device 210 and a visualization device 220. The insertion device 210 can include a housing 212 and a plurality of passages, lumens, or channels 214 for inserting and guiding one or more instruments or cameras. The plurality of channels 214 can be enclosed in another housing as illustrated in FIG. 1D. The two housings can be connected as shown. The plurality of channels 214 can also permit insertion of a primary camera 224. The primary camera be an endoscope or endoscopic camera. A distal end 224B of the primary camera 224 can extend beyond the housing including the plurality of channels 214. At least a portion of the distal end 224B can be positioned near or in the site of interest (such as, to provide image data of the site of interest). One or more cameras (such as, imaging components, including one or more lenses) can be positioned at the distal end 224B. The primary camera 224 can also include a proximal end 224A.

The visualization device 220 can include a housing 222 to which the proximal end 224A of the primary camera can be attached (removably or non-removably). The housing 222 can include an opening in which one or more sterile drivers, such as at least one of 232A or 232B (individually or collectively referred to as 232), can be positioned. The one or more drivers 232 can contact or grip the primary camera 224 and move the primary camera through the opening in the housing 222 and a channel of the plurality of channels 214 so that the distal end 224B extends away from one or more of the housings 212 or 222 or retracts back toward or into one or more of the housings 212 or 222. A camera tube 225 of the primary camera 224 can form a loop around at least a portion of the housing 222. The diameter of the loop can be increased when the distal end 224B is retracted toward or into one or more of the housings 212 or 222 and be decreased when the distal end 224B is extended away from one or more of the housings 212 or 222. In some cases, the visualization device 220 may be coupled to another part of the insertion device 210. In some cases, the visualization device may not be coupled to the insertion device 210 and instead be coupled to another part of the central unit 400. In some cases, the primary camera 224 may not include a loop and instead be linearly inserted into and through the insertion device 210 but otherwise have a distal end 224B of the primary camera 224 function as described above.

At least a portion of the primary camera tube 225 can be flexible or substantially flexible in order to form the loop and/or be guided through the one or more openings and/or channels as described herein. In some cases, at least a portion of the primary camera tube 225 can be flexible or substantially flexible in order to facilitate manipulation of the primary camera at the site of interest, for example, to provide the operator with the desired camera view. In some cases, looping the camera 224 upward around at least the portion of the housing 222 as described can permit the primary camera to have sufficient length for reaching near and/or into the site of interest, while eliminating or reducing the risk of the primary camera 224 (or at least desired portion thereof) coming into contact with non-sterile object, such as the floor or a portion of the system 1000 not covered or protected by a sterile barrier.

One or more cables 240 can be used to transmit control signals and data, such as analog or digital image data provided by the one or more cameras positioned at the distal end 224B or in the insertion device 210, to the patient cart 104 and/or the workstation 102. In some cases, transmission can be wireless and one or more cables 240 may not be present.

The insertion device 210 can include one or more instrument channels for positioning one or more surgical instruments. The one or more instruments can be loaded (into the instrument channels) through one or more openings 340 formed in the rear of the housing 212 of the insertion device 210. In some cases, one or more secondary cameras can be integrated in the insertion device 210 or be removably positioned in the insertion device.

In operation, the insertion device 210 and visualization device 220 can be attached to each other. For instance, the housings 220 and 210 can be attached to each other. Attachment can be removable and can facilitate insertion into and movement of the primary camera 224 (such as, the distal end 224B) through the housings 220 and 210 and the channel of the plurality of channels 214. In some cases, the insertion device 210 can be attached to a first portion of the central unit 400 while the visualization device 220 can be attached to a second portion of the central unit, facilitating the entry of the primary camera 224 into and through the insertion device from a range of angle/orientations.

FIGS. 1A-1D illustrate an example of a robotic surgery system and its components, and certain elements may be removed, other elements added, two or more elements combined, or one element can be separated into multiple elements depending on the specification and requirements of the robotic surgery system.

Additional details of the robotic surgery system 1000 and its components, including one or more insertion devices, visualization devices, or cameras, are described in U.S. patent application Ser. No. 16/156,651 filed on Oct. 10, 2018, Ser. No. 16/156,625 filed on Oct. 10, 2018, Ser. No. 16/174,646, filed on Oct. 30, 2018, Ser. No. 16/299,834, filed on Mar. 12, 2019, Ser. No. 16/419,743 filed on May 22, 2019, and Ser. No. 16/419,696 filed on May 22, 2019, the entire disclose of each of which is incorporated by reference and should be considered part of this specification.

Overview of Sterile Barrier

To establish and maintain sterility of one or more components of a robotic surgery system, such as the system 1000, one or more sterile barriers, such as drapes, can be utilized. Such approach can be more practical, efficient and/or effective to sterilizing the one or more components of the robotic surgery system, such as sterilizing external surfaces and/or other parts of the one or more components. Attaching or positioning of such barriers on the one or more components of the robotic surgery system is illustrated in FIGS. 2A-2G. As is illustrated, one or more sterile barriers can be removably attached or positioned to cover one or more components of the patient cart 104, which can be positioned at least partially in the sterile field.

Sterile barriers can help to mitigate the risk of a sterile object or sterile personnel (such as, sterile nurse, surgeon, or the like) coming into contact with a non-sterile surface or object. Sterile barriers can additionally or alternatively protect components of the robotic surgery system from coming into contact with fluids or tissue during the medical procedure.

Figure 2A:
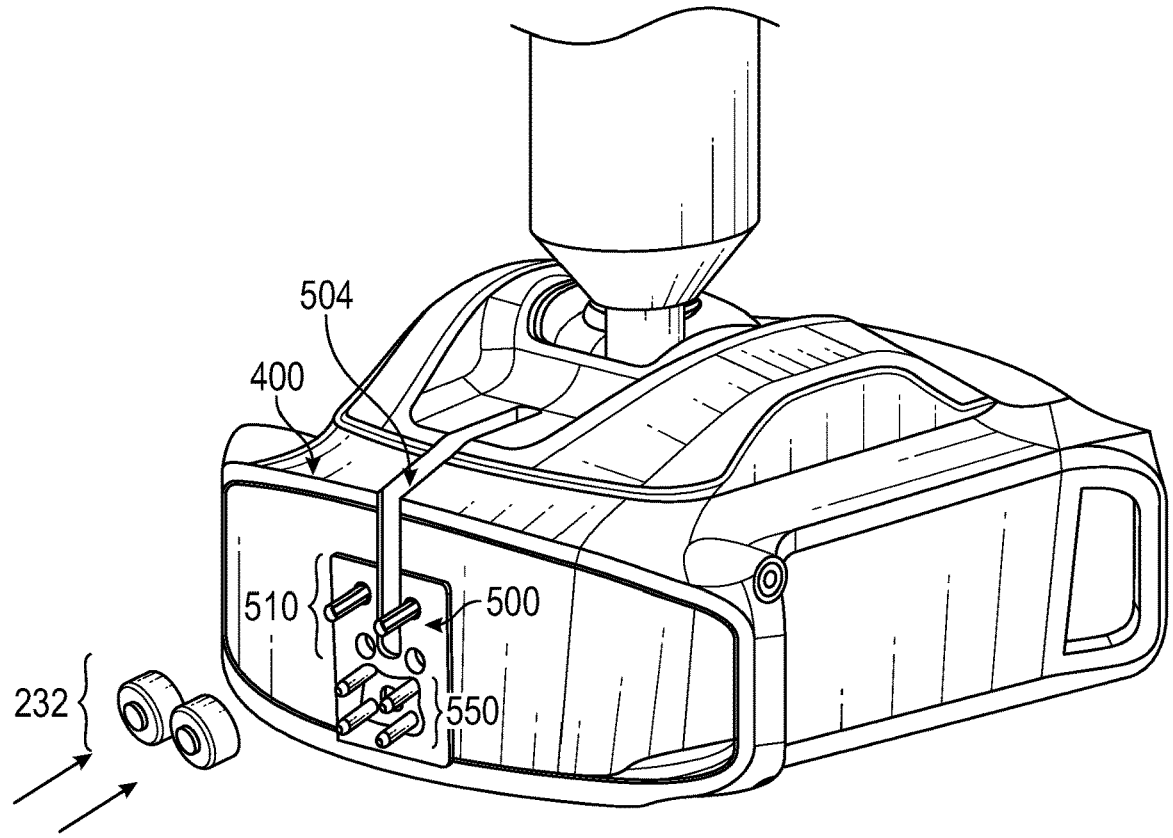
FIGS. 2A-2G illustrate a sterile barrier for the robotic surgery system.

FIG. 2A illustrates an interface 500 of the central unit 400. The interface 500 (which can be referred to as a mounting interface) can be configured to support an instrument insertion and visualization device 108, which can include the insertion device 210 and the visualization device 220. The insertion device 210 can include the plurality of channels 214 for facilitating positioning adjacent to or in the site of interest of one or more surgical instruments and one or more cameras (including, the primary camera 224). The visualization device 220 can facilitate positioning of the primary camera 224 adjacent to or in the site of interest. In some cases, the primary camera 224 can be of length selected to allow at least the distal portion 224B of the primary camera to be advanced toward or into the site of interest and retracted away from the site of interest (such as, toward or into a cannel of the visualization device 220). As described herein, the primary camera 224 can include the camera tube 225, a flexible or substantially flexible portion, that forms a loop around a portion of the visualization device 220, such as the housing 222. The looped portion of the primary camera can be shortened when the primary camera is advanced and lengthened when the primary camera is retracted.

The mounting interface can include an opening or slit 504 for receiving the looped portion of the primary camera. The interface 500 can include one or more posts or pins 510 configured to actuate one or more drivers 232 for advancing the primary camera 224 toward or into the site of interest and/or retracting the primary camera. The interface 500 can include a sterile cover 550 that can be attached to cover one or more additional posts or pins of the mounting interface 500. The one or more pins can be configured to support one or more of the insertion or visualization devices.

One or more drivers 232 and cover 550 can be sterile and form part of a sterile barrier for the central unit 400. A sterile barrier may need to be provided between the mounting interface 500 of a non-sterile surface of the central unit 400 and one or more of a sterile insertion or sterile visualization devices, which can be removably attached to or mounted on the interface 500. The insertion and visualization devices 210 and 220 may be required to be sterile (for example, to maintain sterility of one or more surgical instruments and/or cameras mounted to or positioned in the insertion and visualization devices) in order to protect the site of interest from infection. It can be advantageous to provide a sterile barrier for non-sterile portions of the central unit 400 that may come into contact with the insertion and visualization devices. For example, the primary camera 224 can be advanced or retracted by the one or more sterile drivers 232, which can rotate to advance or retract the camera, as described in more detail in U.S. patent application Ser. No. 16/156,651 filed on Oct. 10, 2018 and Ser. No. 16/156,625 filed on Oct. 10, 2018. As described herein, sterility of the looped portion of the primary camera positioned in the slit 504 can be maintained with a sterile insert (for example, insert 640) positioned in the slit 504. The sterile cover 550 can advantageously maintain sterility of the one or more of insertion or visualization devices mounted to the one or more pins covered by the cover 550.

Figure 2B:
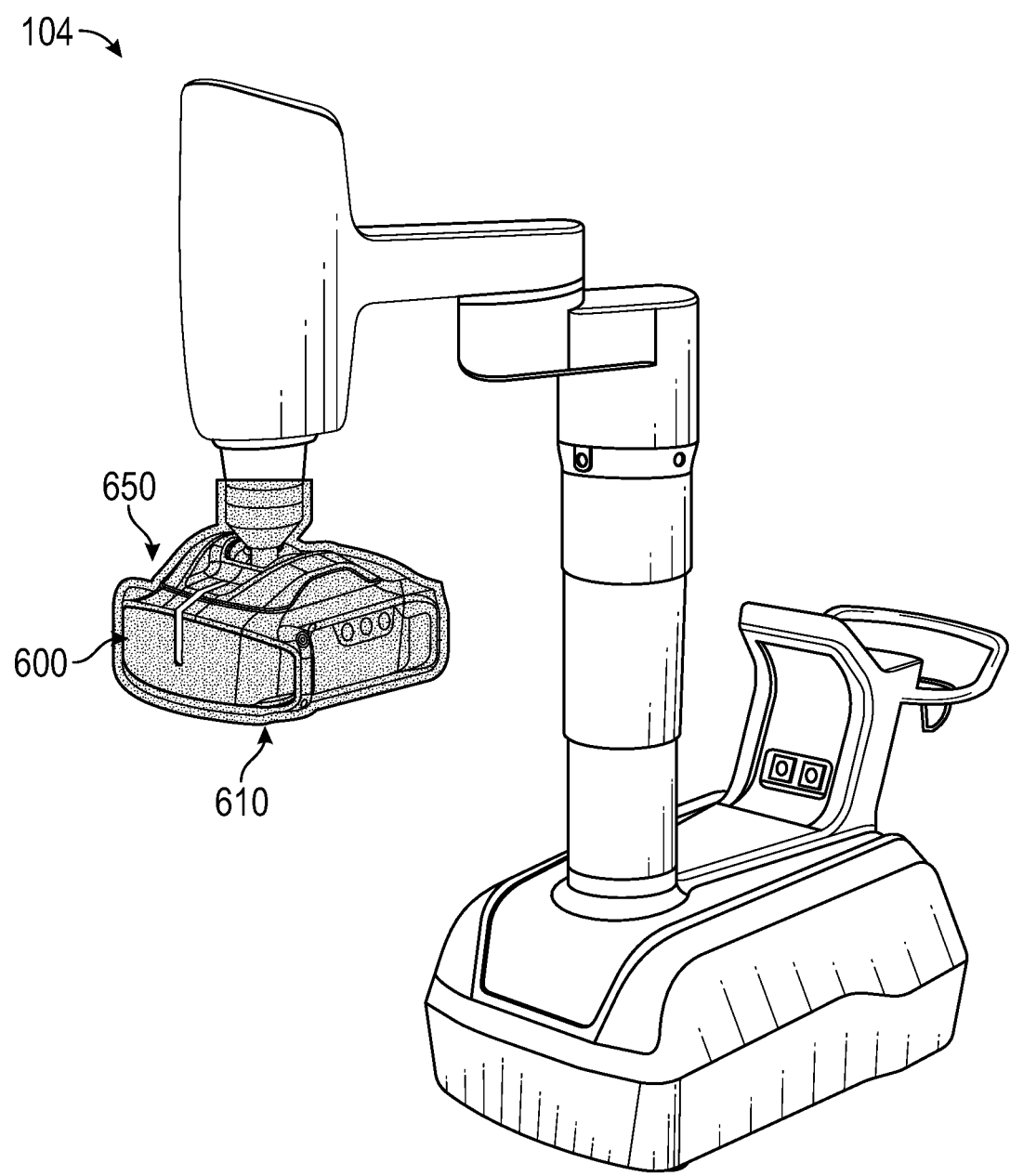
Figure 2C:
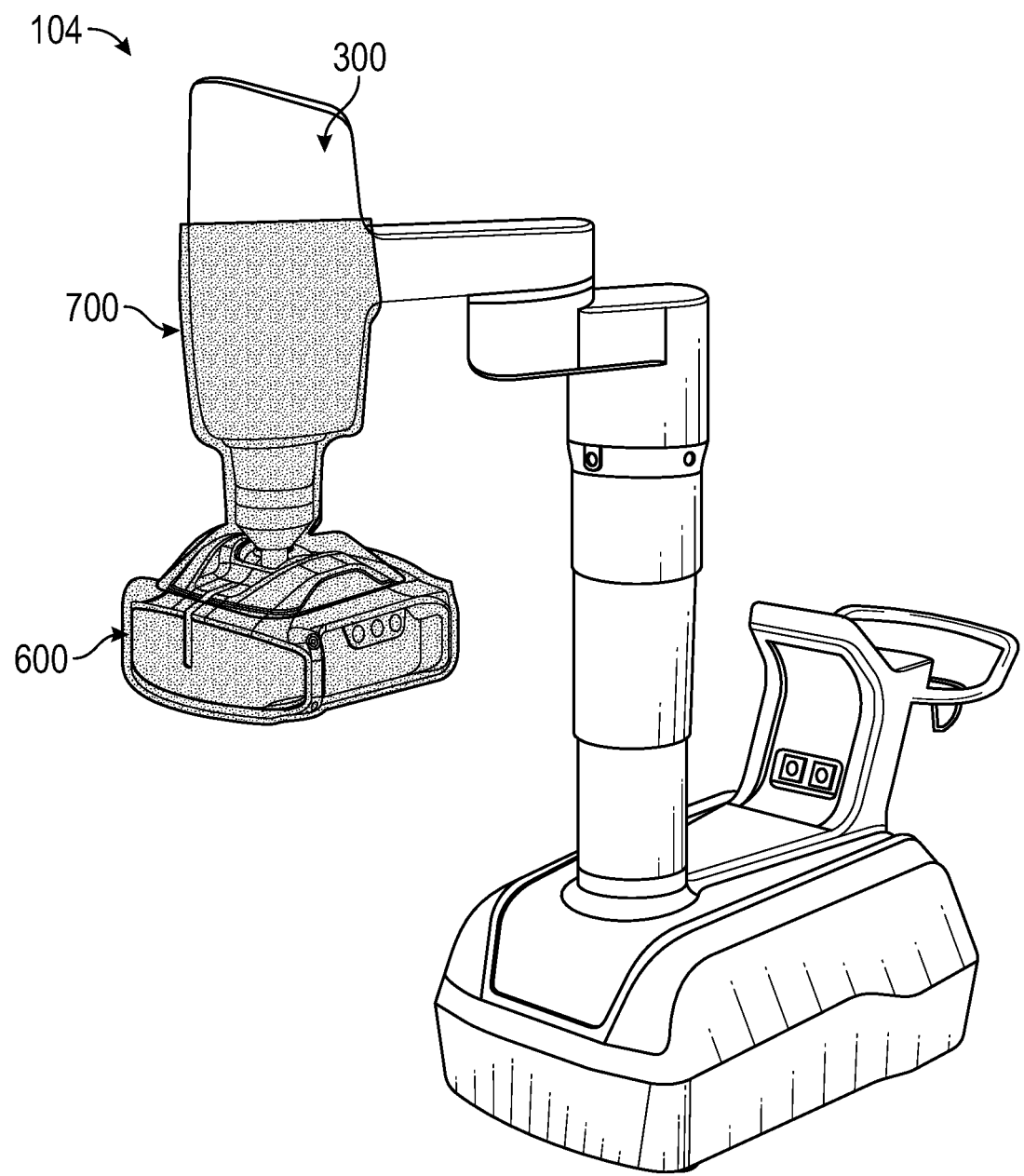

FIG. 2B illustrates covering (such as, enclosing) the central unit 400 with a sterile barrier 650, which can include a drape 600 and a drape coupler 610. FIG. 2C illustrates covering (such as, enclosing) a portion or part of the arm 300 with a sterile barrier, such as a sterile drape 700. As described herein, the drape 700 can overlap a portion of the drape 600 of the sterile barrier 650. In some cases, a portion of the drape 700 can attach, connect or otherwise couple to a portion of the drape 600 by the use of one or more of any of the fasteners described herein.

Figure 2D:
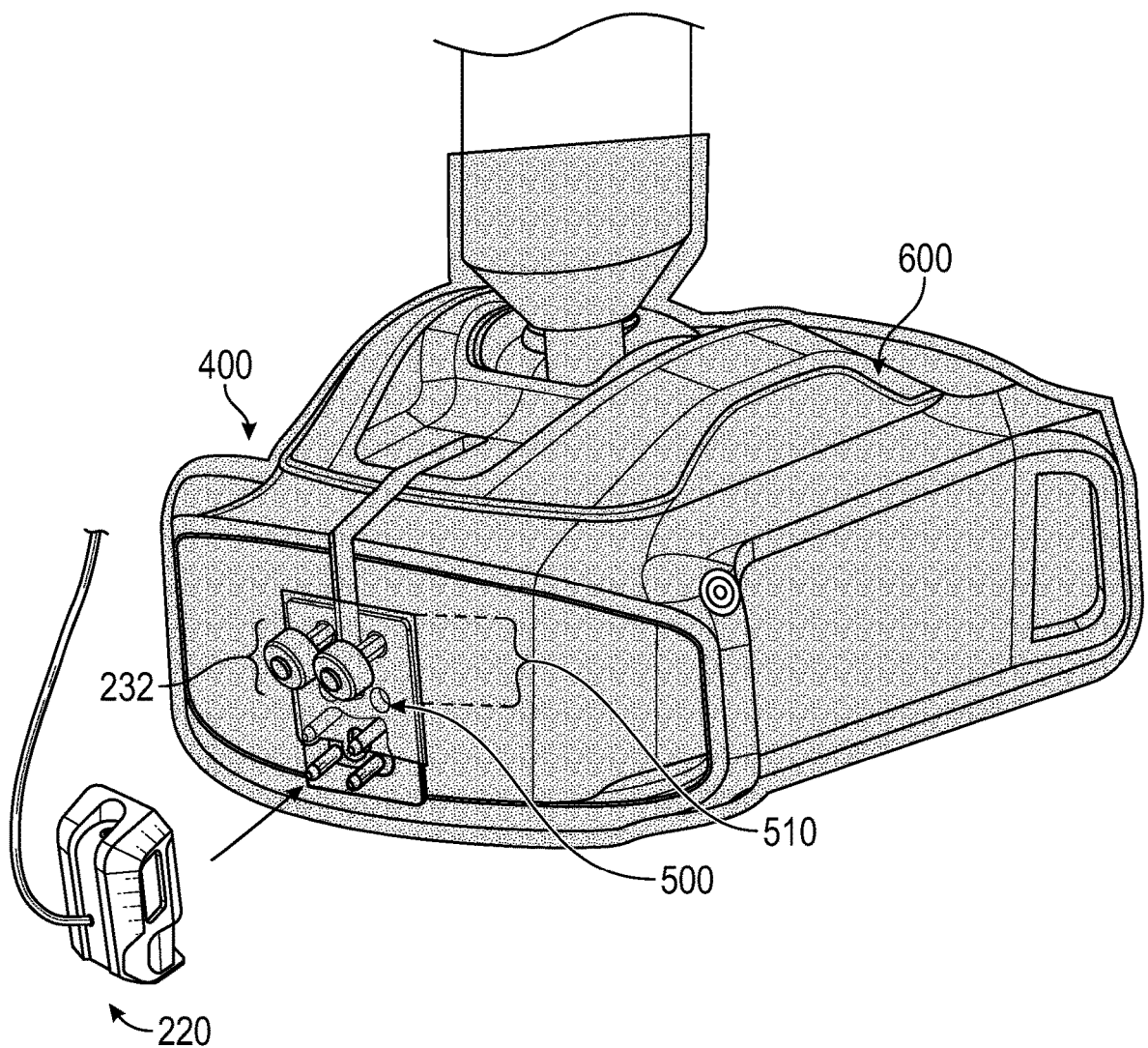
Figure 2E:
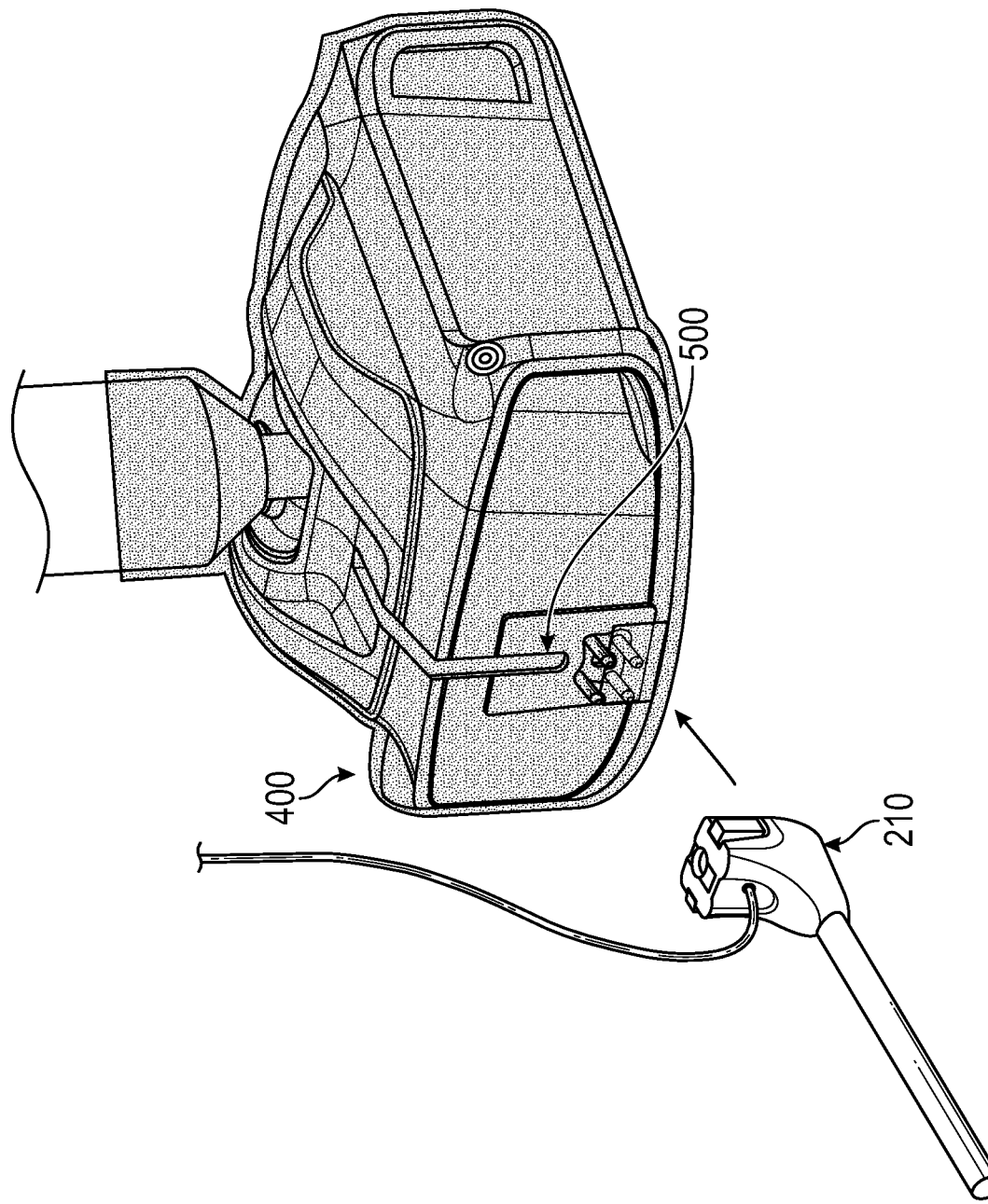

After (or in some cases before) covering the central unit 400 with the sterile drape 600, one or more of the insertion or visualization devices 210 and 220 can be attached to the central unit, such as mounted on the mounting interface 500. As illustrated in FIG. 2D, the visualization device 220 can be mounted to the mounting interface 500. As shown, the visualization device 220 can be positioned on the one or more pins 510 covered by the one or more drivers 232 and the one or more pins covered by the cover 500 (such as, the top two pins) to maintain sterility of the visualization device (and the primary camera attached to the visualization device). After (or in some cases before) the visualization device 220 has been mounted to the mounting interface 500, the insertion device 210 can be mounted to the mounting interfaces, as illustrated in FIG. 2E. The insertion device 210 can be mounted on the one or more pins covered by the cover 500 (such as, the bottom two pins).

Figure 2F:
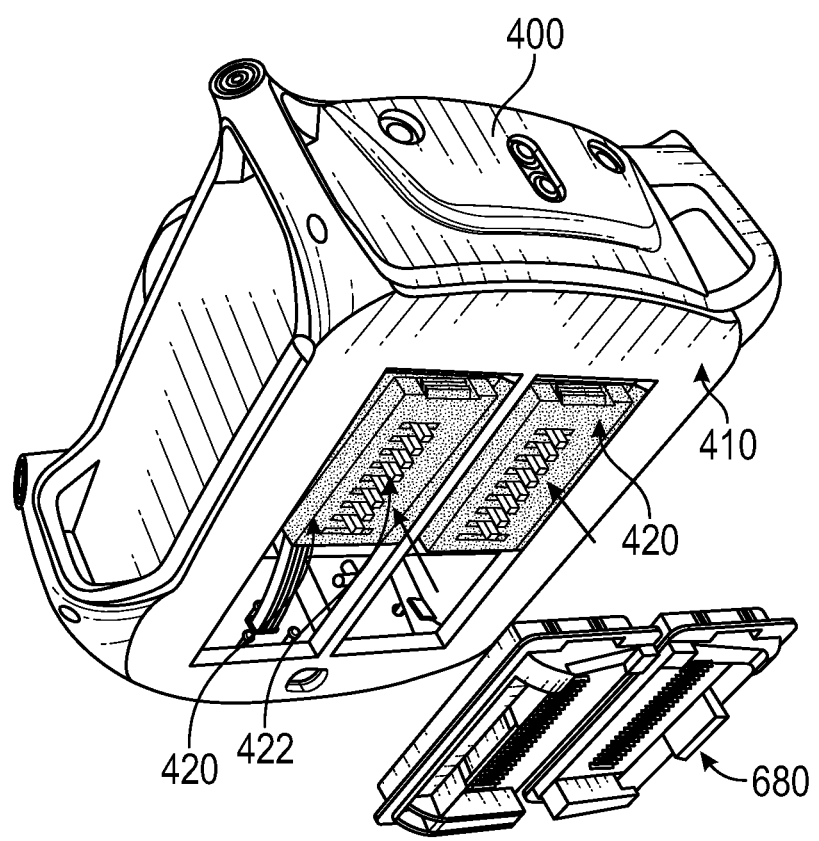
Figure 4A:
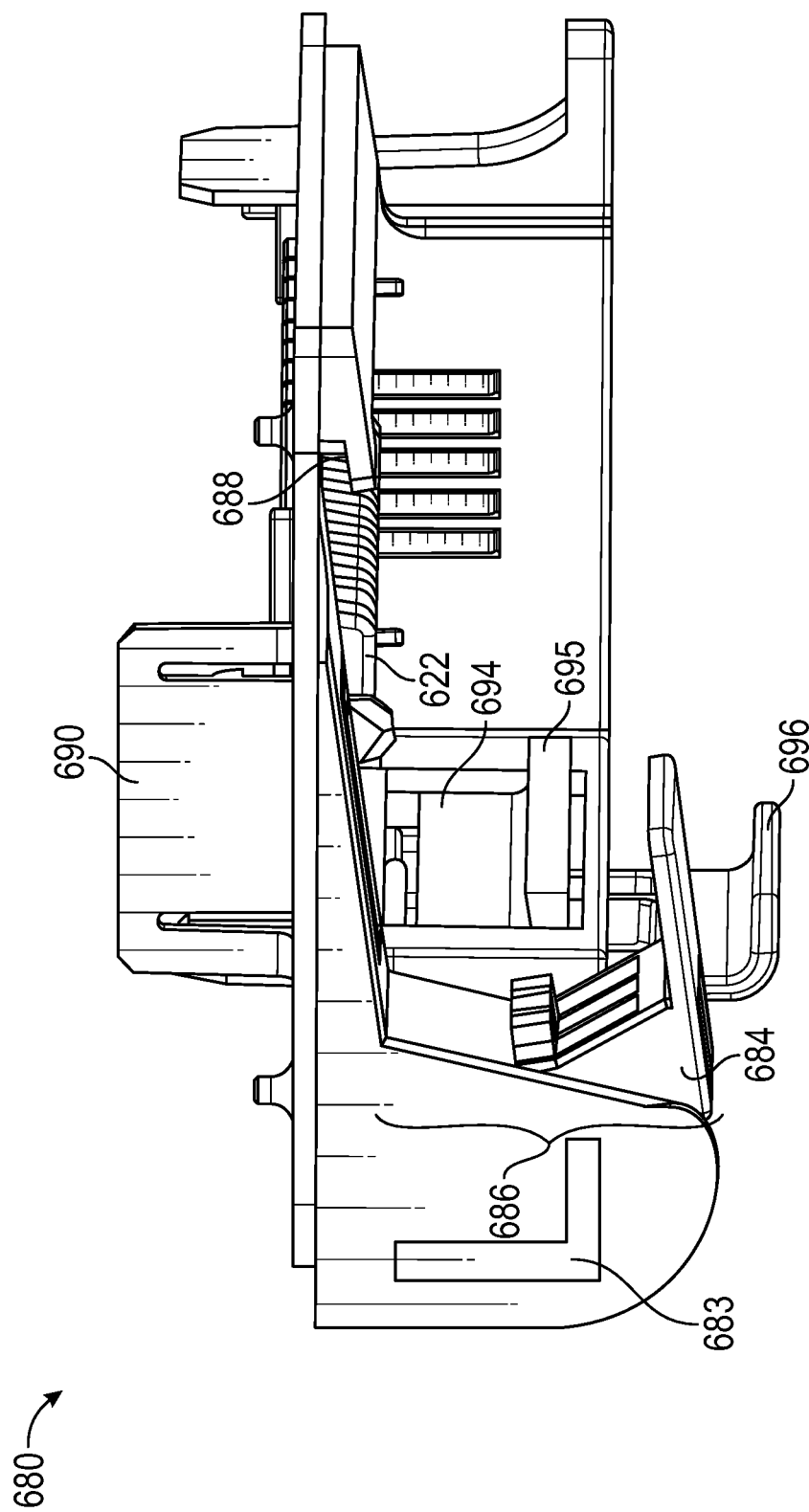
FIGS. 4A-4O illustrate a sterile adapter for a surgical instrument.
Figure 4B:
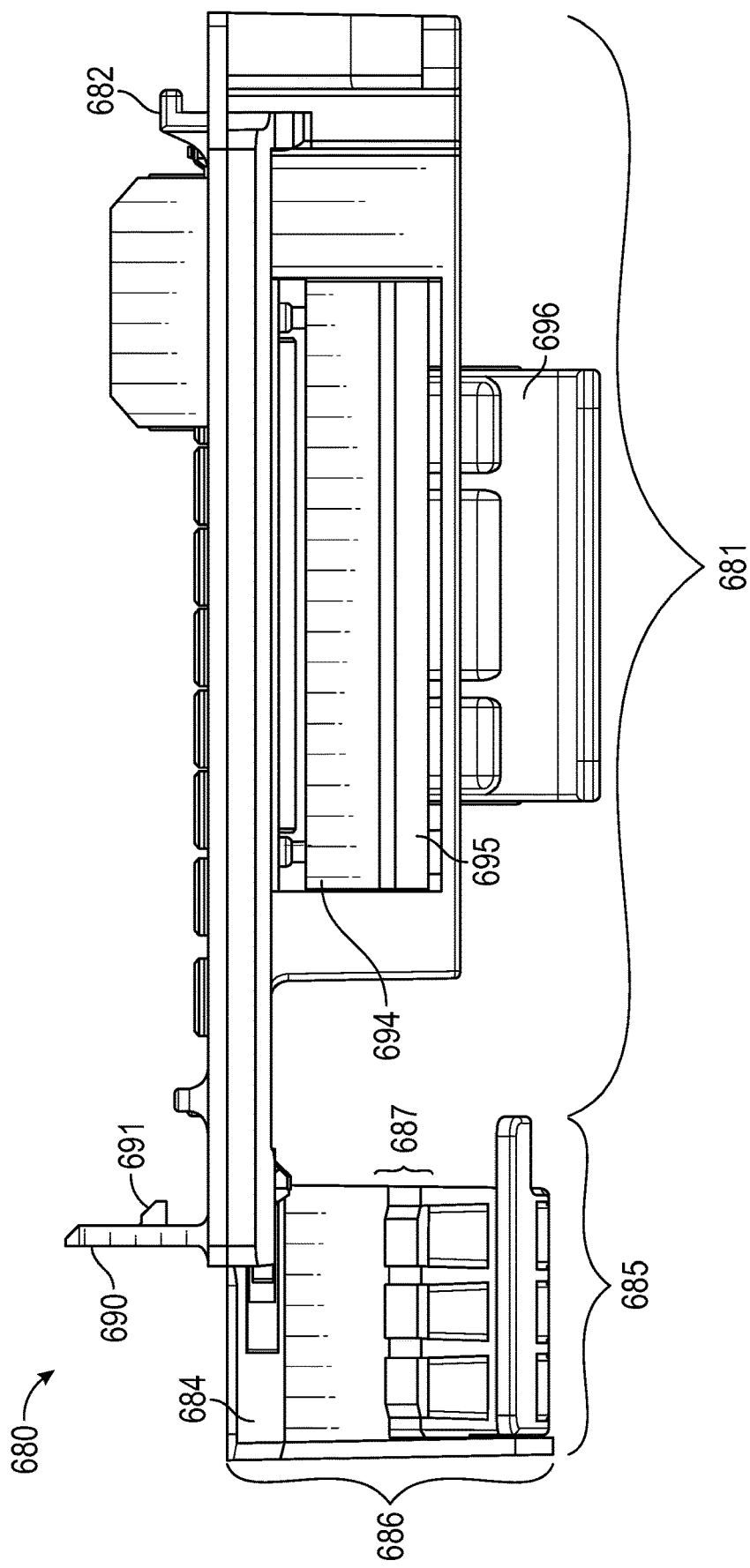
Figure 4C:
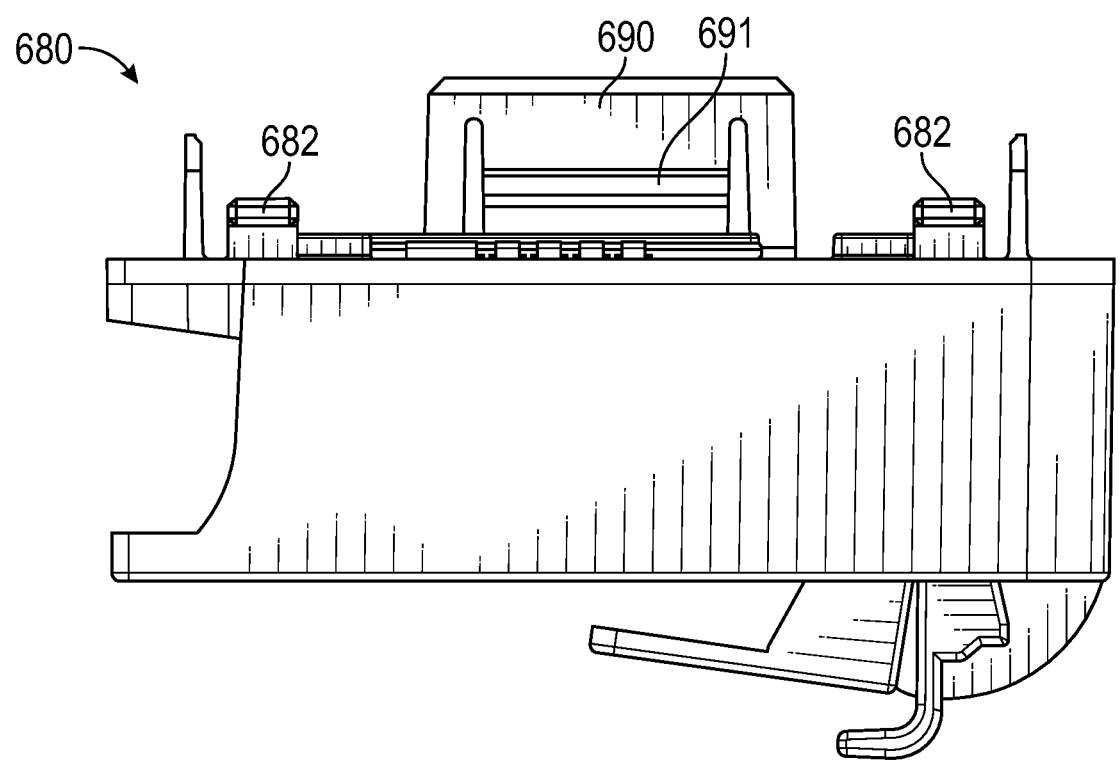
Figure 4D:
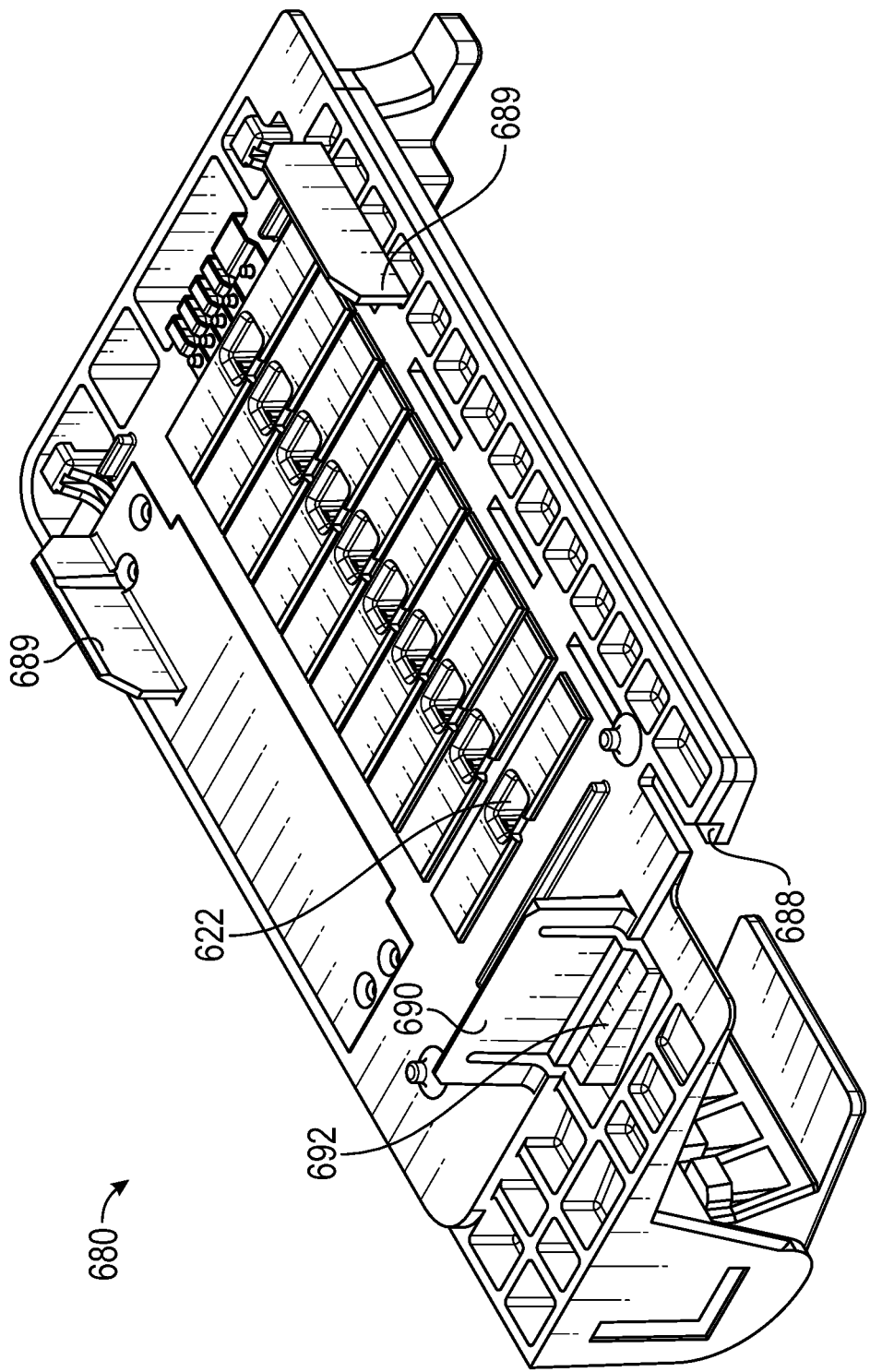
Figure 4E:
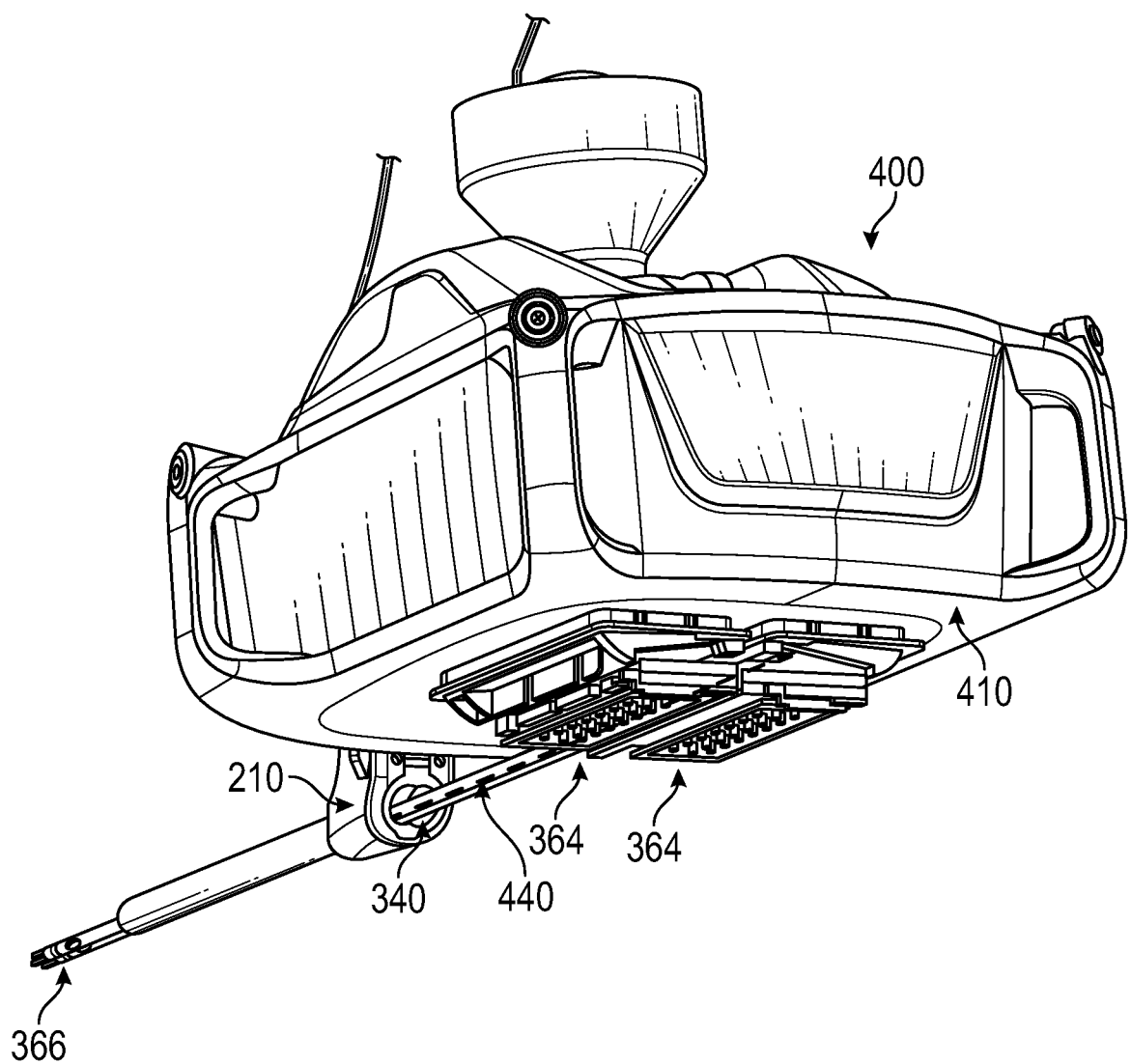

As shown in FIG. 2F, bottom surface 410 of the central unit 400 can include one or more instrument interfaces 420 configured to support and actuate one or more surgical instruments (as illustrated, for example, in FIG. 4E). Each instrument interface 420 can include a plurality of actuators 422 configured to interface (for example, mate with) with a plurality of actuators of a surgical instrument attached to the instrument interface (for instance, the actuators 322 of the surgical instrument illustrated in FIGS. 4G-4H). For example, the protrusion of the actuator 422 can interface with (such as mate with) the opening in an actuator 322 of the surgical instrument (sometimes referred to as surgical instrument actuator). Movement of the actuators 422, such as movement left and down (or up and down, or otherwise from one point to another point), can cause corresponding movement of the actuators of the surgical instrument. This can cause an end effector portion of the instrument (which can be located at the distal end of the instrument) to articulate or move (for example, in three dimensions), change orientation (for example, in three dimensions including rotation), and/or actuate or perform a function (such as, open or close a jaw of a grasper) as needed for performing the medical procedure.

To maintain sterility of the one or more surgical instruments, one or more sterile interfaces 680 (sometimes referred to as covers, interfaces, shields, or adapters) can be attached to or positioned on the instrument interfaces 420 that may not be sterile (for example, due to particular difficulty of sterilizing the plurality of actuators 422). As described herein, one or more sterile adapters 680 can be removably attached to the instrument interfaces 420, and an instrument can be placed or positioned in contact with the sterile adapter(s) 680 when mounted on the instrument interfaces 420. For example, when a single sterile adapter 680 is used to attach to the instrument interfaces 420, the sterile adapter can be configured to (for example, sized and shaped) to coincide or substantially coincide with the size and shape of the instrument interfaces 420. Sterile adapter 680 can have the same or substantially similar length and width as the instrument interface 420.

With reference to FIGS. 4A and 4D, the sterile adapter 680 can include a plurality of actuator covers 622 corresponding in size and shape to the plurality of actuators 422. The plurality of actuators 422 can be covered by the actuator covers 622 (for example, enclosed by or received in the actuator covers 622). Actuators covers 622 are also illustrated in FIG. 8N (which illustrates the adapter 680 in a perspective bottom view).

Although the actuators 422 are illustrated as protrusions (such as, a male connector), in some cases, one or more actuators 422 can include an opening or slot (such as, a female connector) configured to (for example, sized and shaped) to receive a protrusion of a corresponding surgical instrument actuator. In such cases, one or more actuator covers 622 can be configured to (for example, sized and shaped) to correspond to the size and shape of the actuators 422. Additional details of mounting and actuating a surgical instrument are disclosed in U.S. Pat. No. 9,629,688, the entire disclosure of which is incorporated by reference and should be considered part of this specification.

Figure 2G:
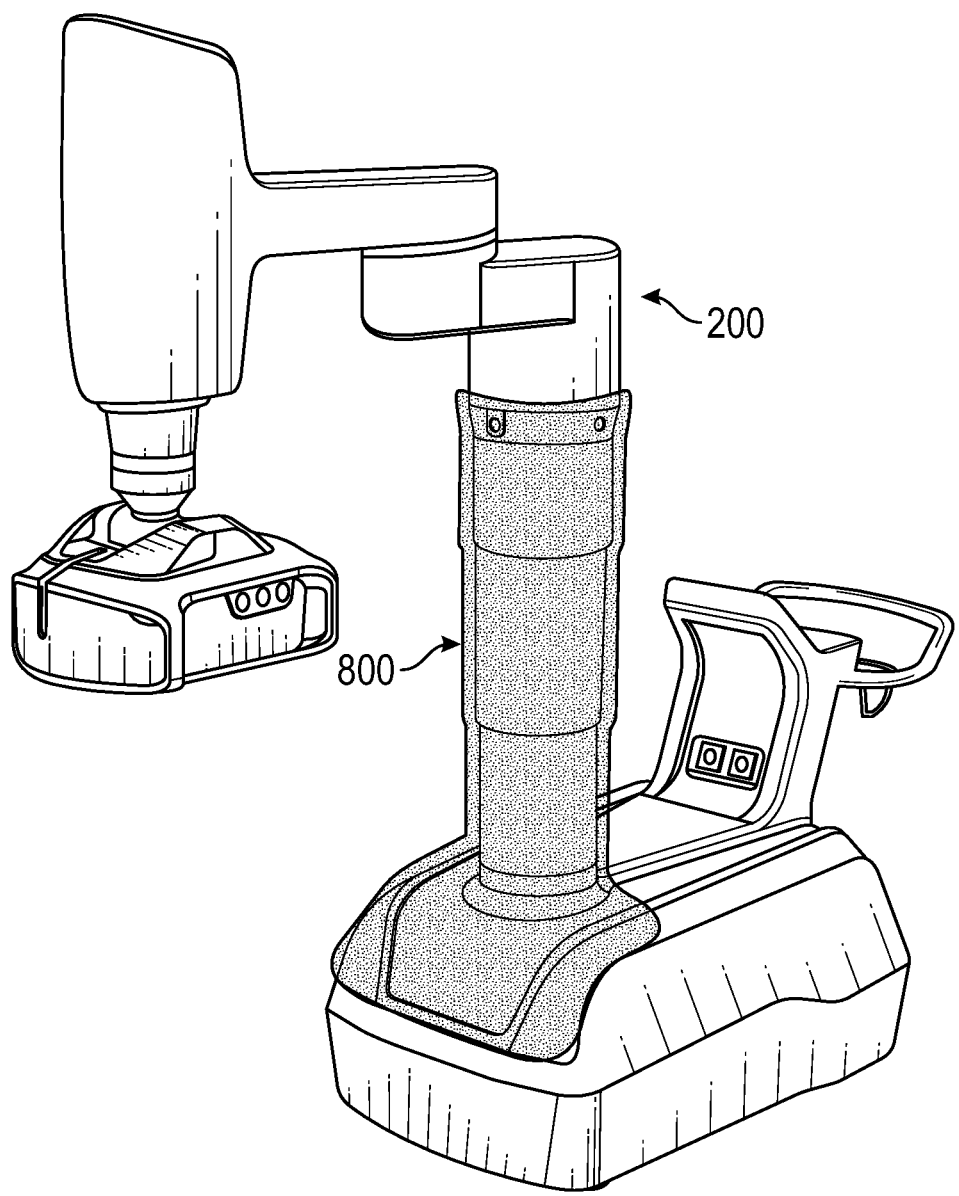

FIG. 2G illustrates covering a portion (or entirety) of the column 200 with a sterile barrier, illustrated as a drape 800. The drape 800 can facilitate maintaining sterility of sterile barrier of the central unit 400 (such as, the drapes 600 and 700) in case the central unit 400 is moved to come into contact with the column 200 (or another sterile object or person comes into contact with the column 200). As described herein, the drape 800 can be removably attached to the column 200 in one or more different positions or orientations. This can facilitate protecting the column 200 from coming into contact with blood, fluids, tissue, or the like during the medical procedure.

Sterile Barrier for Central Unit

Figure 3A:
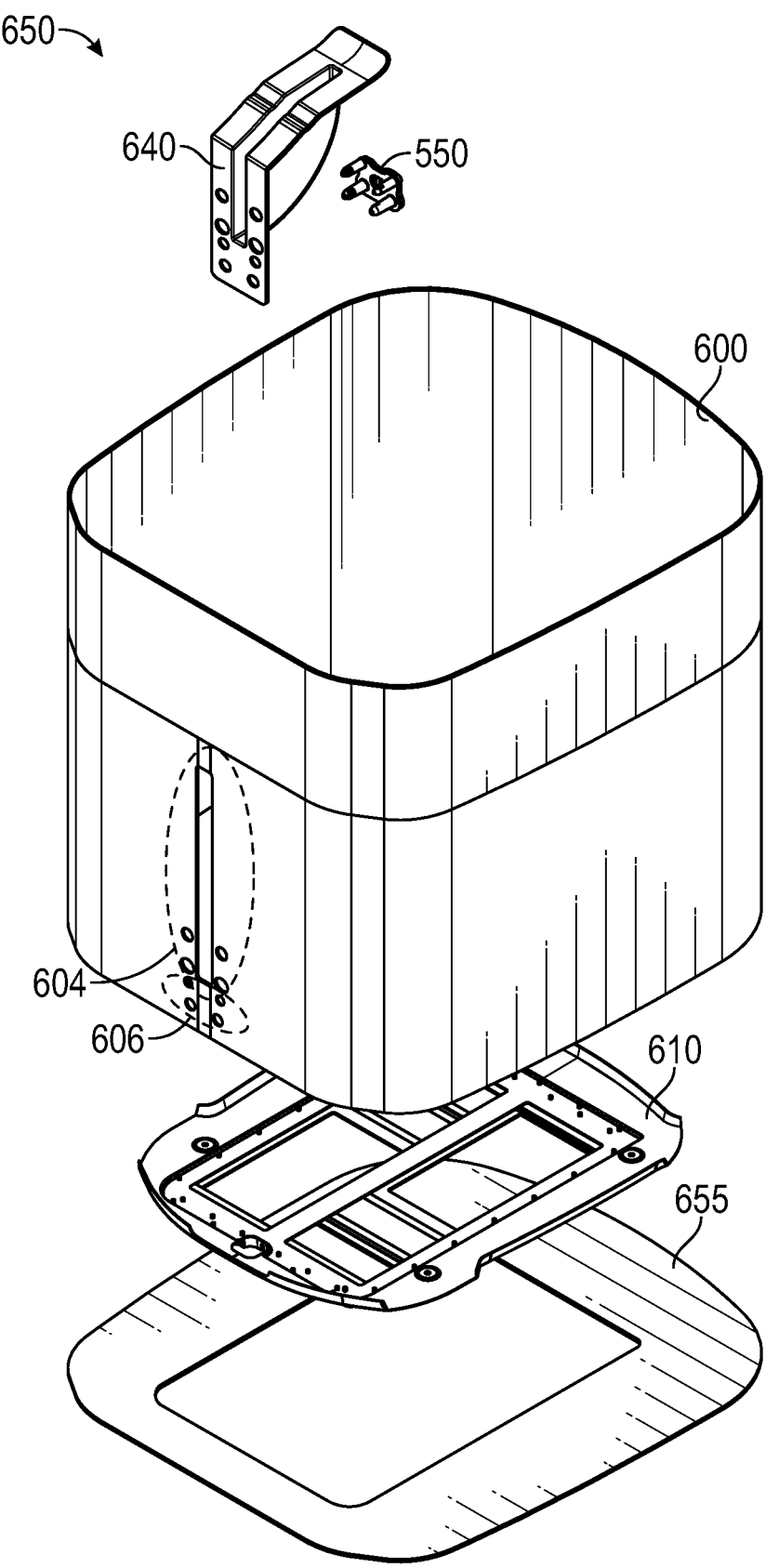
FIGS. 3A-3F illustrate a sterile barrier for a manipulator unit of the robotic surgery system.

FIG. 3A illustrates the sterile barrier 650 for the central unit. The sterile barrier 650 can include the drape 600 and the drape coupler 610 (which can be sometimes be referred to as tray). Both the drape 600 and the drape coupler 610 can be sterile. As described herein, the drape coupler 610 can be removably attached to at least one surface, for example the bottom surface 410, of the central unit 400. The drape coupler 610 can be configured to (for example, sized and shaped) to match the size and shape of the bottom surface 410 of the central unit 400. The drape coupler 610 can be rigid or substantially rigid. The drape coupler 610 can include one or more rigid or substantially rigid materials, such as plastic, metal, or the like.

Figure 3B:
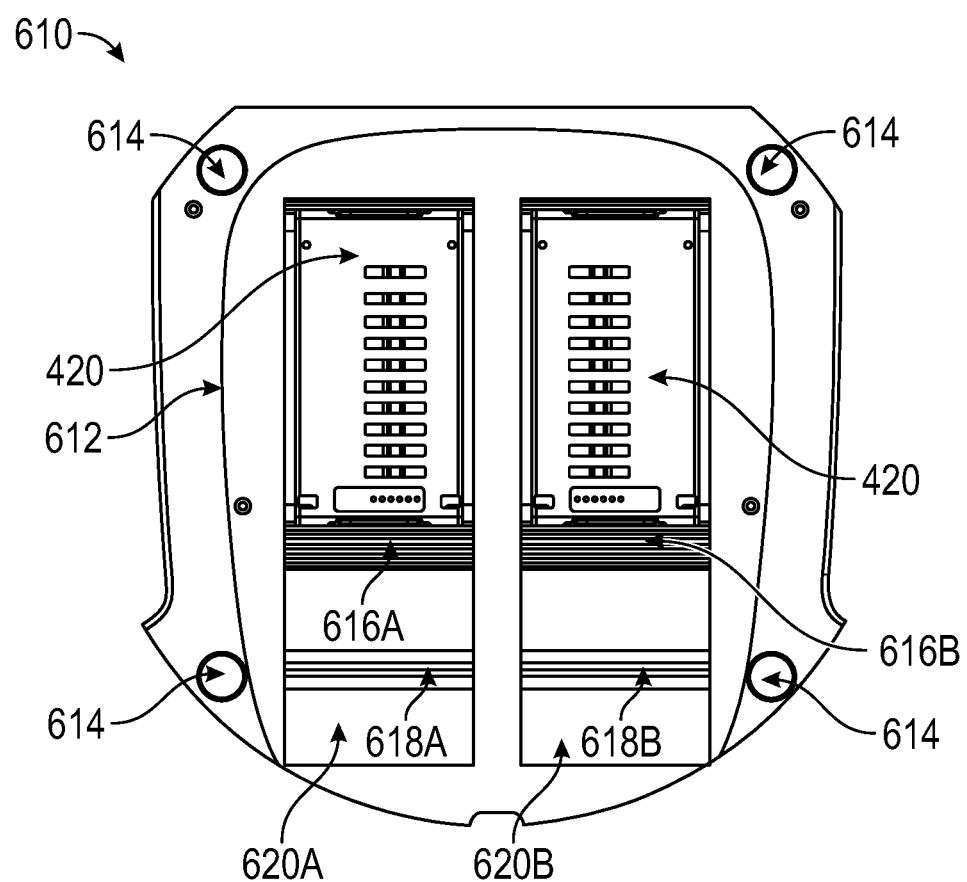

The drape 600 can be flexible or substantially flexible. The drape can include one or more flexible or substantially flexible materials, such as polyethylene (PE) (for example, low density polyethylene), polyurethane (PU), polyvinyl chloride (PVC), or the like. Although shown as separate components in FIG. 3A, the drape coupler 610 and the drape 600 can be attached to, or otherwise integrated with, each other. For example, the drape 600 can be attached to the drape coupler 610 along a perimeter of the drape coupler. With reference to FIG. 3B, in some cases, the drape 600 can be attached along a perimeter outlined by 612. For instance, the drape 600 can be adhered to portions of the drape coupler 610 that are positioned between the edges and the perimeter outlined by 612. The drape coupler 610 can facilitate covering (for instance, enclosing) the central unit 400 with the drape 600 due to, for example, preventing the drape (which can be flexible) from collapsing, keeping the drape in a position around the perimeter of the central unit, or the like (see, for example, FIGS. 8B and 8C).

Figure 3C:
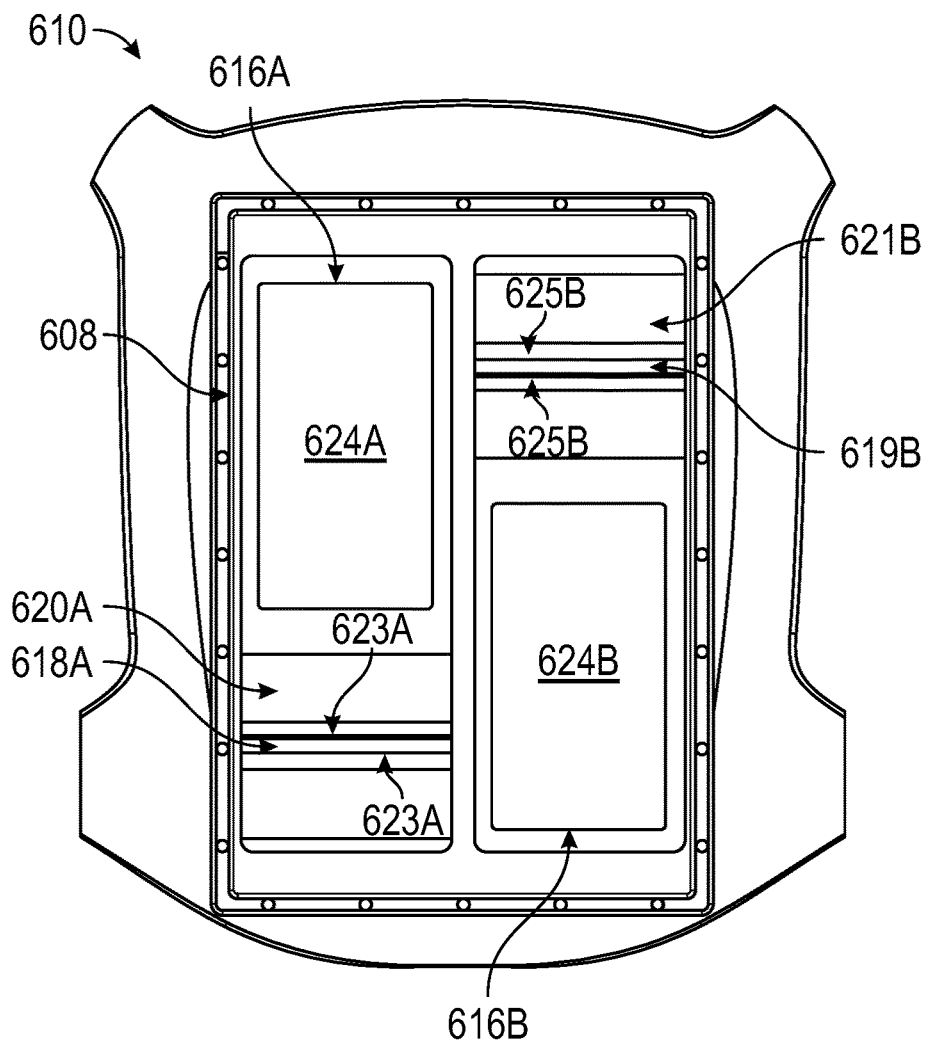

The cover 550 illustrated in FIG. 3A can be integrated into the sterile barrier 650. For example, the cover 550 can be attached to the drape 600, such as in the region 606 (see also FIG. 3D). For instance, the cover 550 can be attached through the openings or holes illustrated in the region 606 (such as, four holes). This is shown in FIGS. 3E-3F, which illustrate the sterile barrier 650 in a perspective front view and perspective bottom view, respectively. The attachment can be by adhesive, heat sealing, or the like.

An insert 640 (which can be sometimes be referred to as shell) can be positioned in the slit 504 of the central unit 400. The insert 640 can be have concave shape matching in size and shape the slit 504. The insert 640 can have side surfaces connected at one end (such as, at the bottom) and not connected at the opposite end (such as, at the top) to form an opening. As described herein, the looped portion of the primary camera tube 225 can be positioned in the slit 504. The slit 504 can be covered by the insert 640, and the looped portion of the primary camera tube 225 can be positioned in the insert 640. The insert 640 can be rigid or substantially rigid, which can facilitate the insert remaining inside the slit 504. The insert can include one or more materials that are more rigid than the one or more materials of the drape. For example, the insert 640 can include one or more plastic materials, such as high-density polyethylene (HDPE), acrylonitrile butadiene styrene (ABS), metal, or the like.

The insert 640 can be integrated into the sterile barrier 650. For example, as illustrated in FIGS. 3E-3F, the insert 640 can be attached to the drape 600, such as in the region 604 (see also FIG. 3D). The attachment can be by adhesive, heat sealing, or the like.

The cover 550 can include one or more rigid or substantially rigid materials, such as any of the materials described herein. For example, the cover 550 can include one or more plastic materials. The one or more materials of the cover 550 can be more rigid than the one or more materials of the insert 640. This can be due to the cover 550 providing support for the insertion device 210 and/or visualization device 220, and the insert 640 being substantially flexible to facilitate insertion into the slit 504.

FIG. 3B illustrates the drape coupler 610 as viewed from the side that is configured to face the bottom surface 410 of the central unit 400 (for example, inner facing side or upper surface of the tray illustrated in FIG. 3A). The drape coupler 610 can include one or more attachments or fasteners 614 configured to facilitate mounting of the drape coupler 610 to the bottom surface 410 of the central unit 400. The drape coupler 610 can be removably mounted to the bottom surface 410. In some cases, the fasteners 614 can include metal (or another ferromagnetic material) for attachment to the one or more attachments or fasteners positioned on the bottom surface 410 (which can be similar to one or more of fasteners illustrated in FIGS. 1B-1C). For instance, the fasteners 614 can be metal washers, and the one or more fasteners positioned on the bottom surface 410 can include magnetic material. The bottom surface 410 can include the same number of fasteners as on the drape coupler 610 (for example, four) to help facilitate the correct alignment between the drape coupler and the bottom surface of the central unit 400.

Instrument interfaces 420 of the central unit 400 (and attached surgical instrument(s)) can be configured to move (such as, linearly) toward and away from the site of interest (such as, the surgical site). For example, after a surgical instrument is mounted to the respective instrument interface 420 (using, for instance, a sterile adapter 680), the instrument may need to be advanced forward into the surgical site. To accomplish such movement, the instrument interface 420 can slide forward along one or more grooves on the bottom surface 410 (see, for example, FIG. 2F), which can cause the surgical instrument to correspondingly advance forward. When the surgical instrument may need to be repositioned or removed, the surgical instrument may need to be retracted away from the surgical site. To accomplish such movement, the instrument interface 420 can slide backward along the one or more groves (such as, into position illustrated, for example, in FIG. 2F), which can cause the surgical instrument to correspondingly retract away from the surgical site.

As shown in FIG. 3B, the drape coupler 610 can include one or more openings (sometimes referred to as windows) to expose the one or more instrument interfaces 420 of the central unit 400. The openings, which are also illustrated as 624A and 624B in FIG. 3C, can be moveable to facilitate movement of the one or more instrument interfaces 420 as described herein. To maintain sterility of the one or more surgical instruments (such as, preventing any part of a surgical instrument from coming into contact with the non-sterile bottom surface 410 of the central unit 400), the openings can include fixtures or frames 616A and 616B, which can slide forward and backward within slots or grooves of the drape coupler 610. The frames 616A and 616B can be rigid or substantially rigid. The frames can include rigid or substantially rigid material, which can include any one or more of rigid or substantially rigid materials described herein. The groves for facilitating movement of the frames 616A and 616B can be formed, for example, by a structure 608 (illustrated in FIG. 3C as a frame) positioned on the opposite side of the drape coupler 610 than that in FIG. 3B. The frame 608 can include any one or more of rigid or substantially rigid materials described herein. The groves can be formed between the frame 608 and another frame positioned on the inner facing side of the tray 610 shown in FIG. 3B. Another frame can be rigid (for instance, include any one or more of rigid or substantially rigid materials described herein).

One or more of the windows (624A and 624B) or the frames (616A and 616B) can be configured to (for example, sized and shaped) to match the size and shape of the instrument interfaces 420. The windows can have the same of substantially similar length and width as the corresponding instrument interfaces 420.

The frames 616A and 616B can be attached to or connected to one or more flexible or substantially flexible regions or sections 620A and 620B, which can include any of the flexible or substantially flexible materials described herein. The flexible sections can collapse and/or expand when the openings are moved, for example, forward and/or backward. This can facilitate maintenance of the sterile barrier between the central unit 400 (such as, its bottom surface 410) and one or more surgical instruments. As illustrated in FIG. 3C, similar flexible sections (such as, section 621B) can be positioned and connected to the top of the frames 616A and 616B. In FIG. 3B, bottom flexible sections 620A and 620B are shown in an expanded position or configuration (such as, fully expanded configuration), while top sections are shown in a collapsed position or configuration (such as, fully collapsed configuration). Location (or position) of the openings shown in FIG. 3B can correspond to a default location for mounting the drape coupler 610 to the bottom surface 410 of the central unit 400. This location can correspond to default (or docked) position or location of the instrument interfaces 420 (such as, when the robotic surgery system is being prepared for the medical procedure). The openings, which are moveable, can be maintained in the default location by one or more removable fasteners attached, for example, to edges of the frames 616A and 616B and one or more surrounding surfaces of the drape coupler 610. For instance, adhesive tear tabs can be used as fasteners.

Bottom flexible sections 620A and 620B (and similar top sections) can include one or more dividers or inserts 618A and 618B, as shown. Such inserts can be rigid or substantially rigid. The inserts can include one or more materials that are more rigid than the one or more materials of the sections 620A and 620B, such as any of the rigid or substantially rigid materials described herein. The inserts 618A and 618B can facilitate expansion and collapse of the flexible sections 620A and 620B, respectively. The inserts 618A and 618B can be configured to allow one or more flexible portions of the sections 620A and 620B, respectively, to wrap around, fold or be received overlapping a respective section, when the sections 620A and 620B are being collapsed. One or more flexible portions of the sections 620A and 620B can wrap around or fold onto the respective insert 618A and 618B. As illustrated in FIG. 3C, the insert 618A can be tapered. For example, the insert 618A include one or more tapered sides or edges 623A. The insert 619B can be tapered. For example, the insert 619B can include one or more tapered sides or edges 625B. The sides or edges can be tapered toward the one or more flexible portions of the respective section 620A and 620B. Tapered shape of the one or more inserts 618A and 619B can facilitate wrapping or folding of the flexible material of the sections 620A and 620B, respectively, or facilitate respective sections overlapping one another, as the sections are being collapsed. For instance, tapered shaped can facilitate the flexible material edges to be lifted (or scooped up) and folded as the one or more sections 620A and 620B are being collapsed.

FIG. 3C illustrates the tray 610 viewed from the side opposite than that shown in FIG. 3B, such as from the outer facing side (or surface) of the tray. In FIG. 3C, the left opening 624A is illustrated in the same location as in FIG. 3B, while the right opening 624B is illustrated in a different location. The right opening 624B is illustrated as being moved down (which can correspond to forward movement of the right instrument interface 420 and mounted surgical instrument, causing the surgical instrument to move towards the site of interest). Bottom flexible section 620B on the right is illustrated in the collapsed configuration (such as, fully collapsed configuration). Top flexible section 621B is illustrated in the expanded configuration (such as, fully expanded configuration). The flexible section 621B can include an insert 619B, which can be similar to the inserts 618A and 618B described herein. A flexible section similar to 621B can be positioned adjacent to top portion of the left window 624A. This flexible section is shown in the collapsed configuration (such as, fully collapsed configuration).

In some cases, when a particular flexible section is in a fully collapsed configuration, the opening is positioned at a maximum distance in which it is configured to move in that direction. For example, FIG. 3B illustrates the openings retracted to a maximum distance. As another example, FIG. 3C illustrates the opening 624B moved forward to a maximum distance. The maximum distances associated with movement of the openings 624A and 624B can correspond to range of movement of the instrument interfaces 420.

Although the illustrated central unit 400 and sterile barrier 650 are configured to facilitate attachment of two surgical instruments to the central unit, the central unit 400 and sterile barrier 650 can be configured to facilitate attachment of a single surgical instrument or more than two surgical instruments.

Any of the one or more windows (624A and 624B) can be covered by a cover (sometimes referred to as protector). The protector can be removable. For example, the protector can be attached or affixed to a bottom surface of the drape coupler 610 (see FIG. 3F). With reference to FIG. 3A, the protector 655 can be attached as shown. The protector 655 can cover the entire (or substantially entire) bottom surface of the drape coupler 610 or a portion of the surface. The protector can be attached, for instance, with adhesive. In some cases, the protector can include one or more sections that are independently removable. For example, the protector can include two sections covering the windows 624A and 624B.

Figure 3D:
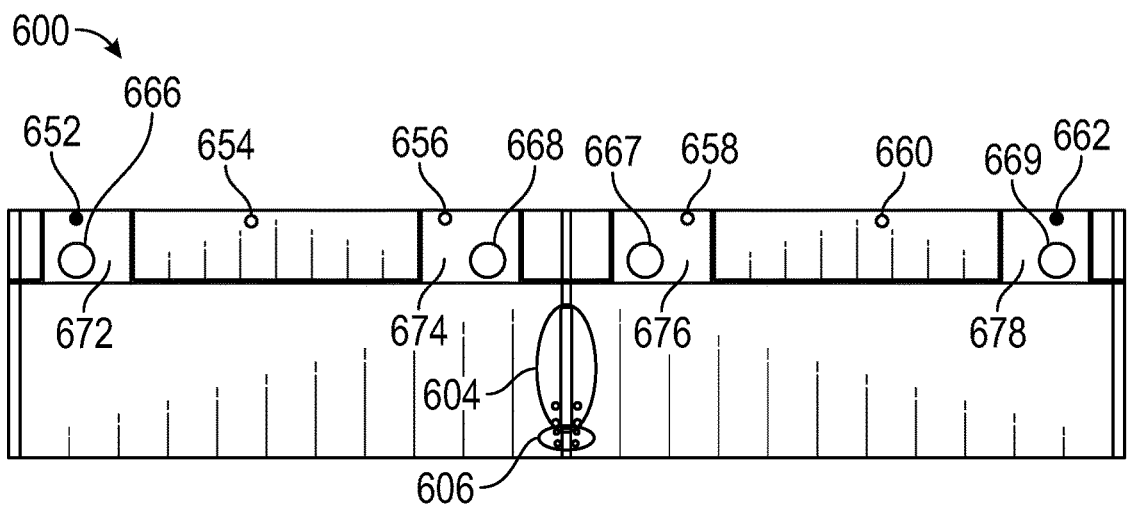
Figure 3E:
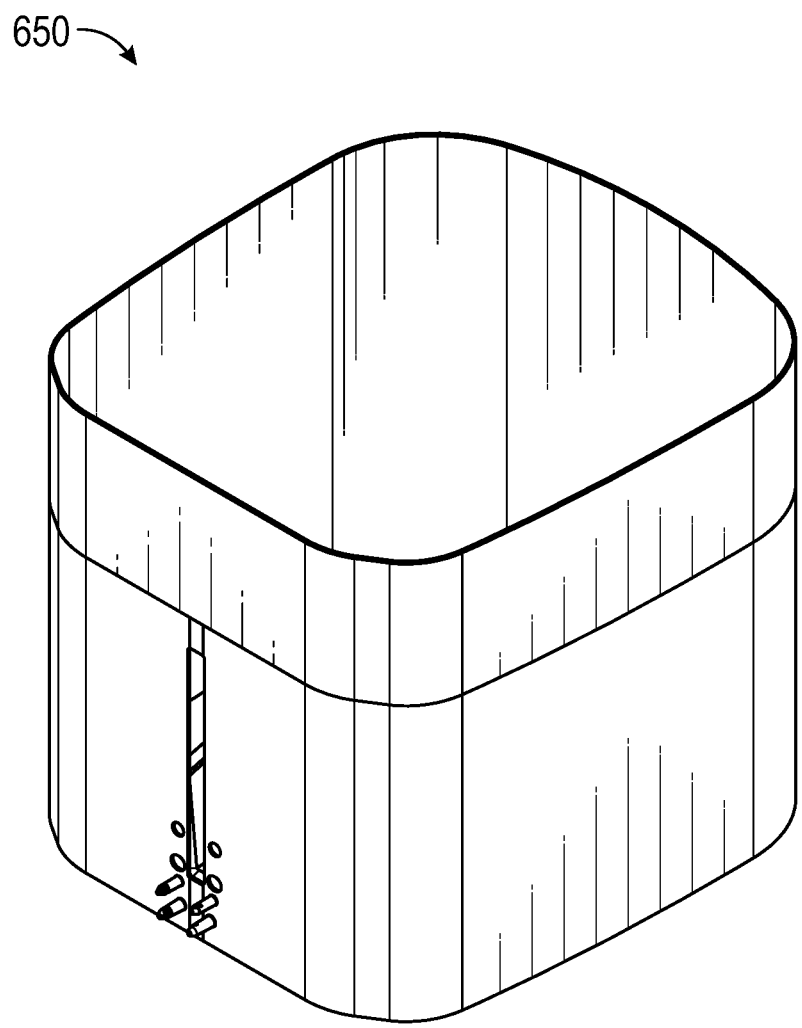
Figure 3F:
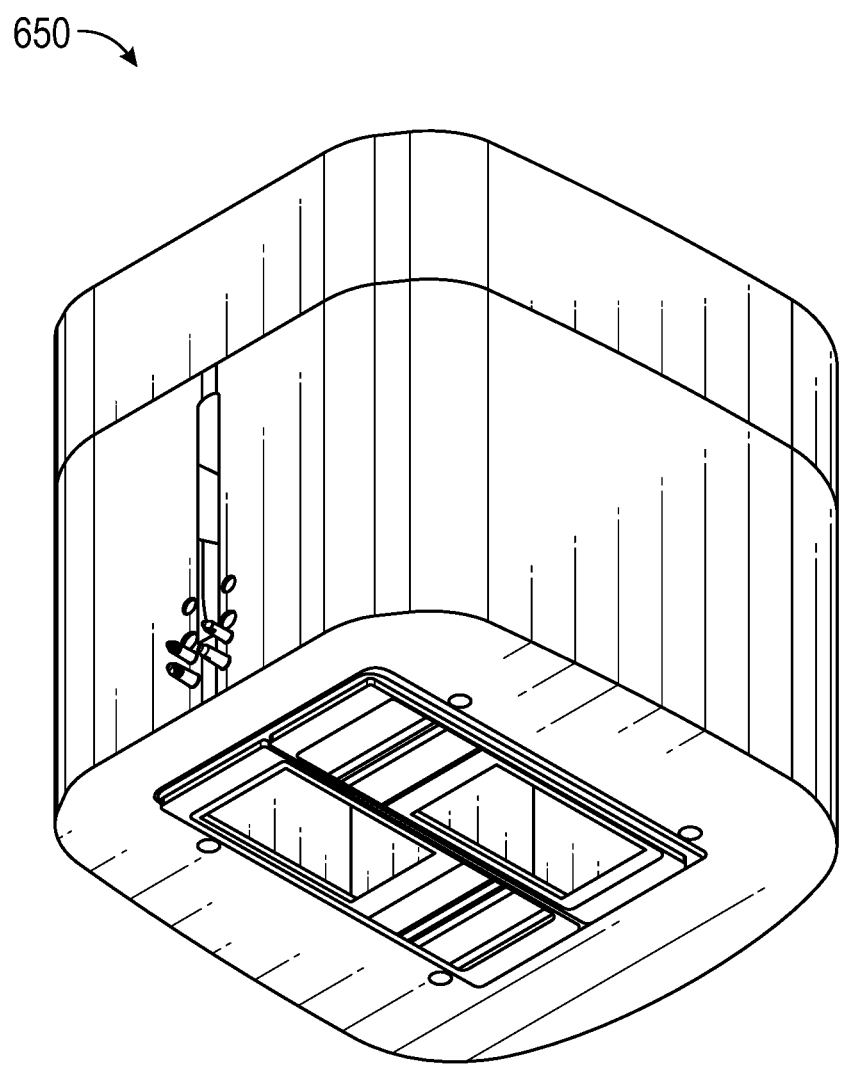

FIG. 3D illustrates the drape 600 in an unfolded configuration. The drape 600 is illustrated as being detached from the drape coupler 610. As described herein, the drape 600 can be attached to the drape coupler 610, and in folded configuration to form an enclosure configured (for example, sized and shaped) to enclose the central unit 400 (see, for example, FIG. 3A). One or more dimension of the drape 600 can correspond to (or be greater than) the one or more dimensions of the central unit 400.

The drape 600 can include one or more compartments (sometimes referred to as a pouches or pockets) illustrated as 672, 674, 676, and 678. An outer surface of the drape 600 (sometimes referred to as an outer side, outer facing surface, or outer facing side) can be configured to remain sterile during the medical procedure. The opposite inner side of the drape 600 (sometimes referred to as an inner side, inner facing surface, or inner facing side) can come into contact with one or more non-sterile surfaces of the central unit 400, and therefore may not remain sterile (even though the entire sterile barrier 650 may be sterile when packaged). The pockets can help maintain sterility of the outer surface of the drape 600 when a user, such as sterile nurse (for example, scrub nurse), covers the central unit 400 with the drape 600. For example, the pockets can prevent the user's hand from touching any non-sterile surface when the drape is being attached or affixed to the central unit 400. Any of the pockets described herein can facilitate maintaining sterility of a sterile barrier being attached to cover a component of the robotic surgery system.

Any of the pockets can be configured (such as, sized and shaped) to at least partially enclose the user's hand or part of the user's hand (such as, a finger or multiple fingers). One or more of the pockets 672, 674, 676, and 678 can be positioned on an outer surface of the drape 600 (or, in some cases, on the inner facing surface of the drape). Any of the pockets described herein can be formed by attaching a flexible or substantially flexible material to the drape, such as by heat sealing, adhering, or the like, or by causing a portion of the drape material to be folded and then heat sealing certain portions to form one or more pockets, with regions of the folded drape not requiring a pocket or enclosure being optionally removed. The material attached to the drape can be the same or similar to the one or more materials of the drape, which can be any of the flexible materials described herein. One or more of the pockets 672, 674, 676, and 678 can be configured to enclose a user's hand.

The pockets can be labeled, for example, with labels 666, 667, 668, and 669, respectively. Any of the labels can include an indication (or indicia) of which hand (left or right) or portion of the hand should be inserted into the pocket. For example, as illustrated in FIG. 7B, label 910 can guide the user to insert the right hand into the pocket and label 912 can guide the user to insert the left hand into the pocket. The hand shape in label 910 corresponds to the shape of the right hand (with the thumb being on the left side when palm of the right hand faces the page). The hand shape in label 912 corresponds to the shape of the left hand (with the thumb being on the right side when palm of the left hand faces the page). Any of the labels can additionally or alternatively guide the user in which direction to insert a particular hand. With reference to FIG. 7B, label 912 can guide the user to insert the right hand with the palm facing the central unit 400, as this orientation of the right hand would match the outline of the right hand depicted in the label (such as, when the label is attached to the interior front or rear surface of the pocket, which can be positioned on the outer facing surface of the drape). Similarly, label 912 can guide the user to insert the left hand with the palm facing the central unit 400, as this orientation of the left hand would match the outline of the left hand depicted in the label (such as, when the label is attached to the rear surface of the pocket). Any of the labels described herein can be attached to the interior or exterior surfaces of the pocket and/or other surfaces of the drape.

In some cases, labels 666 and 667 can guide the user to insert the right hand, and labels 668 and 669 can guide the user to insert the left hand. The pockets can be paired depending on a step of the process for covering the central unit 400 with the drape 600. When two pockets are paired, the user may insert right and left hands into respective pockets of the pair to perform the particular step. The labels can provide indication of the pairing. For example, as illustrated in FIG. 7C, labels 920 (right hand) and 922 (left hand) include the number "1" indicating pairing of the two labels. Indication of the pairing may also correspond to the order of the process. For example, the number "1" can indicate an earlier (such as, first step) in the process than one or more labels with subsequent numbers, such as "2," "3," or the like. In some cases, letters, images, or the like can be used instead of or in addition to the numbers.

The drape 600 can include one or more attachments or fasteners 652 and 662. Fastener 652 can be positioned in a region of the drape covered by (or overlaps with) the pocket 672. Fastener 662 can be positioned in a region of the drape covered by the pocket 678. As described herein, one or more of the fasteners 652 and 662 can include ferromagnetic material, such as a metal washer, configured to be attached to an attachment or fastener of the central unit, such as one or more of fasteners 302 and 304 (for example, by being brought into contact or into proximity of the one or more fasteners 302 and 304). Any of the fasteners 652 and 662 can be positioned on or adjacent to the inner facing surface of the drape 600, which is configured to come into contact with the central unit 400.

In some cases, pockets 672 and 678 can be paired. For example, labels 666 and 669 associated with the pockets 652 and 662, respectively, can correspond to labels 920 and 922 illustrated in FIG. 7C. As shown in FIGS. 8B-8D, the user can be guided to insert the right hand into the pocket 672 and left hand into the pocket 678 (or vice versa). The drape 600 can subsequently be lifted and attached to the central unit 400 (for example, by forming a magnetic attachment between the fasteners 652 and 662 and fasteners 302 and 304). The pockets 672 and 678 can facilitate maintaining sterility of the outer facing surface of the drape 600 when the drape is being attached to the central unit 400. When the drape 600 is in the folded configuration as illustrated in FIG. 3A, the pockets 672 and 678 can be positioned adjacent to each other (see, for example, FIGS. 8B-8D).

The drape 600 can include attachments or fasteners 654, 656, 658, and 660, which may not be attached to the central unit 400. The drape can include fasteners similar to the fasteners 654, 656, 658, and 660 positioned in the same or similar region as the previously described fasteners 652 and 662 (which, as described herein, can be attached to fasteners of the central unit 400). For example, the fasteners 652 and 662 can be positioned on or adjacent to the inner facing surface of the drape, while the other fasteners can be positioned on or adjacent to the opposite exterior facing surface of the drape (such as, on an exterior surface of the pockets 672 and 678). Because regions illustrated as 652 and 662 can include multiple fasteners, for simplicity, the fasteners positioned in the same or similar region as the previously described fasteners 652 and 662 can be referred to as second fasteners 652 and 662. Fasteners 654, 656, 658, and 660 as well as the second fasteners 652 and 662 can facilitate covering (such as, enclosing) the central unit with the drape 600 and maintaining the drape in the desired position during the medical procedure. These fasteners can be attached (or connected) to one another as described herein. Any of these fasteners can provide removable attachment and can include one or more of a hook-and-loop fastener (for example, a VELCRO® Brand fastener), adhesive fastener, button fastener, magnetic fastener, zippers, or the like.

Second fasteners 652 and 662 can be positioned in regions of the drape covered by pockets 672 and 678, respectively. As described herein, second fasteners 652 and 662 can be paired (or configured for being attached to), for instance, to fasteners 656 and 658, respectively. Second fasteners 652 and 662 can be removably attached of affixed to fasteners 656 and 658, respectively. In some cases, second fasteners 652 and 662 can be VELCRO fasteners.

In some cases, pockets 674 and 676 can be paired. For example, labels 668 and 667 associated with the pockets 674 and 676, respectively, can correspond to labels 922 and 920 illustrated in FIG. 7C (with the exception of replacing the number "1" in both labels with, for instance, the number "2" indicating a step subsequent to that indicated by the number "1"). The user can be guided to insert the right hand into the pocket 676 and left hand into the pocket 674 (or vice versa). Fastener 656 can be positioned in a region of the drape 600 covered by the pocket 674. Fastener 658 can be positioned in a region of the drape 600 covered by the pocket 676. Fastener 656 can be paired with or connected to the second fastener 652. Fastener 658 can be paired with or connected to the second fastener 662. As illustrated in FIGS. 8E-8F, fastener 656 can be removably attached to the second fastener 652, and fastener 658 can be attached to the second fastener 662. In some cases, fasteners 656 and 658 can be VELCRO fasteners. The pockets 674 and 676 can facilitate maintaining sterility of the outer facing surface of the drape 600 when the user is attaching the fasteners 656 and 658 to the second fasteners 652 and 662, respectively. As illustrated in FIG. 3A, the pockets 674 and 676 can be positioned adjacent to each other (see also, for example, FIGS. 8E-8F). The pockets 674 and 676 can be positioned opposite the pockets 672 and 678 when the drape 600 is in the folded configuration (see, for example, FIGS. 8B-8F).

The drape 600 can include fasteners 654 and 660. These fasteners can be paired. The fasteners 654 and 660 can be attached to each other (for example, removably attached) as illustrated in FIG. 8G. In some cases, fasteners 654 and 660 can be VELCRO fasteners. Fasteners 654 and 660 can be connected to each other to tighten the drape 600 around the central unit 400, as illustrated in FIG. 8G. For instance, fasteners 654 and 660 can be positioned in a portion of the drape 600 configured to cover a rear portion of the central unit 400. One or more pockets may not be needed to attach the fasteners 654 and 660, for example, due to a low or non-existent risk of the user touching, or otherwise coming into contact with, any non-sterile surface of the central unit 400. For instance, there may be folds on the outer facing surface of the drape where the fasteners 654 and 660 are positioned. The user can grab or pinch the folds to connect the fasteners 654 and 660 without the risk of touching any non-sterile surfaces of the central unit 400.

In FIG. 3D, all pockets and fasteners are illustrated as being positioned near the top edge of the drape. This positioning may be appropriate because the bottom side of the drape 600 can be attached to the drape coupler 610. As described herein, the drape coupler can be attached to the bottom surface 410 of the central unit 400, which may obviate the need to separately attach the bottom portion of the drape 600 to the central unit 400 (and thus include one or more pockets or fasteners). In some cases, any of the pockets, fasteners, or labels can be positioned in a different location (including on a different surface) or removed. Additional pockets, fasteners, or labels fasteners can be added.

Sterile Adapter for Surgical Instrument Interface

FIGS. 4A-4D illustrate the sterile adapter 680 in a front perspective view, side view, rear view, and top prospective view, respectively. The sterile adapter 680 (or multiple sterile adapters as shown in FIG. 2F) can be part of the sterile barrier 650 for the central unit 400. The adapter 680 can be attached to the instrument interface 420 and provide a sterile barrier between the instrument interface and a surgical instrument. The illustrated adapter 680 can be a sterile barrier for a left (see "L" on the front of the adapter as shown at 683) instrument interface 420 of the central unit 400 (see, for example, FIGS. 3B-3C). The right instrument interface 420 can be covered with a similar sterile adapter.

Figure 4F:
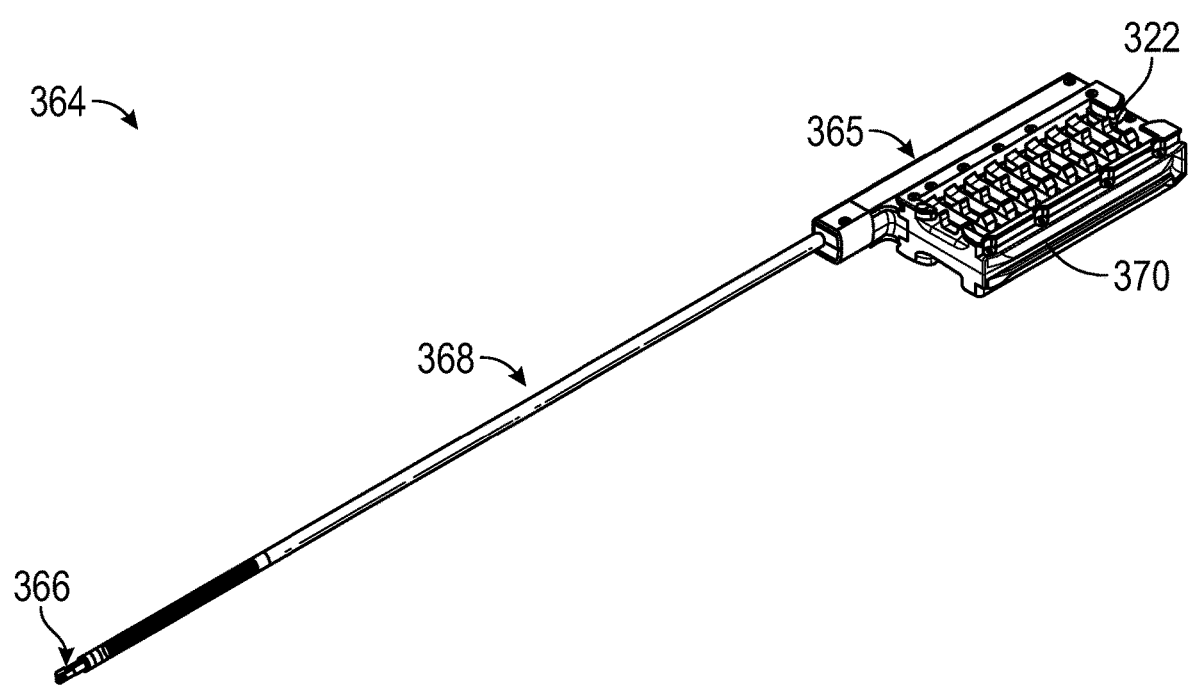
Figure 4G:
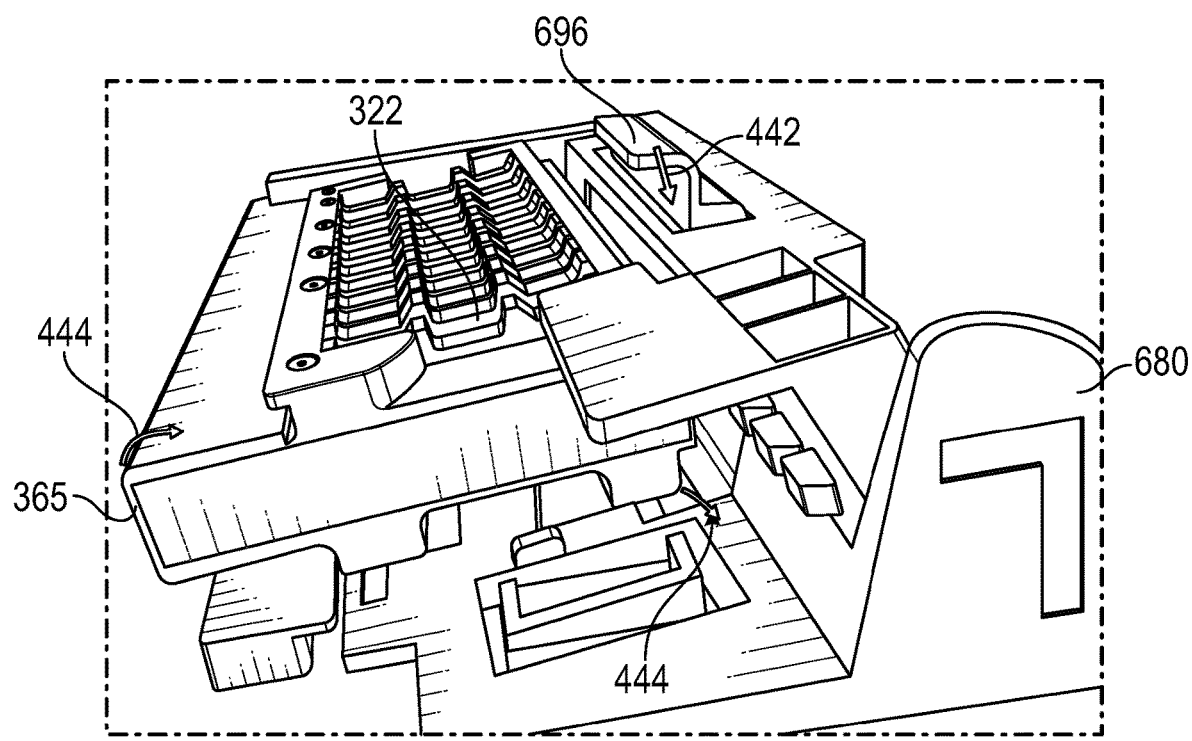
Figure 4H:
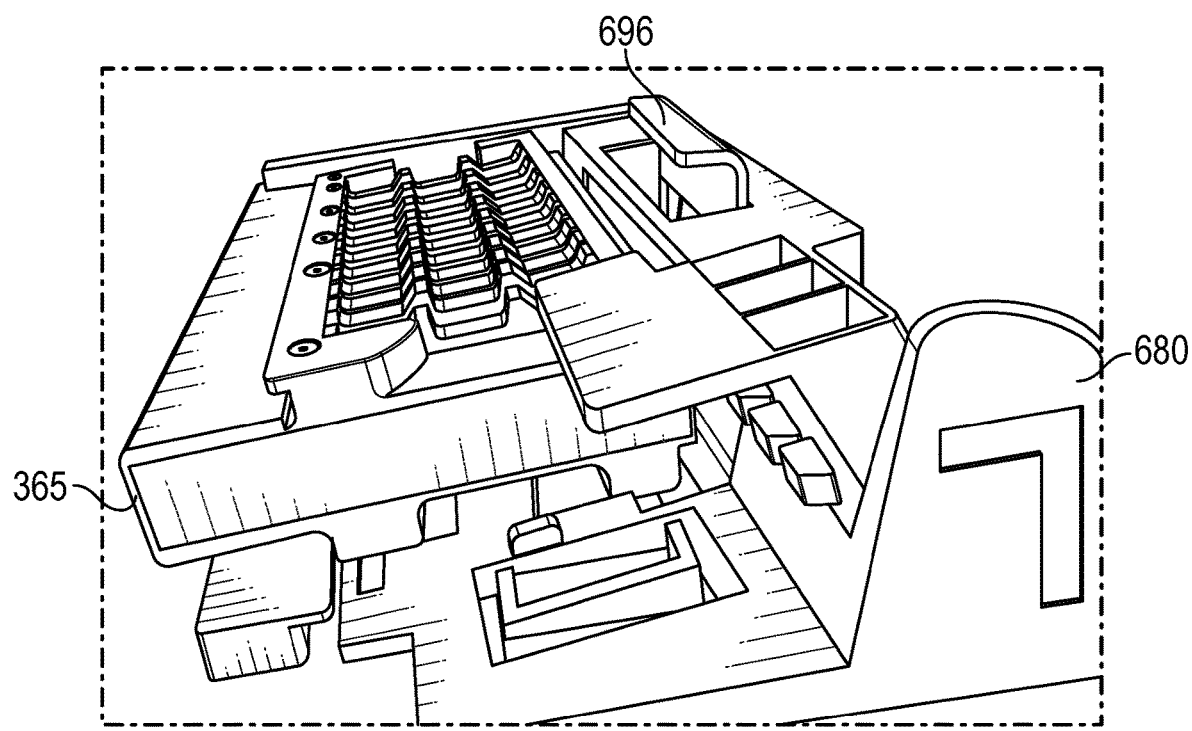

The adapter 680 can include a housing configured to support the surgical instrument (see, for example, FIGS. 4G-4H). The adapter 680 can be removably attached to the instrument interface. As is illustrated in FIG. 4A, a closure 690 can be configured to attach the adapter 680 (such as, the front portion of the adapter) to the instrument interface 420. As illustrated in FIG. 4D, the closure 690 can include a release mechanism (for example, a handle) 692. With reference to FIG. 8L, the closure 690 can be releasably attached to (or mate with) an opening 428 of the instrument interface 420. As shown in FIGS. 4B-4C and 8L, the closure 690 can include a protrusion or latch 691 configured (such as, sized and shaped) to be inserted into the opening 428 when the adapter 680 is being attached to the instrument interface 420. The latch 691 can be positioned on the back of the closure 690 (such as, on the back of or adjacent to the handle 692). The handle 692 can be moved or flexed to release the latch 691, which can cause disengagement of the latch 691 from the opening 428 in the instrument interface 420. For example, the user can pull on the handle 692 to release the adapter 680. In some cases, the user can push the handle 692 to release the adapter 680.

The latch 691 can include a plurality of latches. Such latches can be shorter and may not extend along the entire length of the closure 690 (see FIG. 4C). For example, two latches can be positioned on opposite sides of the closure 690. As another example, three latches can be positioned as follows: two on the opposite sides of the closure 690 and one in the middle of the closure 690. In some cases, there can be other combination and/or positioning of the latches.

As illustrated in FIGS. 4B-4D, the adapter 680 can include one or more protrusions 682 (sometimes referred to as tabs or hooks) positioned on the opposite side (such as, a rear side) of the adapter 680 from the closure 690. The protrusions 682 can be configured to attach (such as, removably attach) the rear portion of the adapter 680 to the instrument interface 420. With reference to FIGS. 8K-8L, the protrusions 682 can be connected to the holes or openings 426 positioned in the rear portion of the instrument interface 420 (such as, in the direction illustrated by the arrows in FIG. 8K). The protrusions 682 can be shaped as hooks configured to attach to corresponding openings 426, as shown by the arrows in FIG. 8K. The protrusions 682 can make contact with (such as, hook onto) the surface of the openings 426 (such as, edges of the openings). Such attachment can be removable as the moving the adapter 680 down (such as, at an angle) can release the back portion of the adapter. FIG. 8M illustrates the adapter 680 affixed or attached to the instrument interface 420.

With reference to FIGS. 4D and 8K-8M, one or more protrusions or plates 689 on the sides of the adapter 680 can facilitate one or more of attachment to, removal from, and support of the adapter by the instrument interface 420. The plates 689 can contact side portions of the instrument interface 420 as illustrated in FIG. 8M.

As described herein, the adapter 680 can include a plurality of actuator covers 622 (see, for example, FIG. 4D) configured to receive a plurality of actuators 422 of the central unit 400. The actuator covers 622 can provide a sterile interface between the actuators 422 of the instrument interface 420 and the actuators of the surgical instrument, such as actuators 322 of a surgical instrument, such as the instrument 364 illustrated in FIG. 4F. Movement of the actuators 422 can be transferred through the actuator covers 622, which can be configured to move with the actuators 422 (for instance, left and right), to the actuators 322 of the surgical instrument. This can cause the end effector portion of the instrument, such as the end effector 366 of the instrument 364 illustrated in FIG. 4F, to articulate or move.

It may be advantageous to facilitate removal of the surgical instrument(s) 364 from the site of interest in case of malfunction of the robotic surgery system (or any of its components), loss of power, emergency, or the like. The actuator covers 622 are illustrated in FIGS. 4A-4D as being positioned or aligned (such as, centrally aligned), which can correspond to the default position or alignment of the actuators 422 (such as, for loading the surgical instrument; see, for example, FIG. 8L). During the performing of the medical procedure, the actuators 422 (and actuator covers 622), which can be configured to move independently of one another, may no longer be in the default (aligned) position due to manipulation of the end effector portion of the surgical instrument. Because of the misalignment, it may not be possible to remove the surgical instrument by simply pulling out the instrument from the sterile adapter 680. The sterile adapter 680 can be configured to allow the surgical instrument to be removed when the robotic surgery system is in use by rotating the surgical instrument to disengage the actuators 322 of the surgical instrument from the actuators 422 covered by the actuator covers 622. Such design can promote safety, simplicity, and efficiency, among other advantages.

With reference to FIGS. 4A and 4B, the adapter 680 can include a groove or guide 684 (sometimes referred to as a slot) configured (such as, sized and shaped) to receive a housing of a surgical instrument (see, for example, FIGS. 4F-4H). The guide 684 can be of a width 686 that matches the width of the surgical instrument housing (for example, housing 365, which is shaped as a rectangular cassette, as shown in FIGS. 4F-4H). The guide 684 can facilitate loading (or removal) of the surgical instrument housing. The guide 684 can include a protrusion 687 (such as, a rib or rail) configured (such as, sized and shaped) to guide the surgical instrument housing into the adapter 680. The surgical instrument housing can include an opening or groove, such as, the groove 370 illustrated in FIG. 4G, configured to receive the protrusion. The groove can be positioned on the side of the housing of the surgical instrument (such as, the left side for the left instrument, as illustrated in FIG. 4F).

The guide 684 can be configured to guide the surgical instrument housing into the adapter 680. As illustrated in FIG. 4A, the guide 684 can be oriented at an angle relative to the horizontal plane, in which the actuators 422 and actuator covers 622 can be oriented. The plane of the guide 684 can be tilted relative to the plane of the actuator covers 622. This can facilitate loading (or removing) the surgical instrument housing at an angle. The angle can be 5 degrees (or less or more), 8 degrees, 10 degrees (or less or more), 12 degrees (or less or more), 15 degrees (or less or more), 20 degrees (or less or more), or the like. The angle can be less than 5 degrees or more than 20 degrees. When the surgical instrument is loaded through the guide 684, the surgical instrument actuators 322 may not be engaged with (or coupled to) the actuators 422 covered by the actuators covers 622.

The surgical instrument housing 365 may be rotated inside the adapter 680 in order to facilitate engagement of surgical instrument actuators 322 with the actuators 422 (covered by the actuator covers 622). As illustrated in FIGS. 4A-4B, a fastener 694 (sometimes referred to as a catch) can be configured to one or more of support the housing of the surgical instrument housing and to rotate the housing within the adapter 680. The fastener 694 can include a protrusion 695 (sometimes referred to as rib or rail) configured (such as, sized and shaped) to engage with the surgical instrument housing. For example, the rail 695 of the fastener 694 can engage with an opening or groove positioned on the side of the surgical instrument housing 365 (such as, the groove 370 illustrated in FIG. 4F). The rail 687 of the guide 684 and the rail 695 of the fastener 694 can be level or substantially level (see, for example, FIG. 4B), and the groove can be the same groove as described herein in connection with the rail 687.

The fastener 694 can include (such as, be connected to) a handle or lever 696. The user can move the lever in one or more directions, such as up and down. When the lever 696 is moved upward (for example, due to the user pushing the lever up), the fastener 694 and the rail 695 can move upward. This can cause the surgical instrument housing to rotate. For instance, the rotation can be due to the rail 695 being moved up and causing the side of the instrument on which the groove 370 is positioned to move up. In some cases, the lever 696 can be pulled down and/or to one of the sides to cause rotation of the surgical instrument housing 365.

With reference to FIG. 4G, the surgical instrument housing 365 is illustrated as being positioned in the adapter 680, which is shown positioned upside down. Unlike normal operation, the surgical instrument housing 365 is positioned upside down in the adapter to illustrate the actuators 322. The user can move the lever 696 down (or upward when the adapter 680 is correctly positioned), as illustrated by the arrow 442. This can cause the surgical instrument housing 365 to be rotated in the direction of the arrows 444. The rotation can be in clockwise direction. In some cases, the rotation can be in counterclockwise direction. Position of the rotated surgical instrument housing 365 is illustrated in FIG. 4H (which also shows the adapter and surgical instrument housing upside down).

The lever 696 can be locked into position so that the surgical instrument housing 365 remains in the rotated position, in which the surgical instrument actuators 322 are engaged with the actuators 422 (covered by the actuator covers 622). The lever can be locked into position (or unlocked during removal of the surgical instrument) by locking (or unlocking) a closure of the lever, such as a latch. The user can lock the lever 696 into position by, for instance, moving the lever 696 outward (or in a direction away from the adapter 680). Unlocking the lever 696 can be performed by moving the lever in the opposite direction.

With reference to FIG. 4E, central unit 400 is shown in a rear view with surgical instruments 364 attached to the instrument interfaces 420 (or loaded). With reference to FIG. 4F, the instrument 364 can include the surgical instrument housing 365, a shaft 368 connected to the housing, and an end effector 366 connected to the shaft. As illustrated in FIG. 4E, the shaft 368 and the end effector 366 can be loaded through an opening 340 formed in the rear of the housing 212 of the insertion device 210. The surgical instrument housing 365 can be rotated (or pivoted) about an axis 440 that traverses along a center of the shaft of the surgical instrument. The axis 440 can coincide with the axis that traverses along a center of the end effector 366. The surgical instrument housing 365 can be rotated about the axis that traverses along the center of the end effector 366. The axis 440 can coincide with the axis that traverses along a center of the opening 340 in the insertion device 210 through which the end effector and the shaft of the surgical instrument are inserted during loading. The surgical instrument housing 365 can be rotated about the axis that traverses along (or through) the center of the opening 340.

To load the surgical instrument 364, the user can move the surgical instrument housing 365 through the guide 684 (at an angle, as described herein). With reference to FIGS. 4B and 4F, the length 685 of the guide 684 can be shorter than the length of the surgical instrument housing 365. Once a portion (or entirety) of the surgical instrument housing 365 passes through the guide 684, it can engage with the rail 695, as described herein. In some cases, the surgical instrument housing 365 can engage with the slot 688 positioned at the top of the adapter 680, as shown in FIG. 4A. The surgical instrument housing 365 can be supported by one or more of the rail 695 or the slot 688. In some cases, as illustrated, the adapter 680 does not include a bottom. With reference to FIGS. 4B and 4F, the length 685 of the portion of the adapter that is adjacent to the guide 695 can be sufficient to receive the entire surgical instrument housing 365. The length 681 of the portion can match the length of the surgical instrument housing 365, such as be the same, substantially the same, or larger than the length of the surgical instrument housing. Once loaded, the surgical instrument housing 365 can be rotated (and, optionally, locked) into position, in which the surgical instrument actuators 322 are engaged with the actuators 422 (covered by the actuator covers 622).

As illustrated in FIGS. 4A-4D, the guide 684 can be positioned on or in a first side portion of the housing of the adapter 680. The fastener 694 (and the rail 695) can be positioned on or in a second side portion of the housing of the adapter 680. The first and second side portions can be positioned on the same side of the housing (for example, left side in case of an adapter for the left instrument). The first and second side portions may not be connected. For example, the first and second side portions can be separated by a gap as shown in FIG. 4B. In some cases, the guide 684 and fastener 694 can be positioned in the same side portion.

In some cases, any of the actuators 422 can be tapered as illustrated in FIGS. 8K-8L. The base (or proximal portion) of the respective actuator 422 can be wider than the end (or distal portion) of the actuator. Any of the actuator covers 622 can be similarly tapered. The tapered shape can facilitate engagement with the surgical instrument actuators 322 as the surgical instrument housing is being rotated.

To remove the instrument 364, the user can perform steps opposite to those performed during the unloading of the instrument. For example, the lever 696 can be unlocked. The latch can be unlocked (such as, by moving the lever 696 inward). This can cause the fastener 694 and the rail 695 to move downward, which causes the surgical instrument housing 365 to rotate. The surgical instrument actuators 322 can be disengaged from the actuators 422 (covered by the actuator covers 622). The instrument can be removed from the adapter 680.

The fastener 694 can include an elastic element, such as a spring. For example, the rail 695 can be biased by the elastic material or element into a position in which the surgical instrument housing 365 is not rotated (such as, downward position). To rotate the surgical instrument housing 365, the user can move the lever 696 upward, which can cause compression of the elastic material. When the user releases the lever 696, the elastic material can decompress causing the rail 695 to be moved downward. This can facilitate easier removal of the surgical instrument.

Figure 4I:
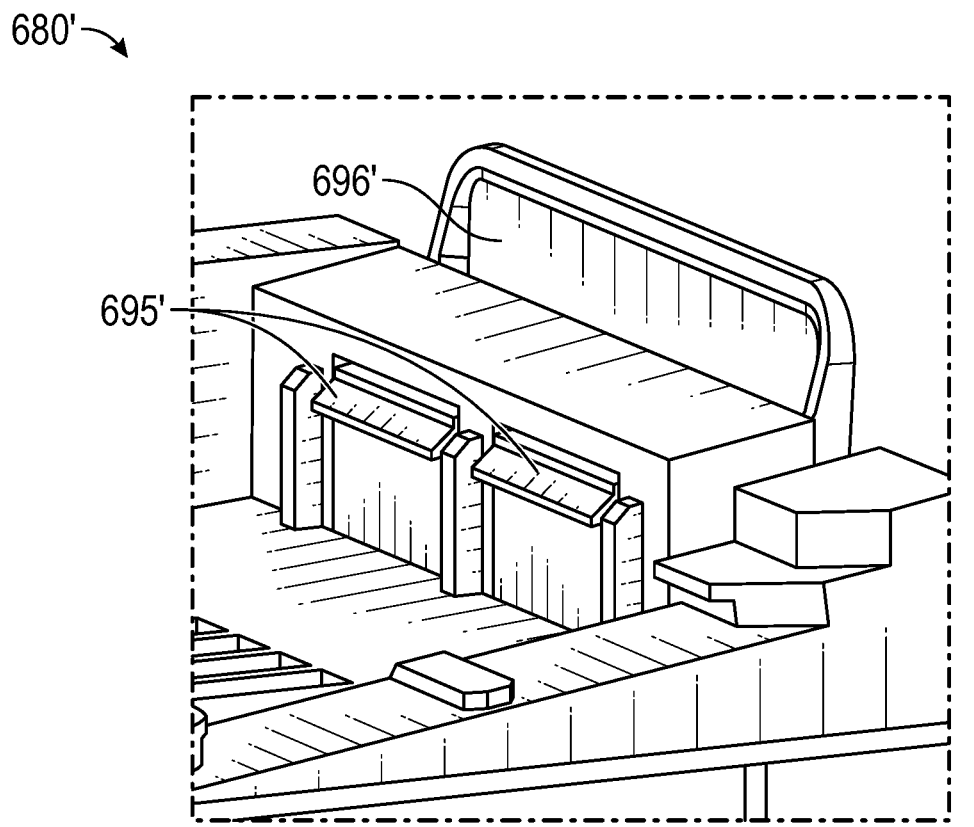
Figure 4I:
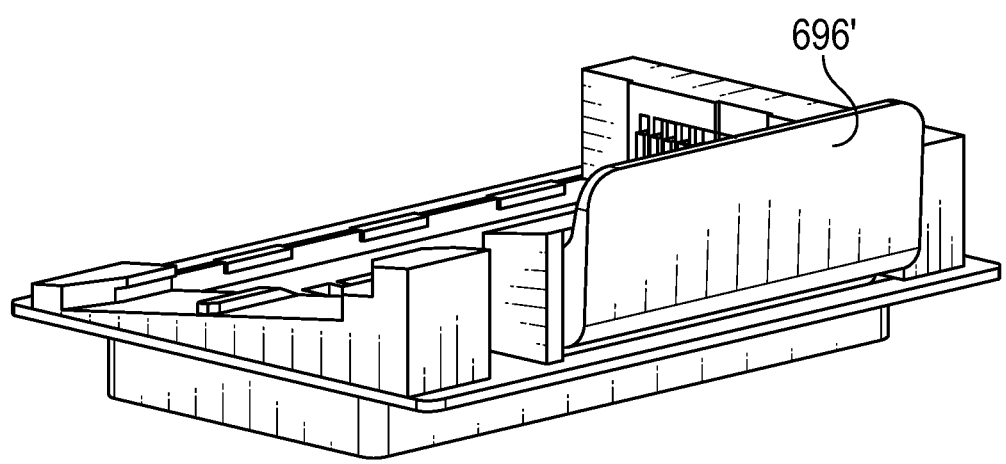

With reference to FIG. 4I, an adapter 680' is illustrated. The adapter 680' can be similar to the adapter 680 (and vice versa). The adapter 680' can include a plurality of rail sections 695' (for example, two as shown), which can operate similarly to the rail 695. In some cases, more than two rail sections 695' can be included. The rail sections 695' can be separated by one or more gaps. Lever 696' can operate similarly to the rail 696. Rail 696' can be shorter than the lever 696. The lever 696' can be integrated into a side of the housing of the adapter 680'.

Figure 4J:
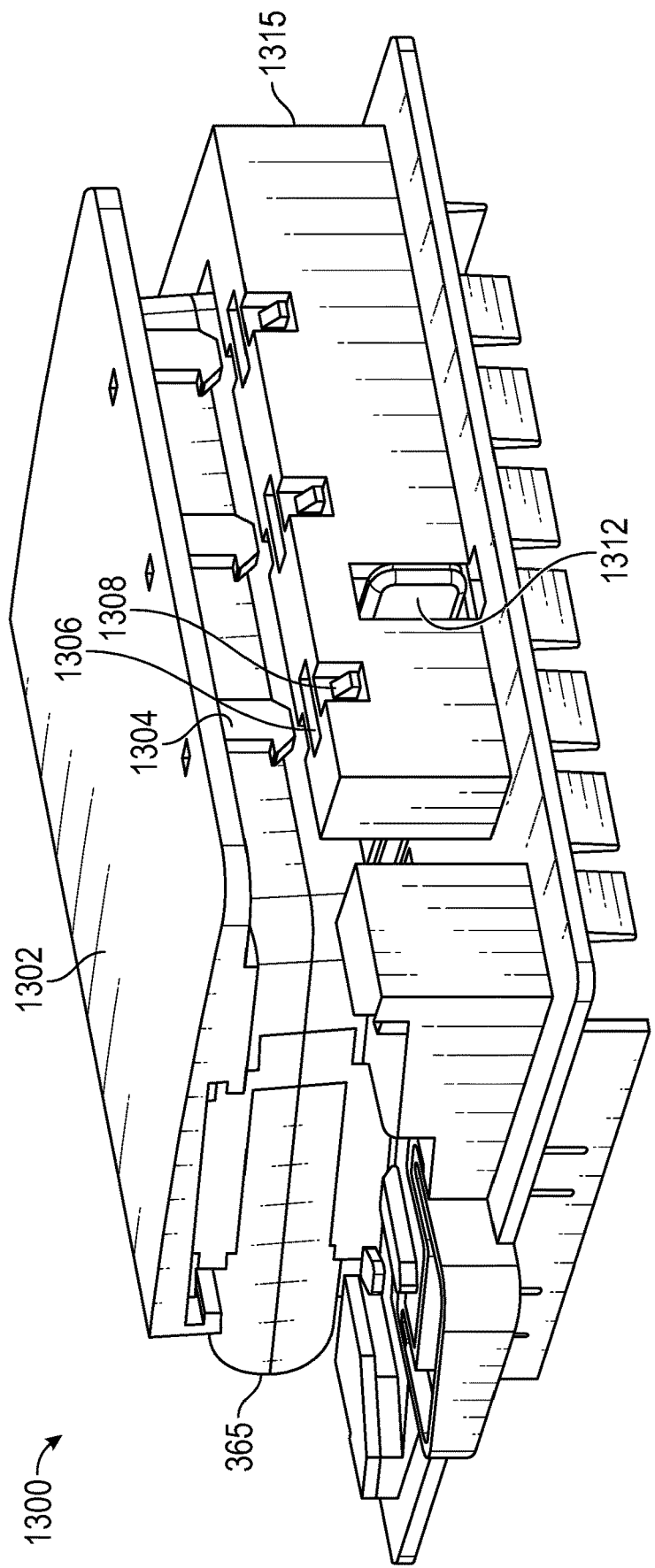

With reference to FIG. 4J, a combination 1300 of an adapter 1315 with the surgical instrument housing 365 is illustrated. The adapter 1315 can be similar to the adapter 680 (and vice versa). A cover 1302 can be positioned on the surgical instrument housing 365. The cover 1302 can be connected to the surgical instrument housing 365 (for example, removably connected). The cover 1302 can include one or more protrusions 1304 (sometime referred to as teeth). Housing of the adapter 1315 can include one or more openings 1306 configured to receive the protrusions 1304 of the cover 1302. When the surgical instrument housing 365 is rotated, the protrusions 1304 can engage with the openings 1306. This can maintain the surgical instrument housing 365 in the rotated position. The surgical instrument housing 365 can be rotated manually by the user (for example, moved downward or upward).

A release mechanism 1312 can positioned on or in the housing of the adapter 1315. The release mechanism 1312 can be a latch, such as a latch with an elastic material (for example, a spring). The release mechanism 1312 can be operated by the user (for example, moved to the right or left) to release the engagement of the protrusions 1304 with the openings 1306. This can cause the surgical instrument housing 365 to be released. The release mechanism 1312 can control one or more releases 1308 positioned in the housing of the adapter 1315. Each of the releases 1308 can release engagement of a corresponding pair of protrusion 1304 and openings 1306. For example, the releases 1308 can be moved upward to push the protrusions 1304 upward and disengage the protrusions 1306 from the openings 1306.

Figure 4K:
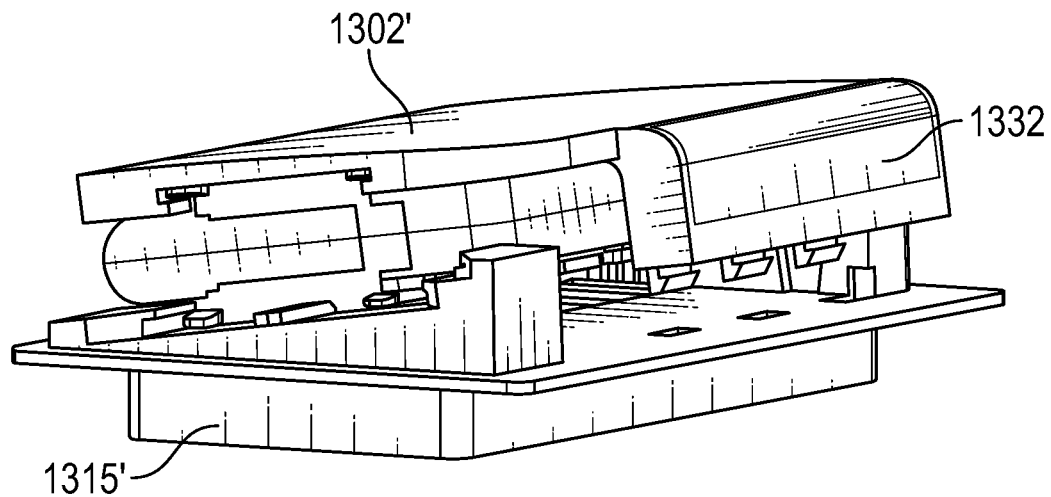
Figure 4L:
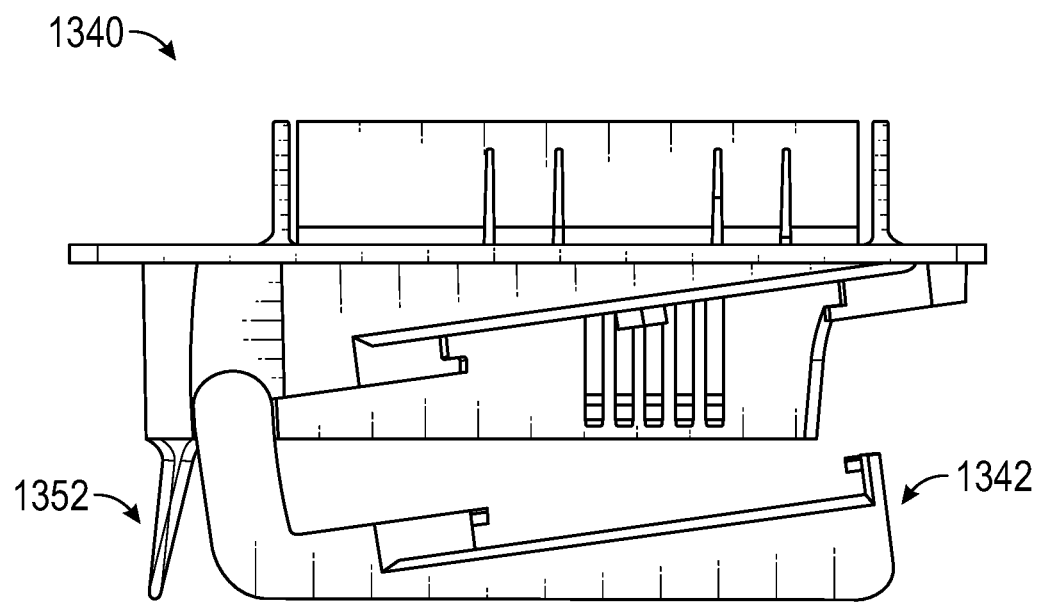
Figure 4M:
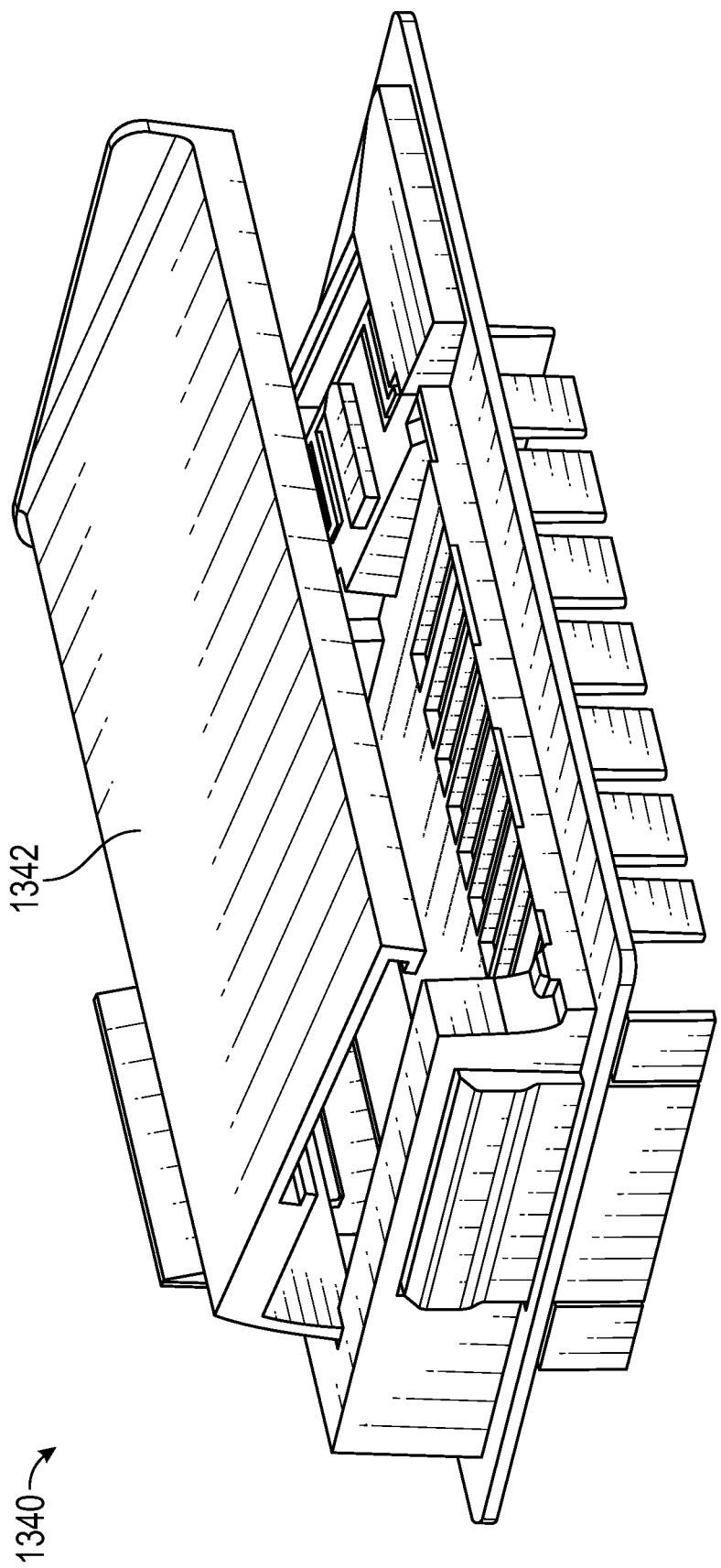
Figure 4N:
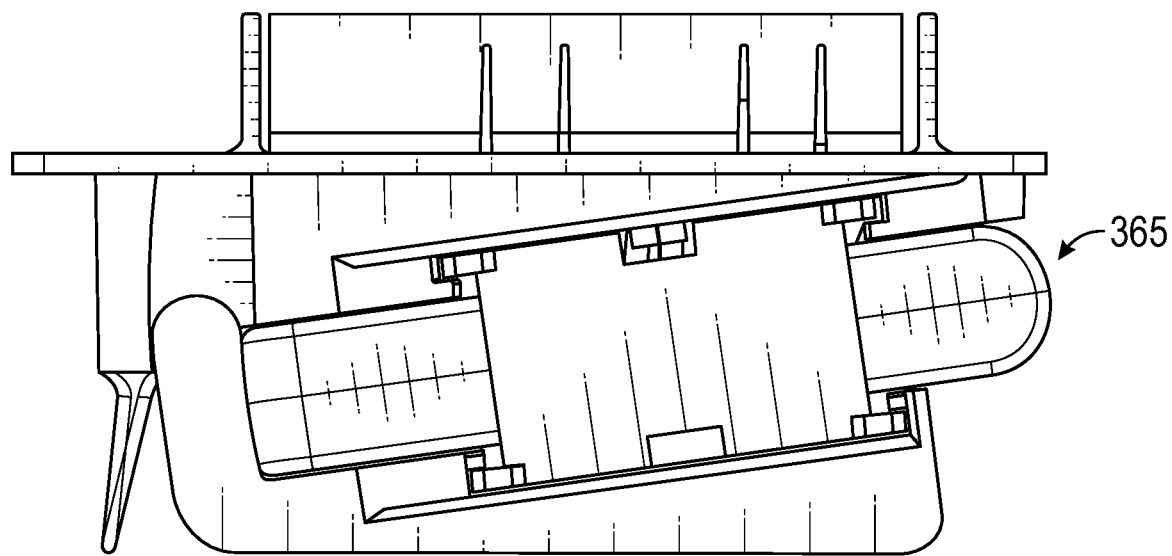
Figure 4O:
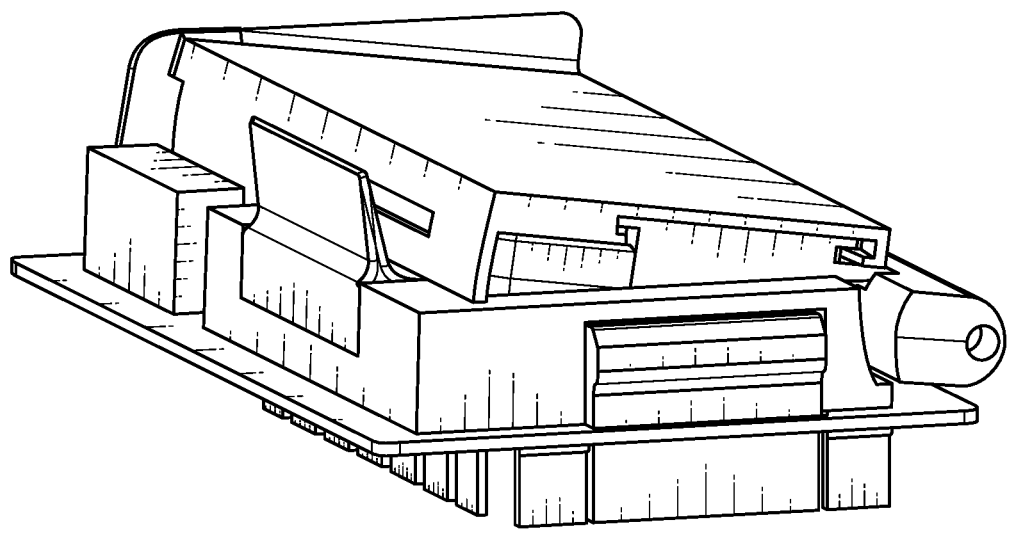

With reference to FIG. 4K, a cover 1302' can include a release mechanism 1332. The cover 1302' can be similar to the cover 1302 (and vice versa). The release mechanism 1332 can be a latch, such as a latch with an elastic material (for example, a spring). The release mechanism 1332 can operate similarly to the release mechanism 1312. The adapter 1315' can be similar to the adapter 1315 (and vice versa). The adapter 1315' may not include one or more of the release mechanisms 1312 and/or the releases 1308.

With reference to FIGS. 4L-4O, an adapter 1340 can include a support or holder 1342 configured to support the surgical instrument housing 365. The holder 1342 can support a bottom of the surgical instrument 364. The holder 1342 can be similar to any of the covers 1302 or 1302', but can be integrated with the adapter 1340. The holder 1342 can be rotated to cause the surgical instrument 364 to rotate. For example, the holder 1342 can be rotated counterclockwise. The holder 1342 can operate as a lever or a lever arm. A release mechanism 1352 can be operated by the user (for example, moved to the right or left) to cause the holder 1342 to rotate (for example, in the opposite direction, such as clockwise) and the surgical instrument housing 365 to be released. The release mechanism 1352 can be a latch, such as a latch with an elastic material (for example, a spring). The holder 1342 can be rotated manually by the user or by operating the release mechanism 1352 as described herein.

In some cases, a shaft of the surgical instrument, such as the shaft 368, can be flexible or substantially flexible. The surgical instrument housing can be rotated by flexing the shaft of the instrument. For example, with reference to FIG. 4E, the shaft 368 can be loaded into the instrument channel through the opening 340. The surgical instrument housing 365 can be rotated by flexing the shaft 368 to facilitate engagement of surgical instrument actuators 322 with the actuators 422 (covered by the actuator covers 622).

In some cases, any of the instrument channels can be wider at the end closer to the central unit 400, such as the end proximal to the opening 340. This can allow the shaft 368 to be moved within the instrument channel. The surgical instrument can be loaded at an angle and rotated to facilitate engagement of surgical instrument actuators 322 with the actuators 422 (covered by the actuator covers 622). The shaft can be moved through the wider part of the instrument channel to facilitate the rotation.

In some cases, in addition to or instead of rotation, any of the adapters described herein can be configured to facilitate any movement or transition of a surgical instrument from a first position or orientation in which the surgical instrument actuators 322 are disengaged from the actuators 422 (covered by the actuator covers 622) to a second position or orientation in which the instrument actuators 322 are engaged with the actuators 422. The surgical instrument can be loaded and unloaded by being moved forward and backward in or within the adapter, moved side to side in or within the adapter, or more generally moved from one position to another position in or within the adapter.

In some cases, some or all of the adapters described herein may not be used. One or more instrument interfaces 420 can be sterilized before loading of the one or more instruments. One or more instrument interface 420 can be configured to allow the one or more instruments to rotate (or transition) using any of the approaches described herein.

Sterile Barrier for Arm

Figure 5:
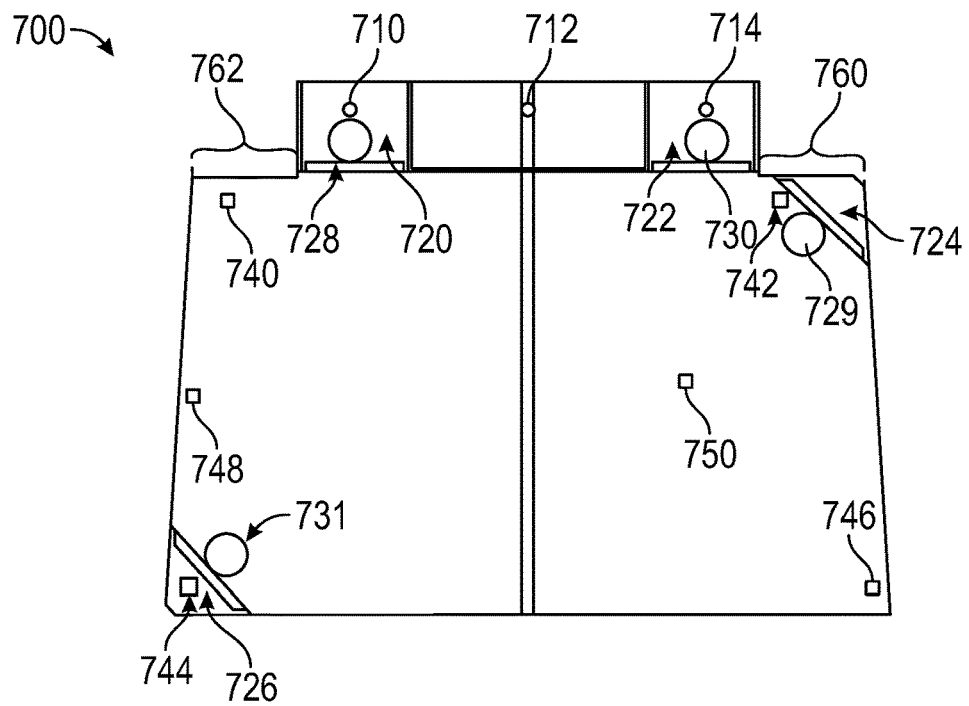
FIG. 5 illustrates a sterile barrier for an elevating linkage assembly of the robotic surgery system.

FIG. 5 illustrates the drape 700 for the arm 300 in an unfolded configuration. The drape 700 can be positioned (such as, removably attached) on the arm 300. The drape 700 can enclose at least a portion of the arm 300 (see, for example, FIGS. 8O-8U). The drape 700 can be flexible or substantially flexible similarly to the drape 600.

As described herein in connection with the drape 600, drape 700 can include one or more pockets 720 and 722. These pockets can be similar to any of the pockets described herein, such as any of the pockets 672, 674, 676, and 678 of the drape 600. The pockets 720 and 722 can be positioned on an outer facing surface of the drape 700, which as described herein may provide the sterile barrier. The pockets 720 and 722 can be labeled, for example, with labels 728 and 730, respectively. Labels 728 and 730 can be similar to any of the labels described herein, such as any of the labels 666, 667, 668, and 669 of the drape 600. As described herein, labels 728 and 730 can include indications guiding the user to insert a particular hand (or portion of the hand) into the pocket. Label 728 can guide the user to insert the left hand (or portion of the left hand) into the pocket 720. Label 730 can guide the user to insert the right hand (or portion of the right hand) into the pocket 722. As described herein with respect to the drape 600, the pockets 720 and 722 can be paired. The labels can provide indication of the pairing, such as, include the number "1," as described herein (for instance, to signify an earlier or first step in the process for covering the arm 300 with the drape 700).

The drape 700 can include one or more attachments or fasteners 710, 712, and 714, which can be similar to any of the fasteners 652 and 662 of the drape 600. Fastener 710 can be positioned in a region of the drape covered by (or overlapping with) the pocket 720. Fastener 714 can be positioned in a region of the drape 700 covered by the pocket 722. Fastener 712 can be positioned in a region (such as, in the middle) of the drape 700 not overlapped by a pocket. As described herein, for example in connection with the fasteners 652 and 662, one or more of the fasteners 710, 712, and 714 can include ferromagnetic material, such as a metal washer, configured to be attached to an attachment or fastener of the arm 300. As described herein, any of the fasteners 710, 712, and 714 can be positioned on or adjacent to an inner facing surface of the drape 700, which can be configured to come into contact with the arm 300.

Figure 8A:
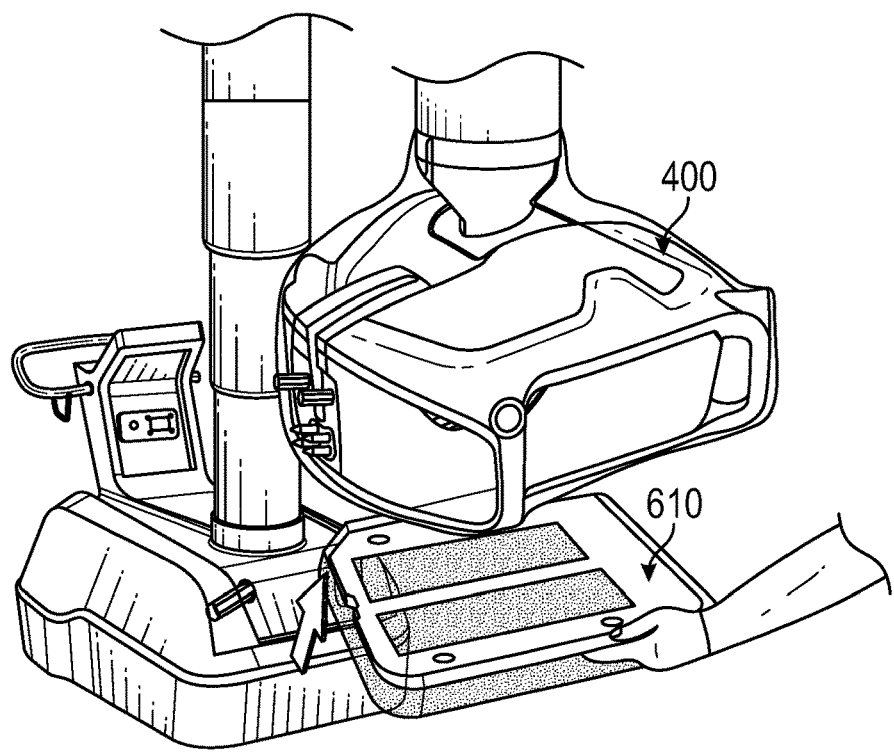
FIGS. 8A-8W illustrate covering components of the robotic surgery system with one or more sterile barriers.
Figure 8B:
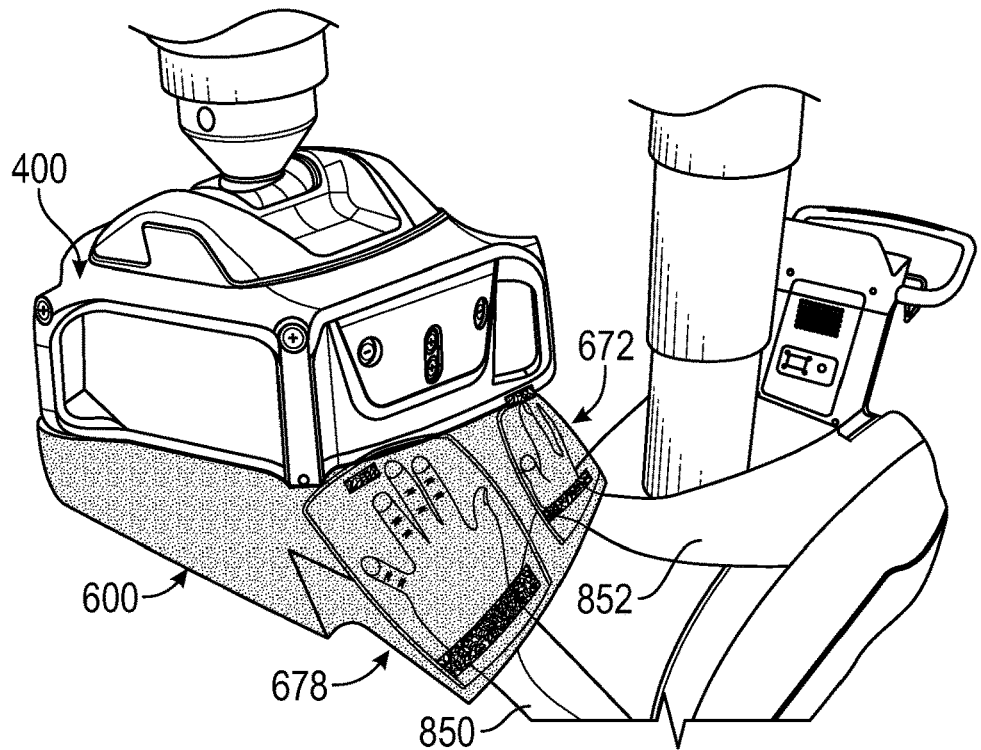
Figure 8C:
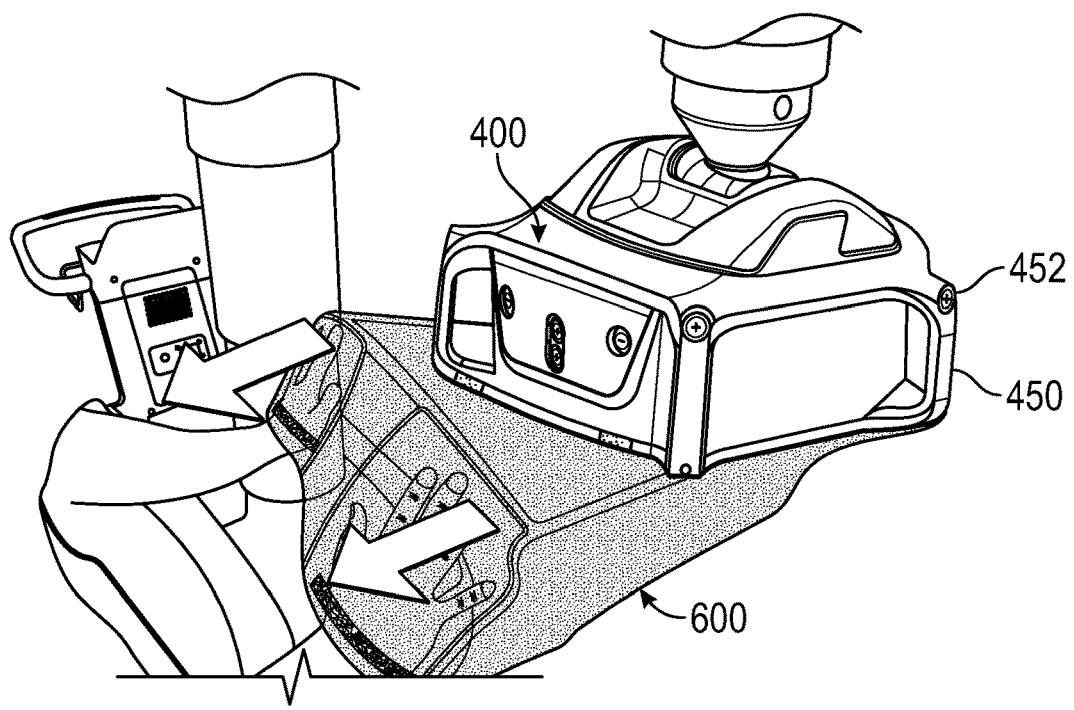
Figure 8D:
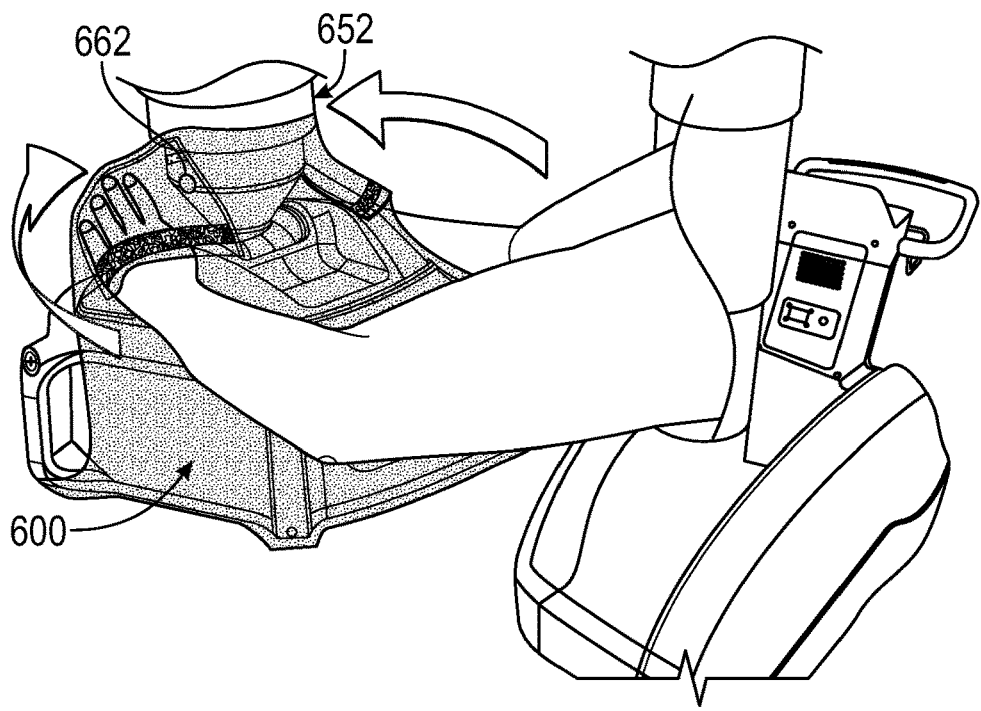
Figure 8E:
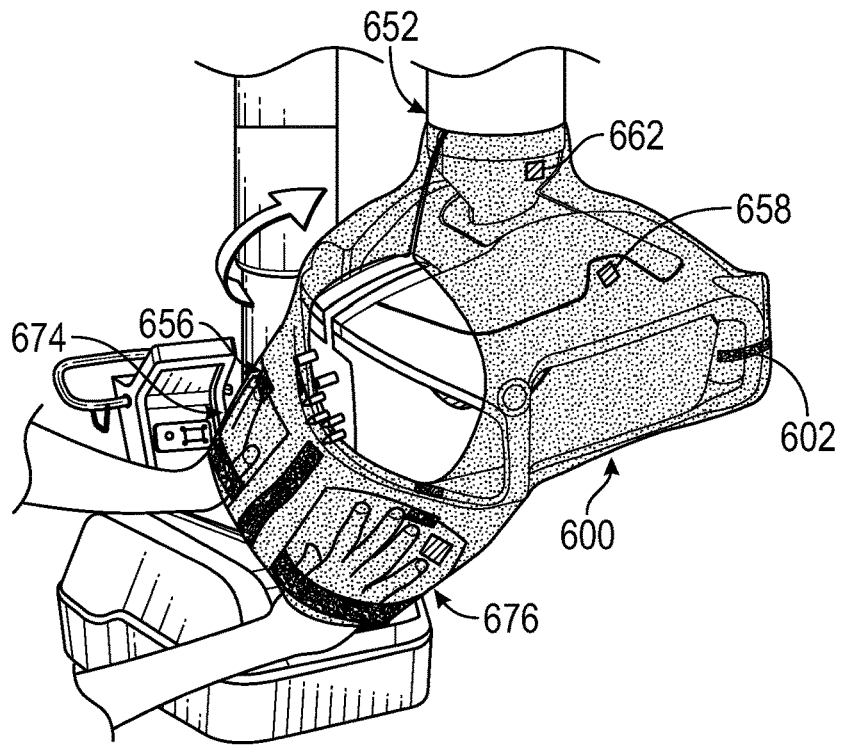
Figure 8F:
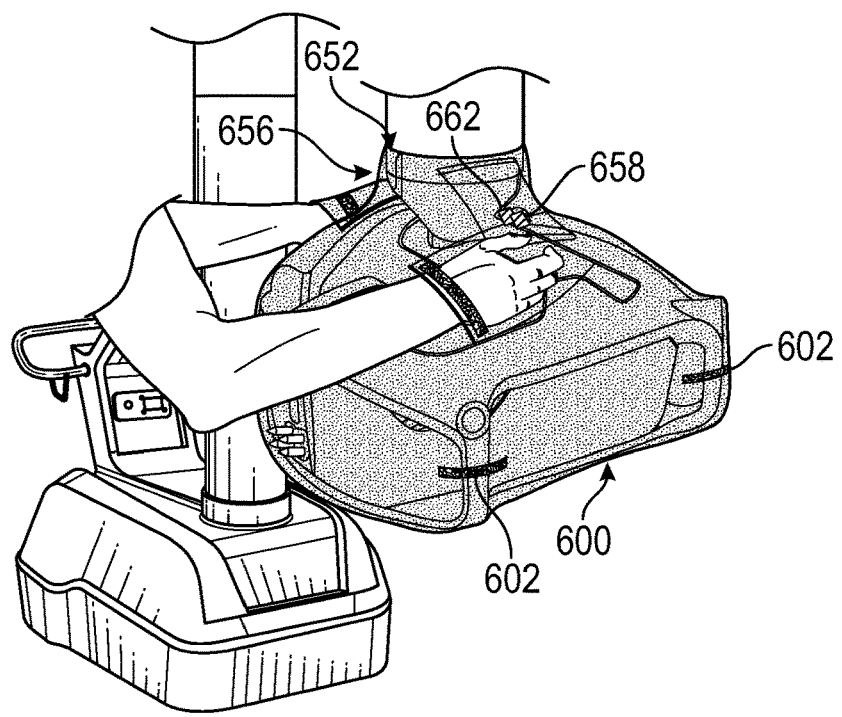
Figure 8G:
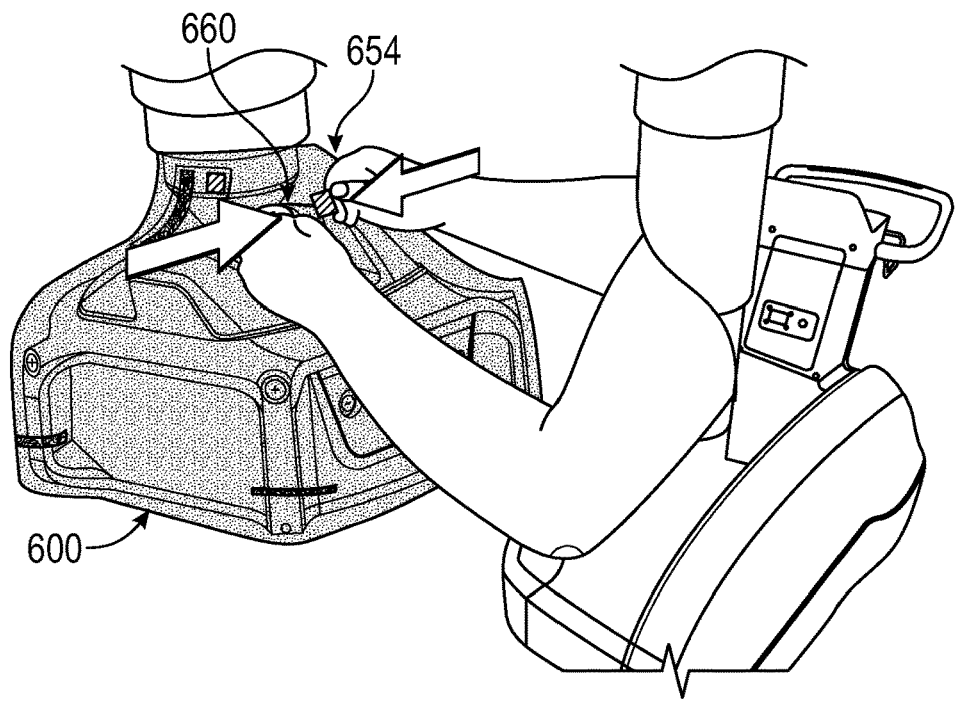
Figure 8H:
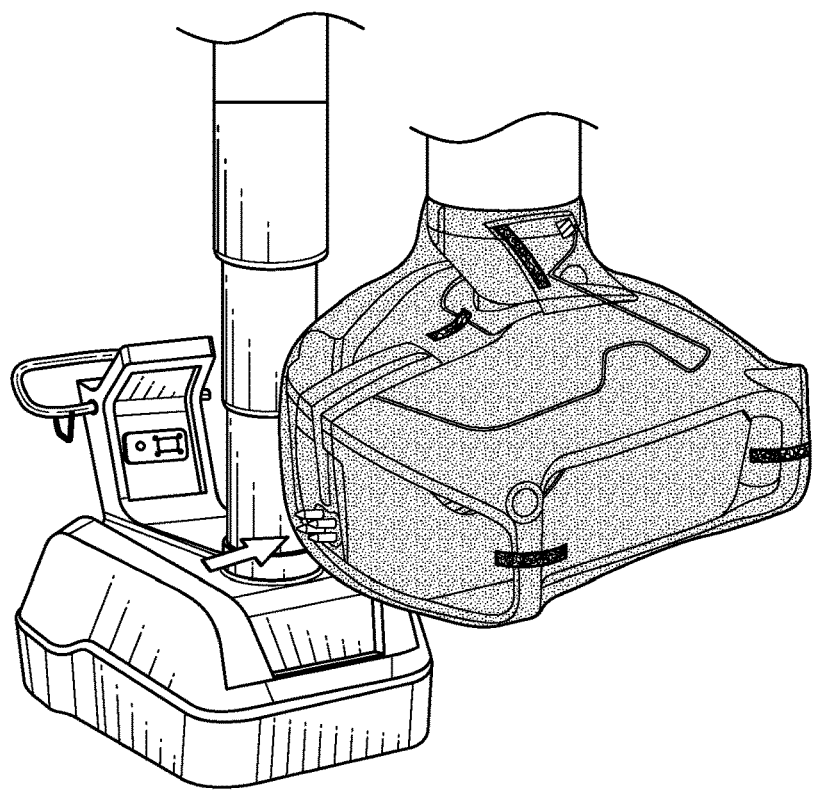
Figure 8I:
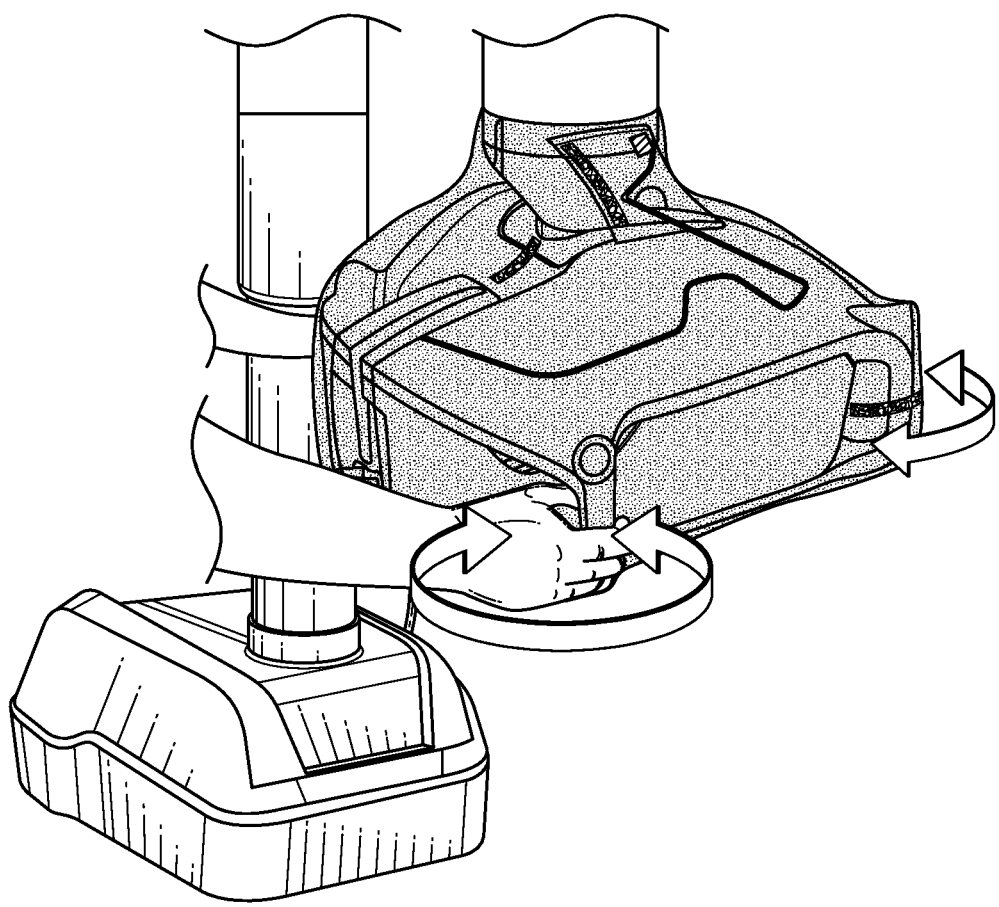
Figure 8J:
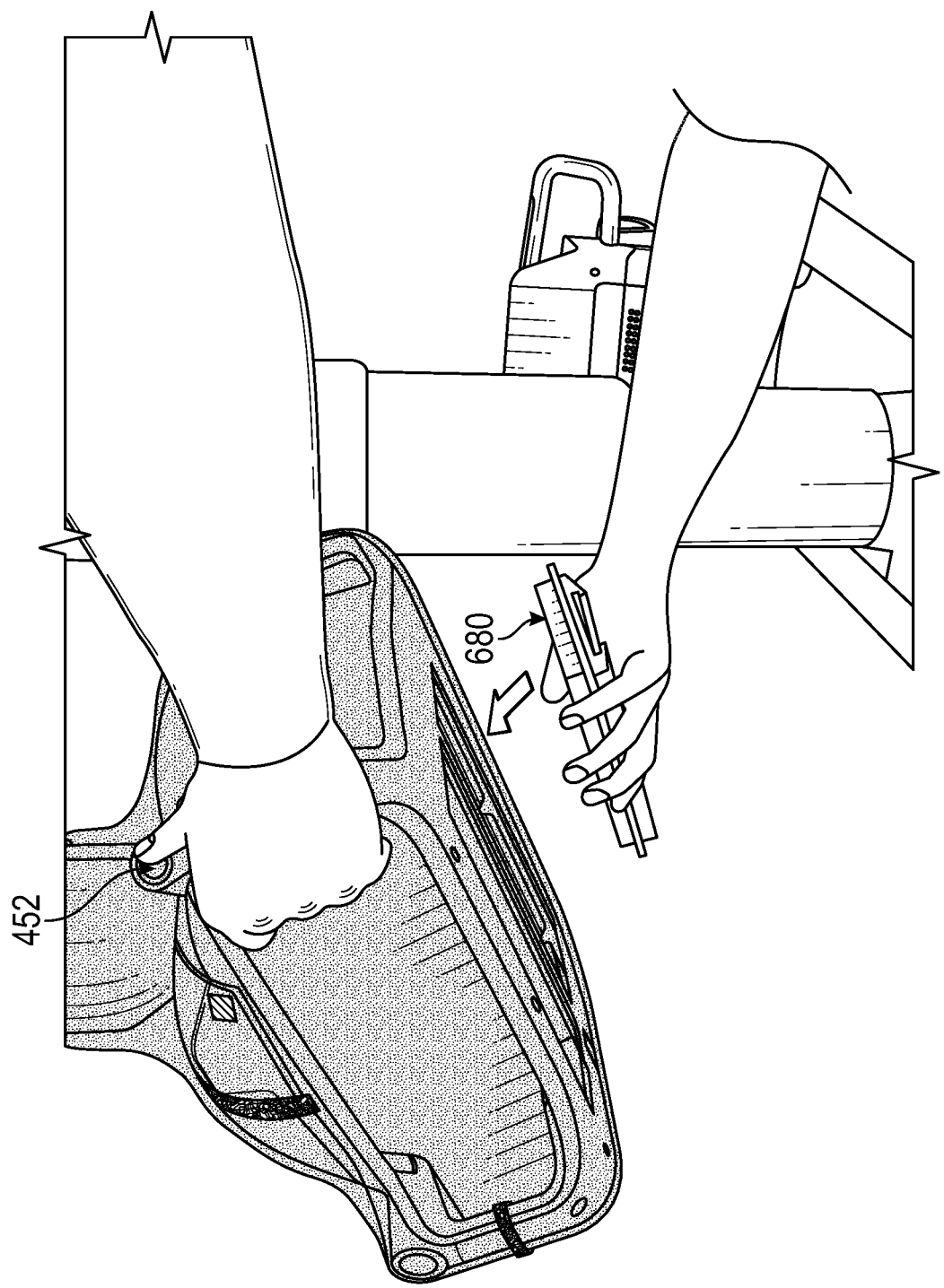
Figure 8K:
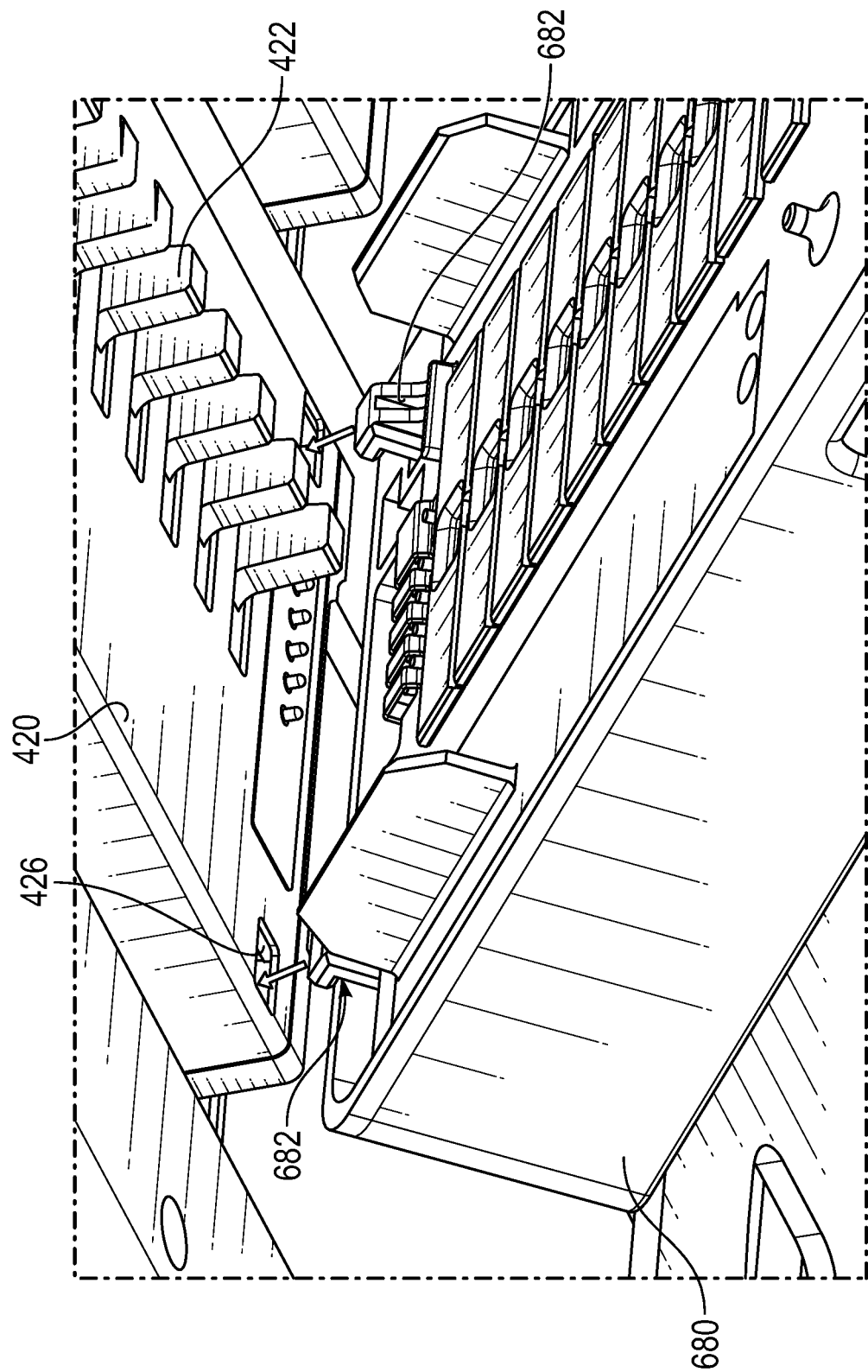
Figure 8M:
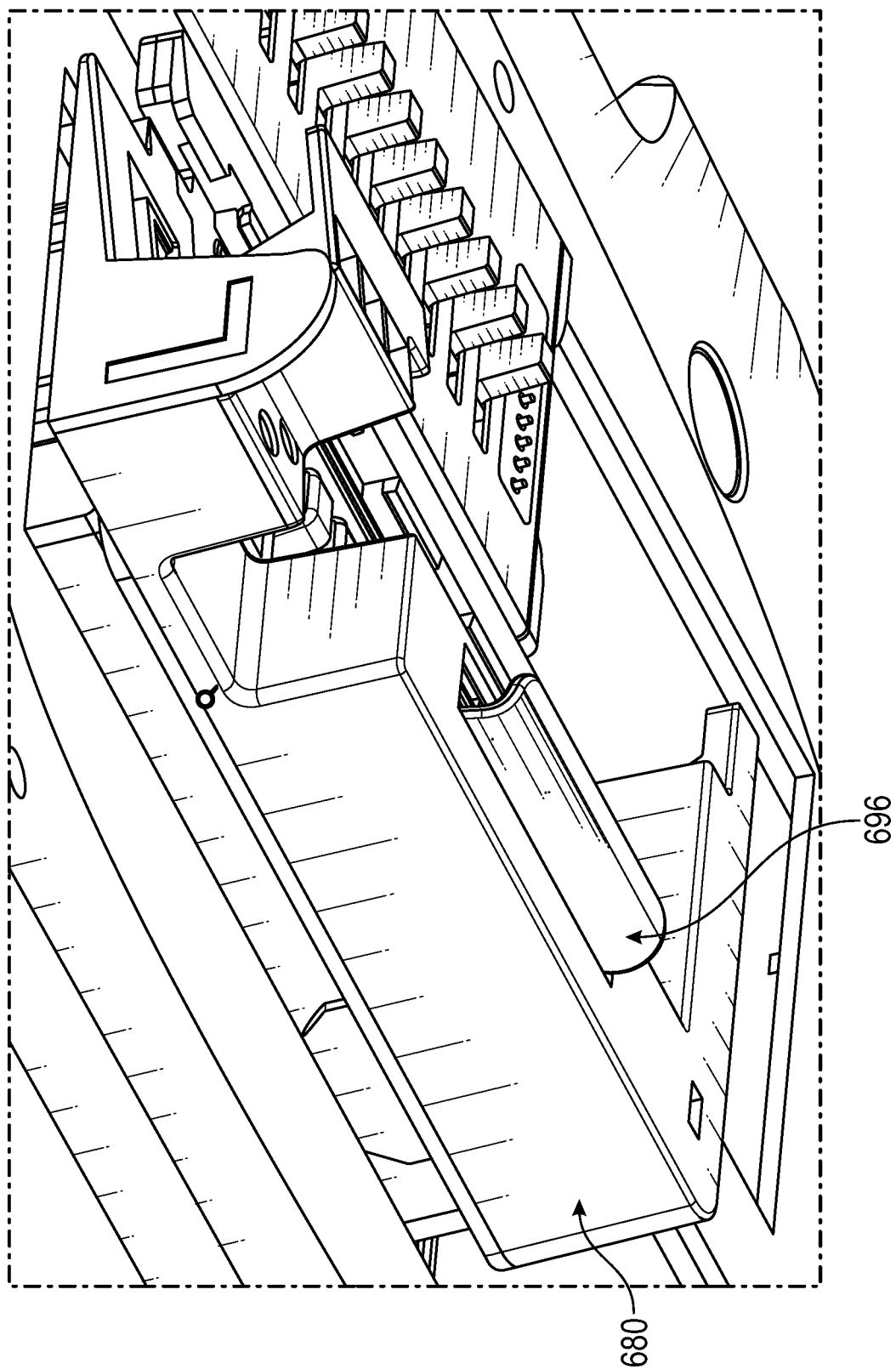
Figure 8N:
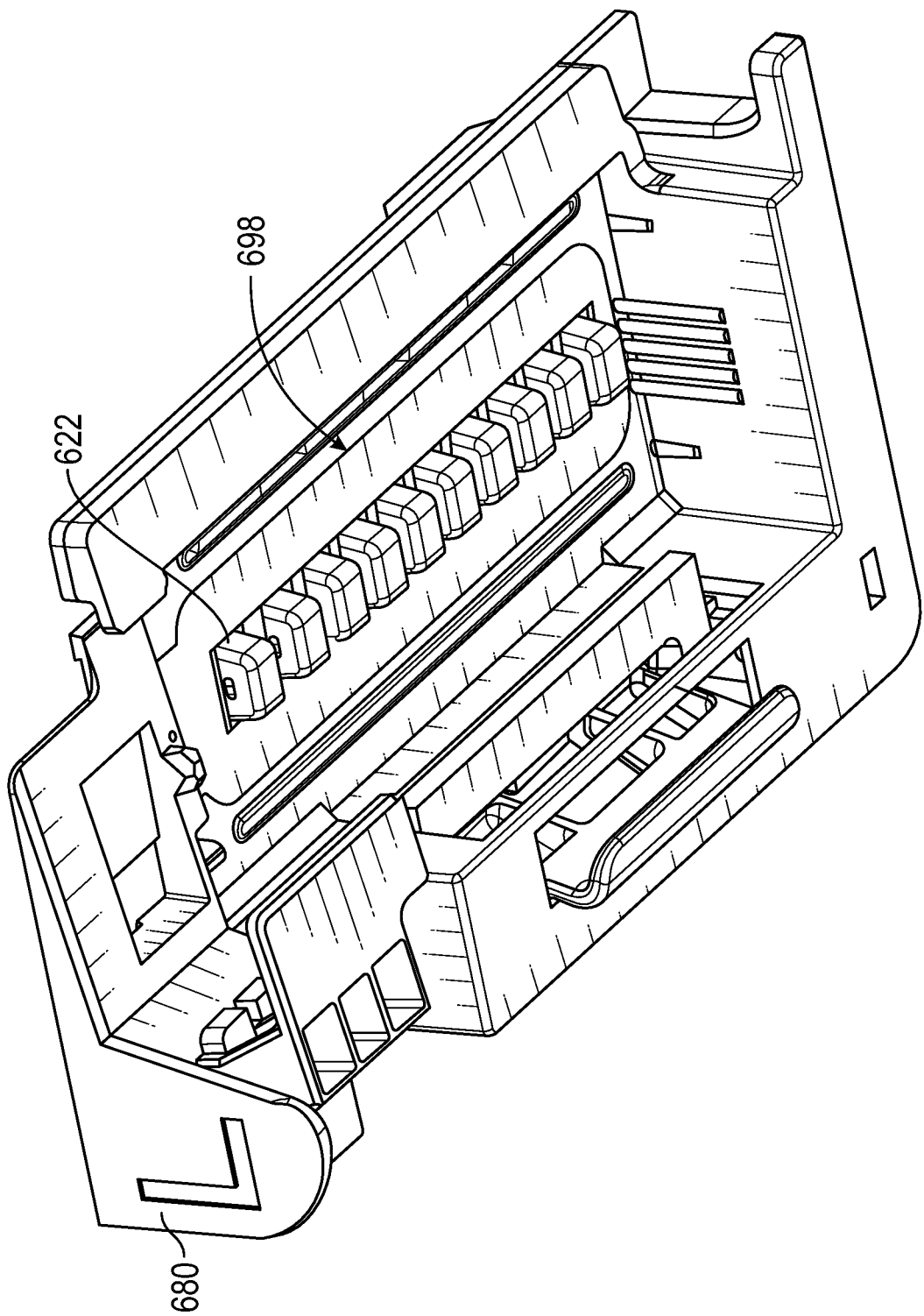
Figure 8O:
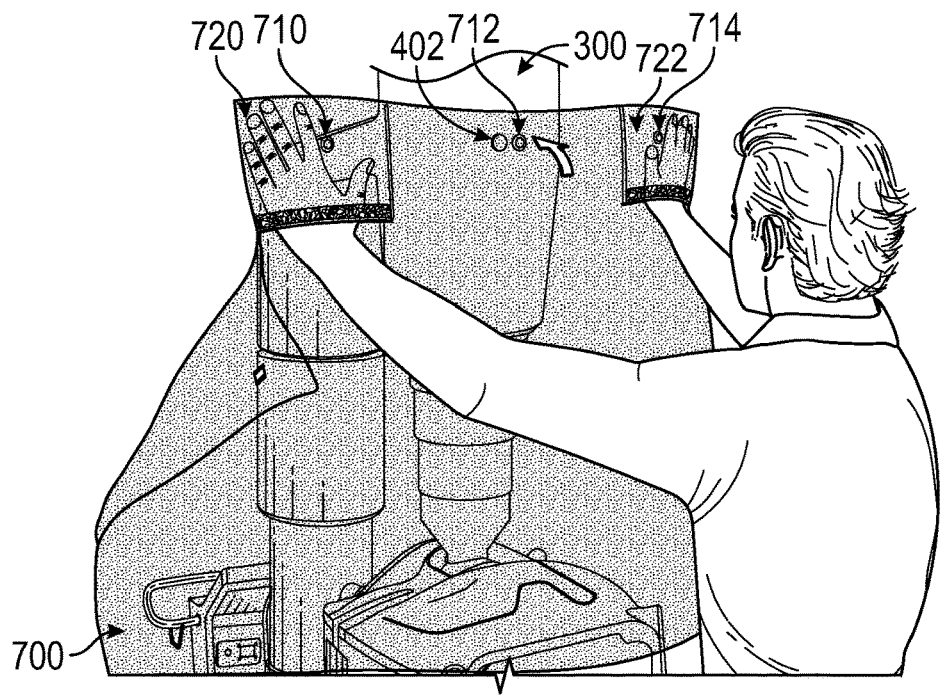
Figure 8P:
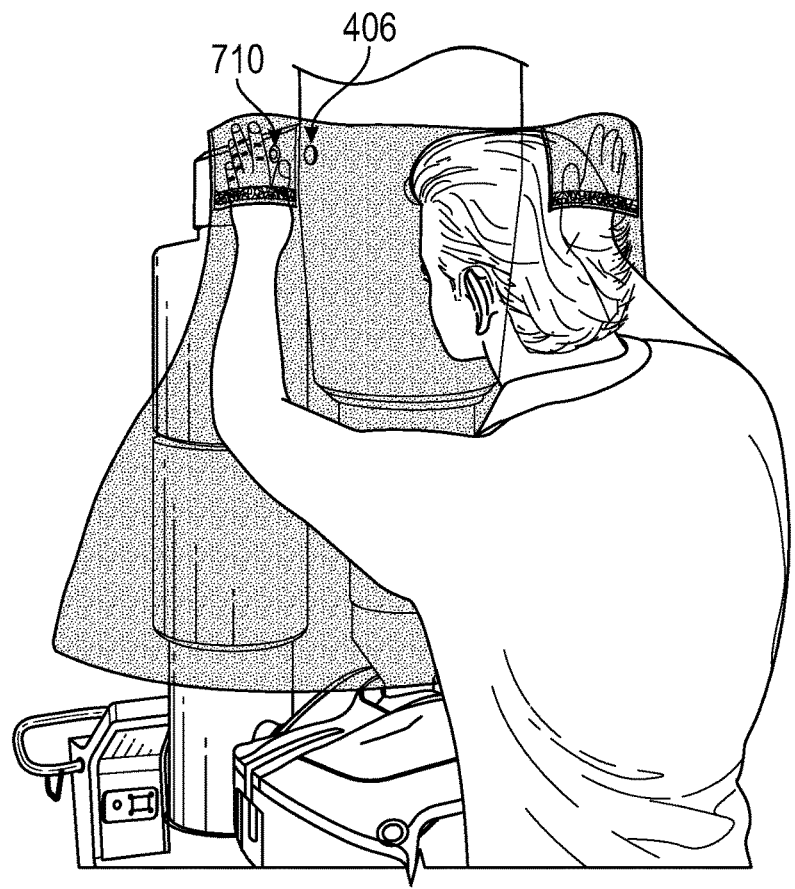

As described herein in connection with the pockets of the drape 600, the pockets 720 and 722 can facilitate maintaining sterility of the outer surface of the drape when the user is attaching one or more fasteners 710, 712, and 714 to the fasteners of the arm 300 (as shown, for example, in FIGS. 8O-8P). As illustrated in FIGS. 5 and 8O-8P, a pocket may not be needed to facilitate attachment of the fastener 712 as use of the pockets 720 and 722 can be sufficient for attachment of the fastener 712. For example, because the fastener 712 can be positioned in the middle portion of the drape 700, it would be brought into contact or into proximity of the fastener 402 positioned in the middle of the arm 300. In some cases, a pocket overlapping the fastener 712 can be provided. In some cases, when such pocket is provided, any one or more of the pockets 720 or 722 can be omitted.

The drape 700 can include a pocket 724, which can be positioned on a flap 760 on the right side of the drape. The pocket 724 can be similar to any of the pockets described herein. The pocket 724 can be positioned on the outer facing surface of the drape 700. The pocket 724 can be configured to enclose a portion of the user's hand, such as the left hand, to facilitate enclosing a portion of the arm 300 with the drape (such as, wrapping the drape 700 around the arm; see, for example, FIGS. 8Q-8U). In some cases, the pocket 724 can be smaller than any of the pockets 720 or 722. For example, the pocket 724 can be configured (for example, sized and shaped) to enclose a portion of the user's hand, such as fully or partially enclose four fingers excluding the thumb (see, for example, FIG. 8R). In some cases, the pocket 724 can be configured to enclose less than four fingers. The drape 700 can include a label 729, which can be similar to any of the labels described herein. The label 729 can guide the user to insert a portion of the left hand into the pocket 724. The label 729 can include an indication of a step in the process for covering the arm 300. Such step can be subsequent to the step of attaching the fasteners 710, 712, and 714 to the arm 300 (and affixing the top portion of the drape to the arm). For example, the label 729 can include the number "2," as described herein. The pocket 724 can facilitate one or more of maintaining sterility of the outer facing surface of the drape when the drape is positioned (such as, wrapped around) the arm 300, facilitating wrapping the drape 700 around the arm 300 (for example, by providing an anchor or level to the user), or the like. The pocket 724 may not be paired with another pocket.

Figure 8Q:
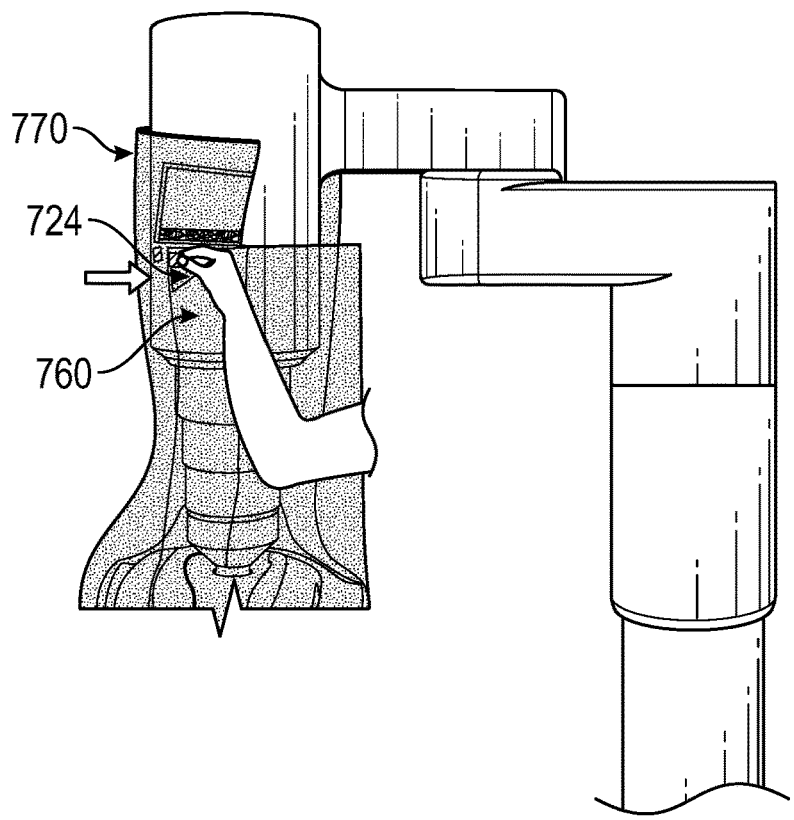
Figure 8R:
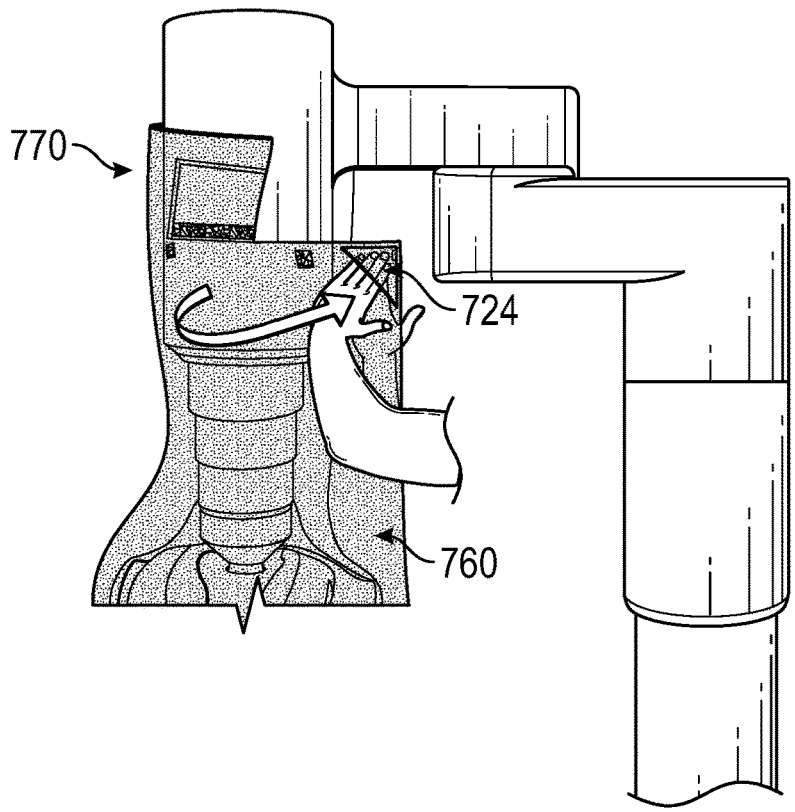

Pocket 724 can be used to facilitate wrapping the drape 700 around the arm 300. With reference to FIG. 8Q, the user can detach the flap 760 from the drape (such as, from the middle portion of the drape adjacent to the flap 760). For example, the user could remove or break a tearable tab or another removable or detachable closure or attachment. With reference to FIG. 8R, the user can wrap the flap 760 (and in some cases other portions of the drape) around the arm 300. For example, the user can wrap the flap around one or more of the sides or back of the arm 300 to cover those portions of the arm. Illustrated arrow can indicate direction for wrapping the drape 700 around the arm 300 (such as, counterclockwise). The user can wrap the drape by using the hand positioned in the pocket 724 (such as, the left hand).

With reference to FIG. 5, the drape can include one or more fasteners 740, 742, 744, 746, 748, and 750, which can be similar to any of the fasteners described herein (such as, the fasteners 654, 656, 658, and 660 of the drape 600). For example, the fasteners 740, 742, 744, 746, 748, and 750 can be VELCRO fasteners. As described herein, the fasteners can be paired. For example, the pairing can be: 740 with 742, 748 with 750, and 744 with 746. Paired fasteners can be attached to one another to facilitate covering the arm 300 with the drape 700 (such as, wrapping the drape around the arm). Fasteners 740, 744, and 748 can be positioned on a flap 762 (on the left side of the drape), such as, on the inner facing surface of the flap (or on the outer facing surface). Fasteners 742, 746, and 750 can be positioned on the flap 760 (on the right side of the drape), such as, on the opposite surface than the paired fasteners 740, 748, and 744 (for example, on the outer facing surface). In some cases, fasteners 742, 746, and 750 can be positioned on the same surface as the parried fasteners 740, 744, and 748.

Figure 8S:
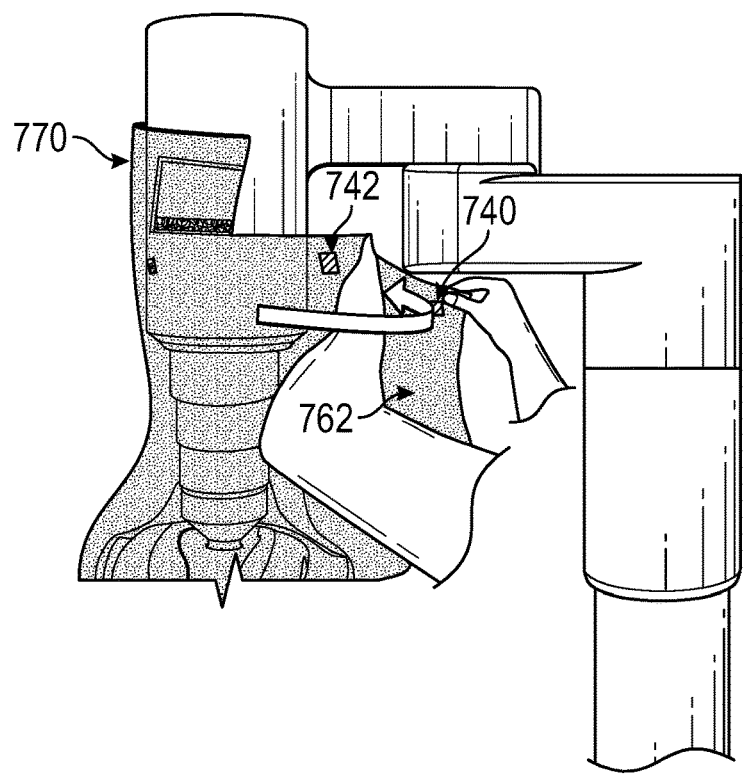
Figure 8T:
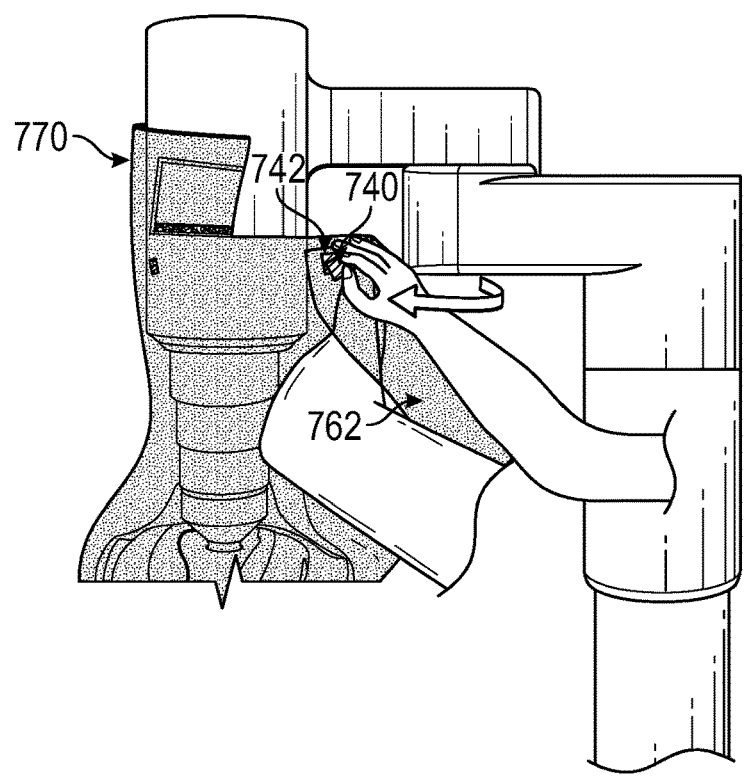

With reference to FIG. 8S, the drape 700 is illustrated being wrapped around the arm 300 (such as, after the flap 760 being wrapped around the arm). The user's hand (such as, left hand) can remain in the pocket 724. With the other hand (such as, right hand), the user can wrap the flap 762 (and in some cases other portions of the drape) around the portion of the drape wrapped around the arm (such as, the flap 760). The user can also attach the paired fasteners 740 and 742 to each other, as illustrated in FIG. 8T.

The user may touch or grab the flap 762 as illustrated without the risk (or with low risk) of touching a surface that has come into contact with any non-sterile surfaces of the arm 300. Such risk may not be present (or may be low) because the flap 762 may be attached to the drape (such as, to the middle portion of the drape adjacent to the flap 762) as described in connection with the flap 760. The user can detach the flap 762, for example, by removing or breaking a tearable tab or another removable or detachable closure or attachment. The user can wrap the flap 762 around the flap 760 as illustrated by the arrow in FIG. 8T. Attachment of the fasteners 740 and 742 can secure the top portion of the drape 700 around the arm 300. Attachment of paired fasteners 748 and 750 can similarly facilitate securing the middle portion of the drape around the arm 300.

As illustrated in FIG. 5, the pocket 724 can be positioned adjacent to (or overlapping) the fastener 742. This can facilitate attaching the fastener 742 to the fastener 740. In some cases, one or more pockets, which can be similar to the pocket 724, can be positioned on the flap 762. For example, a pocket similar to the pocket 724 can be positioned adjacent (or overlapping) the fastener 740. One or more pockets can be positioned adjacent to (or overlapping) one or more fasteners 746, 748, and 750.

Drape 700 can include a pocket 726, which can be similar to the pocket 724. Pocket 726 can be positioned in the bottom portion of the drape, such as in the bottom portion of the flap 762. A label 731, which can be similar to any of the labels described herein, can guide the user to insert a hand (or portion of the hand), such as the right hand, into the pocket 726. The label 731 can include an indication of a step in the process of covering the arm subsequent to attaching the fasteners 740 and 742. For example, the label 729 can include the number "3," as described herein. The pocket 726 may not be paired with another pocket.

Figure 8U:
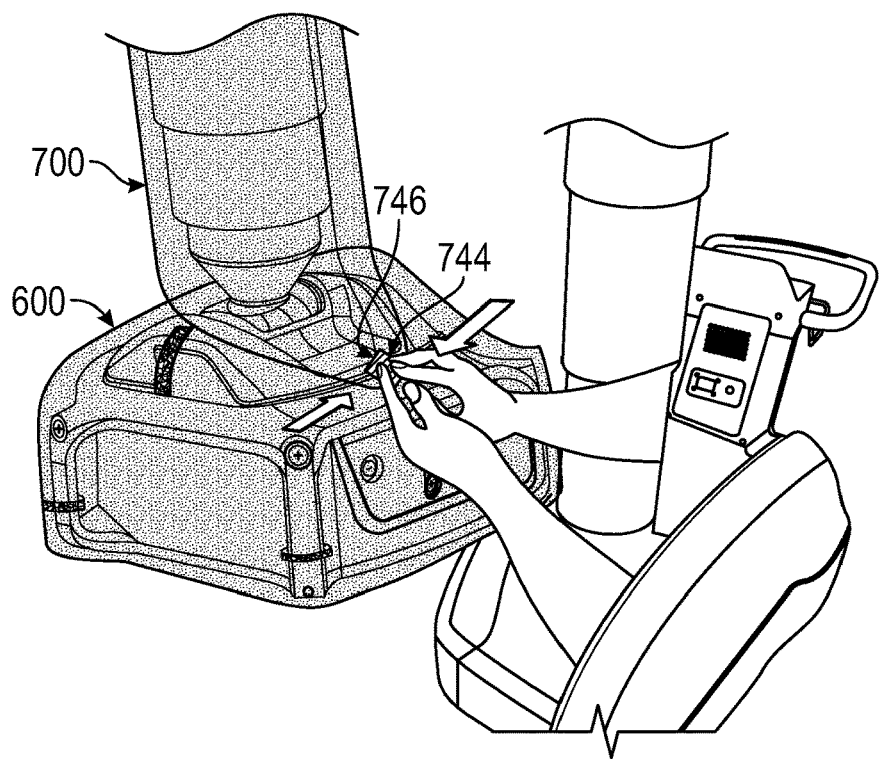

As illustrated in FIG. 8U, the pocket 726 can facilitate attaching the fasteners 744 and 746. For example, the fastener 744 can be positioned on the outer facing surface of the pocket 726. With reference to FIG. 5, the pocket 726 can overlap the fastener 744. This can provide an anchor or lever to the user for facilitating attachment of the fasteners 744 and 746.

Attachment of the fasteners 740 and 742 can secure (or tighten) the bottom portion of the drape 700 around the arm 300. As illustrated in FIG. 8U, the bottom portion of the drape 700 can partially overlap the top portion of the drape 600. The drapes 600 or 700 can move independently of the other, for example, due to the drapes being separate (or modular). Movement of one drape may not cause movement of the other drape. Such modularity and independence of the drapes provides advantages over existing monolithic drapes that are large, bulky, and require multiple users for installation. Some of the advantages include facilitating secure and tight fit of the drapes around different robotic surgery system components that have different shapes and sizes (such as, the central unit 400 and the arm 300), facilitating easier and more efficient management and installation of the drapes (for example, facilitating installation by a single user, such as sterile nurse), facilitating quicker installation, and promoting safety by lessening the risk of losing sterility during installation (for example, as a result of a sterile surface of the drape coming into contact with a non-sterile surface of a system component).

In some cases, the drapes 600 and 700 can be coupled. For example, the drapes 600 and 700 can be attached to each other using any of the one or more fasteners described herein.

In some cases, any of the pockets, fasteners, or labels illustrated in FIG. 5 can be positioned in a different location (including on a different surface) or removed. Additional pockets, fasteners, or labels fasteners can be added. In some cases, the drape 700 may include an additional drape region or portion (shown, for example, as 770 in FIGS. 8Q to 8T) positioned above one or more of the pockets 720 and 722. The additional drape portion may include a more rigid material (than that of the material of the drape 700) in order to cause the additional drape portion to remain upright during the medical procedure. In some cases, the additional drape portion can alternatively or additionally include supports (such as, supporting membranes) configured to hold the additional drape portion upright. The inclusion of the additional drape portion may be useful when a sterile barrier is needed above the point or region of fastening of the drape 700 to or on the robotic surgery system. The inclusion of the additional drape portion may additionally or alternatively be useful to facilitate fastening of the drape 700 to the arm 300 by the user (such as, the sterile nurse) of an average height without needing to otherwise be supported (for example, by the use of a ladder) in order to reach the fasteners on the arm 300, while providing sufficient sterile barrier coverage of the arm above the fasteners.

Sterile Barrier for Column

Figure 6A:
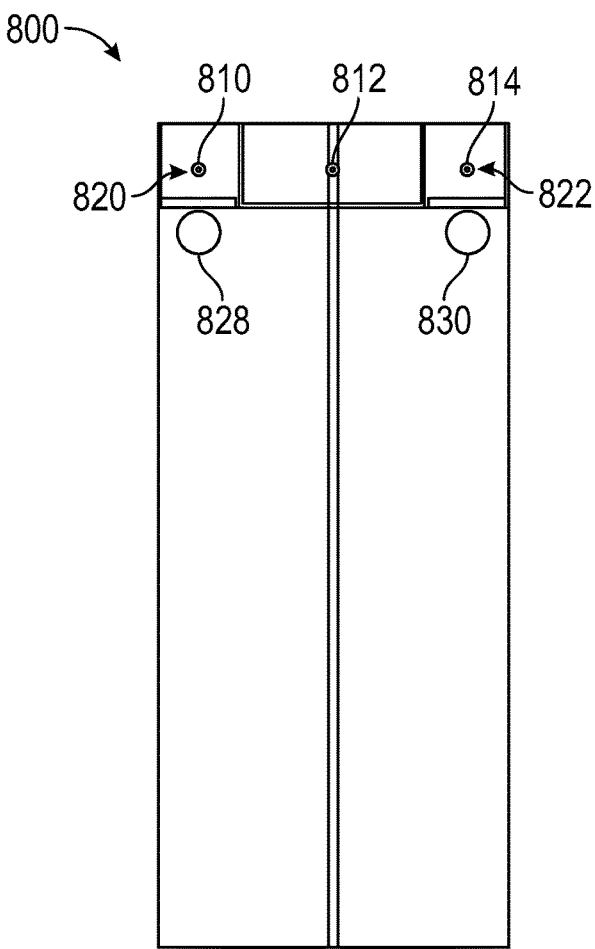
FIG. 6A illustrates a sterile barrier for a boom arm assembly of the robotic surgery system.

FIG. 6A illustrates the drape 800 in an unfolded configuration. The drape 800 can be positioned on the column 200

(such as, removably attached). The drape 800 can cover at least a portion of the column 200 (see, for example, FIGS. 8V-8W). The drape 800 can be flexible or substantially flexible similarly to any of the drapes 600 or 700.

As described herein in connection with any of the drapes 600 or 700, the drape 800 can include one or more pockets 820 and 822. These pockets can be similar to any of the pockets described herein, such as any of the pockets 672, 674, 676, and 678 of the drape 600 or any of the pockets 720 and 722 of the drape 700. The pockets 820 and 822 can be positioned on an outer facing surface of the drape 800, which as described herein may provide the sterile barrier. The pockets 820 and 822 can be labeled, for example, with labels 828 and 830, respectively. Labels 828 and 830 can be similar to any of the labels described herein, such as any of the labels 666, 667, 668, and 669 of the drape 600 or any of the labels 728 and 730 of the drape 700. As described herein, labels 828 and 830 can include indications guiding the user to insert a particular hand (or portion of the hand) into the pocket. Label 828 can guide the user to insert the left hand (or portion of the left hand) into the pocket 820. Label 830 can guide the user to insert the right hand (or portion of the right hand) into the pocket 822. As described herein with respect to the drape 600 or 700, the pockets 820 and 822 can be paired. The labels can provide indication of the pairing, such as, include the number "1," as described herein (for instance, to signify an earlier or first step in the process for covering the column 200 with the drape 800).

The drape 800 can include one or more attachments or fasteners 810, 812, and 814, which can be similar to any of the fasteners 652 and 662 of the drape 600 or fasteners 710, 712, and 714 of the drape 700. Fastener 810 can be positioned in a region of the drape covered by (or overlapping with) the pocket 820. Fastener 814 can be positioned in a region of the drape covered by the pocket 822. Fastener 812 can be positioned in the region of the drape (such as, in the middle) not overlapped by a pocket. As described herein, for example in connection with the fasteners 652 and 662 of the drape 600 or fasteners 710, 712, and 714 of the drape 700, one or more of the fasteners 810, 812, and 814 can include ferromagnetic material, such as a metal washer, configured to be attached to an attachment or fastener of the column 200. As described herein, any of the fasteners 810, 812, and 814 can be positioned on or adjacent to an inner facing surface of the drape 800, which can be configured to come into contact with the column 200.

Figure 8V:
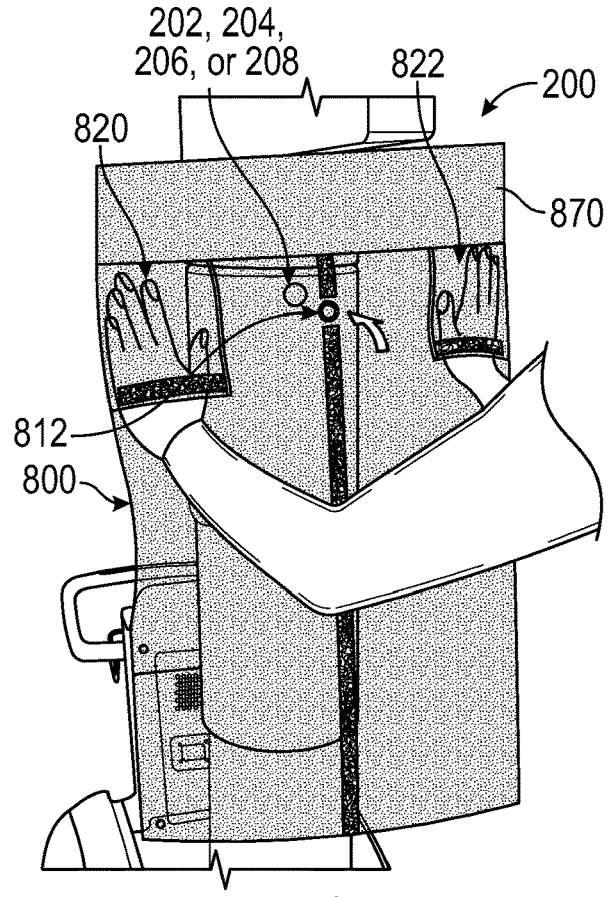
Figure 8W:
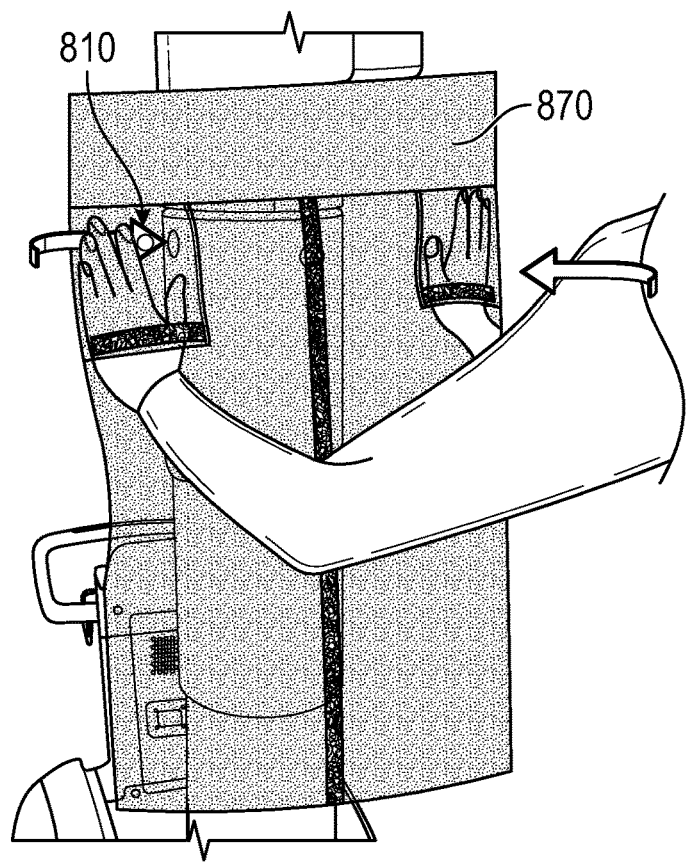

As described herein in connection with the pockets of the drape 600 or 700, the pockets 820 and 822 can facilitate maintaining sterility of the outer surface of the drape when the user is attaching one or more fasteners 810, 812, and 814 to the fasteners of the column 200 (as shown, for example, in FIGS. 8V-8W). As illustrated in FIGS. 6A and 8V-8W, a pocket may not be needed to facilitate attachment of the fastener 812 as use of the pockets 820 and 822 can be sufficient for attachment of the fastener 812 (similarly, to the drape 700). For example, because the fastener 812 can be positioned in the middle portion of the drape 800, it would be brought into contact or into proximity of one of the fasteners 202, 204, 206, or 208 positioned on the column 200. In some cases, a pocket overlapping the fastener 812 can be provided. In some cases, when such pocket is provided, any one or more of the pockets 820 or 822 can be omitted.

Providing a sterile barrier for the column 200 may be advantageous in case the central unit 400, which can be moveable, comes into contact with the column, another sterile object (such as, an instrument) comes into contact with the column, a sterile user comes into contact with the column, or the like. In some cases, the drape 800 may not be configured (such as sized and shaped) to wrap around the column 200 or a portion of the column because protecting a portion of the column 200 (for example, the portion facing the central unit 400 and/or the patient during the medical procedure) may be sufficient. In some cases, the drape 800 can be configured to be wrapped around the column 200 (or portion thereof), as described herein in connection with one or more of the drapes 600 or 700.

The drape 800 can be positioned in different orientations (or positions) to cover different portions of the column 200. With reference to FIG. 1B-1C, four fasteners 202, 204, 206, and 208 can be positioned on the column 200. The drape 800 can include three fasteners 810, 812, and 814. Because the number of fasteners of the column 200 can exceed the number of fasteners of the drape 800, the drape 800 can be positioned in different orientations to cover the column 200.

Positioning the drape in different orientations can provide a sterile barrier and/or facilitate protecting the column 200 from coming into contact with blood, fluids, tissue, or the like during the medical procedure. Orientation of the drape 800 can be selected based on the location of the column 200 relative to the patient, type of medical procedure, or the like. For example, the patient cart 104 (which may be moveable) can be positioned in different locations in the operating room. Depending on the location of the patient cart 104, a particular orientation of the drape 800 can be selected to provide a sterile barrier for a particular portion of the column 200 and/or protect the particular portion of the column 200 from being splashed, stained, or the like during the medical procedure.

Figure 6B:
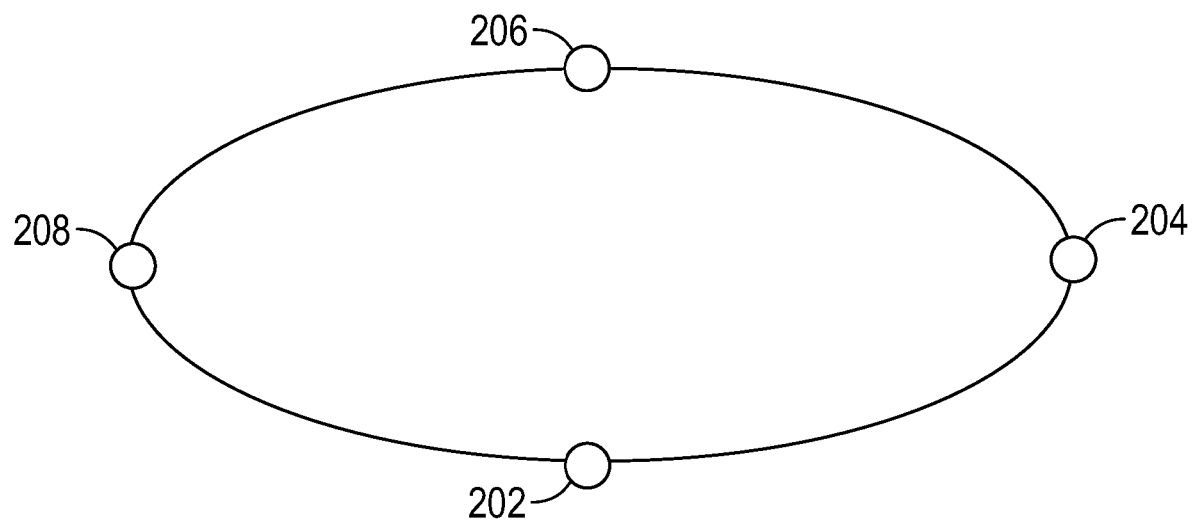
FIG. 6B illustrates various orientations of the sterile barrier of FIG. 6A.

FIG. 6B illustrates positioning of the fasteners on the column 200. For example, fastener 202 can be positioned in the front portion of the column, which can face the central unit 400 (see also FIG. 1B). The drape 800 can be positioned on, affixed to, or attached to the column 200 in one or more of the following orientations:

Front (attached to fasteners 208, 202, and 204),
Left (attached to fasteners 202, 208, and 206),
Right (attached to fasteners 202, 204, and 206), or
Back (attached to fasteners 208, 206, and 204)

Any of the fasteners 810, 812, and 814 of the drape 800 can be attached to (or coupled with) any of the fasteners 202, 204, 206, and 208 of the column 200. With reference to FIGS. 8V-8W, positioning the drape 800 on the column 200 is illustrated. As illustrated in FIG. 8V, fastener 812 of the drape 800 can be attached to any of the fasteners 202, 204, 206, and 208 of the column 200.

The drape 800 can include an additional drape portion 870 (shown, for example, in FIG. 8V). The additional drape portion 870 can be the same or similar to the additional drape portion 770 described herein.

Generally, any robotic surgery system component can include more fasteners than the sterile barrier configured to cover the component. This can facilitate positioning or attaching the sterile barrier in different orientations to cover different portions of the component. In some cases, more or less fasteners than described herein can be positioned on the any robotic surgery system component to facilitate greater or lesser number of orientations of a sterile barrier covering the component. In some cases, more or less fasteners than described herein can be positioned on any of the sterile barrier to facilitate lesser or greater number of orientations.

In some cases, a fastener of a robotic surgery system component can have at least one dimension that is different a corresponding dimension of a fastener of the sterile barrier.

Figure 11:
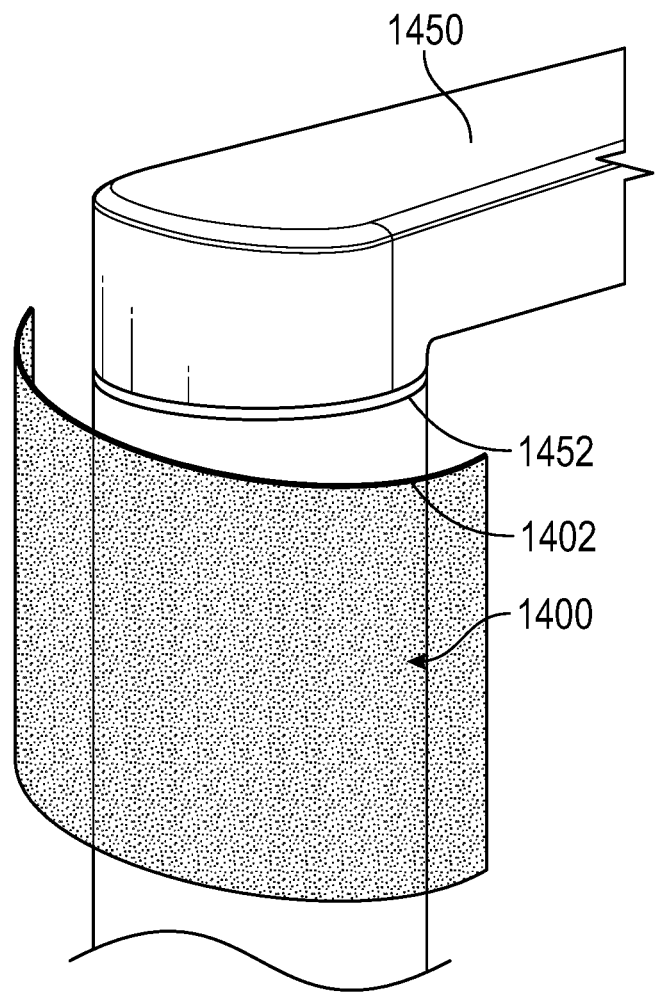
FIG. 11 illustrates positioning of a sterile barrier on a robotic surgery system component.

This can facilitate positioning or attaching the sterile barrier in different orientations to cover different portions of the component. With reference to FIG. 11, a sterile barrier 1400 can include a fastener 1402. A robotic surgery system component 1450 can include a fastener 1452. The length of the fastener 1452 can exceed or be longer than the length of the fastener 1402, permitting the sterile barrier 1400 to be positioned in various orientations to cover at least a portion of the component 1450. In some cases, the length of the fastener 1402 can be longer than the length of the fastener 1452, while permitting the same or similar purpose to be achieved. Excess portion of the sterile barrier 1400 that is not attached to the fastener 1452 can be removed or folded.

Fasteners 1402 and 1452 can include any one or more fasteners described herein, such as ferromagnetic and magnetic materials, VELCRO, adhesive, buttons, zippers, or the like. For example, fasteners 1402 and 1452 can include continuous ferromagnetic and magnetic portions. As another example, fasteners 1402 and 1452 can include discontinuous ferromagnetic and magnetic sections to facilitate positioning of the sterile barrier in a number of fixed orientations.

Labels

Figure 7A:
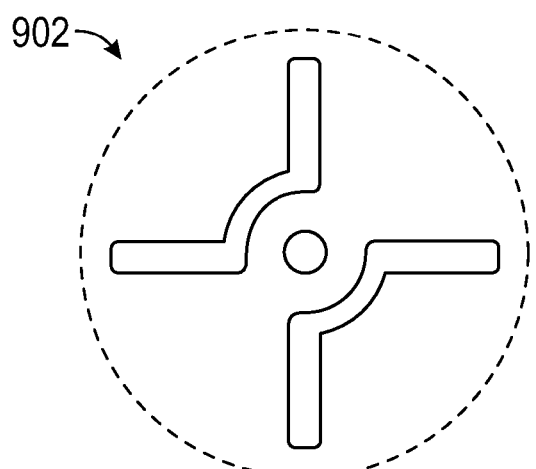
FIGS. 7A-7C illustrate labels.
Figure 7B:
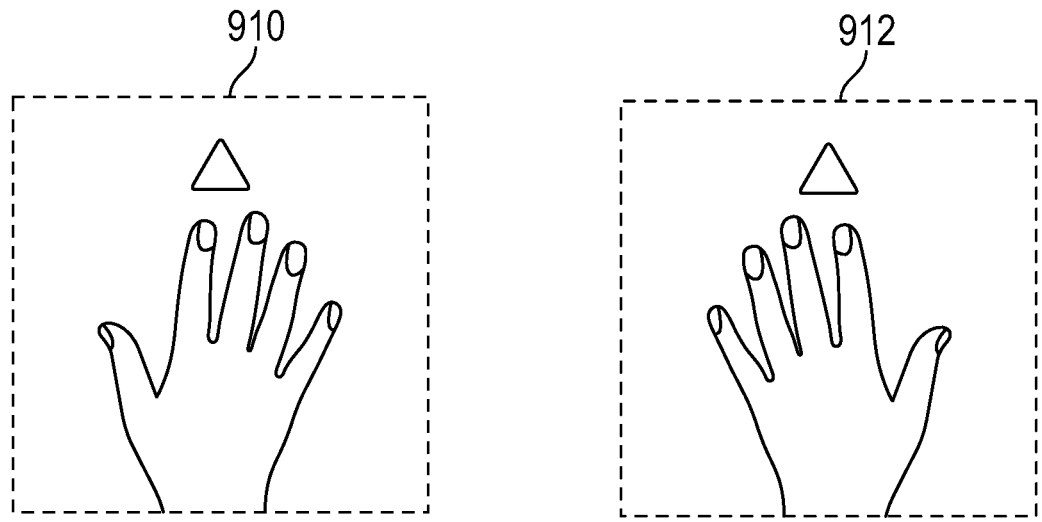
Figure 7C:
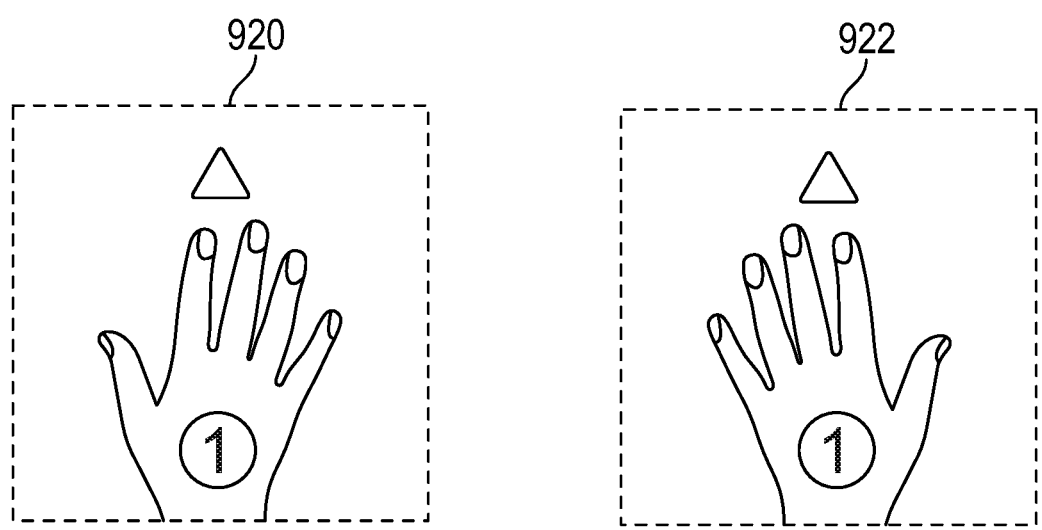

FIG. 7A illustrates a label 902 that can indicate position of any of the fasteners of the components of the robotic surgery system, such as any of the fasteners 202, 204, 206, and 208 of the column 200, 302 and 304 of the central unit 400, and 402, 404, and 406 of the arm 300. The label 902 can be attached to or affixed over or adjacent to any of the fasteners. The label 902 can match the dimensions of the fasteners. The label 902 can indicate positions of any of the fasteners of the drapes 600, 700, and 800 that are configured to be attached to any of the fasteners of the components of the robotic surgery system, such as any of the fasteners 652 and 662 of the drape 600, any of the fasteners 710, 712, and 714 of the drape 700, and any of the fasteners 810, 812, and 814 of the drape 800. The label 902 can provide a visual cue to the user where a particular fastener is located and/or what action to take (such as, affix the particular fastener to another fastener).

With reference to FIG. 7B, labels 910 and 912 can guide insertion of the right and left hand, respectively, into any of the pockets of the drapes 600, 700, and 800, as described herein. With reference to FIG. 7C, labels 920 and 922 can be similar to the labels 910 and 912, but with addition of indicia (such as "1") to indicate one or more of pairing of labels (such as, left and right hand labels) or a particular step in the process for covering a component with a sterile barrier, as described herein. The arrows in the labels 910, 912, 920, and 922 can indicate a direction for inserting the hand.

In some cases, any of the labels 910, 912, 920, and 922 can include contrast between one or more of the hand or arrow and the rest of the label. In some cases, any of the labels 920 and 922 can include contrast between one or more of the numbers or the circles outlining the numbers and the rest of the label. Contrast can include one or more of color contrast, texture contrast, difference in material, or the like.

The dashed circle in FIG. 7A can represent a portion of the component or drape on which the label 902 is positioned (such as, a fastener). The dashed rectangles in FIGS. 7A-7B can represent a portion of the drape on which any of the illustrated labels is positioned.

Covering Components of Robotic Surgery System with Sterile Barriers

FIGS. 8A-8W illustrate the steps of covering components of the robotic surgery system with one or more sterile barriers. The sequence illustrated in FIGS. 8A-8W can correspond to the sequence of the steps for covering the components of the robotic surgery system with one or more sterile barriers. In some cases, steps can be performed in different order as depicted in FIGS. 8A-8W, certain steps can be omitted or replaced, additional steps can be added, or the like.

Certain figures illustrate positioning of arms and/or hands of the user facing the robotic surgery system components and affixing various sterile barriers to the components. The orientation of the user and arms/hands in any of the illustrations can indicate whether left arm/hand or right arm/hand is being used by the user. For example, with reference to FIG. 8B, an arm/hand labeled 850 can correspond to the left arm/hand, and arm/hand labeled 852 can correspond to the right arm/hand.

The illustrations in FIGS. 8A-8W are described in the foregoing sections of the disclosure. The following sections provide summary of the illustrated steps as well as certain additional details. In some cases, the steps illustrated in FIGS. 8A-8W can be performed by a sterile nurse.

FIG. 8A illustrates attachment of the drape coupler 610 to the central unit 400 (such as, to the bottom surface of the central unit as illustrated by the arrow). FIGS. 8B-8C illustrates spreading out the drape 600 over the central unit 400 with use of the pockets 678 and 672 (such as, as shown in the direction of the arrows). FIG. 8C illustrates one or more handles 450 for moving the central unit 400. Any of the handles 450 can include a control 452, such as a button, for moving the central unit 400. FIG. 8D illustrates attaching the fasteners 662 and 652 of the drape to the fasteners 302 and 304 of the central unit 400. In this step, the user can affix the top portion of the drape 600 on or to the central unit 400. FIG. 8E illustrates wrapping the drape around, for example, the front portion of the central unit 400 (such as, in the direction of the arrow as shown) with use of the pockets 674 and 676. Also illustrated is a closure or fastener 602. With reference to FIGS. 8F-8I, one or more fasteners 602 can be configured to wrap the drape 600 around one or more protrusions of the central unit 400. The protrusions can be handles 450. The handles 450 can be configured to facilitate movement of the central unit 400 by the user. The fasteners 602 can include one or more bendable or substantially bendable materials, such as metal (for instance, metal wire), plastic, or the like. The one or more materials of the fasteners 602 can be resilient or substantially resilient, ductile or substantially ductile, and/or elastic or substantially elastic. The fasteners 602 can be returned to the original (such as, unbent or substantially unbent) shape by the user. The fasteners 602 can be further bent to another desired shape. The fasteners 602 can be deformable without breaking, fracture, or the like. The fasteners 602 can be used to tighten the drape 600 around portions (such as, a handle 450) of the central unit 400.

FIGS. 8E-8F illustrate wrapping the drape 600 around, for example, the front portion of the central unit 400. This can be accomplished by attaching the fastener 656 to the second fastener 652, and attaching the fastener 658 to the second fastener 662. The user can position the user's hands in the pockets 674 and 676 as shown. FIG. 8G illustrates tightening the drape 600 around, for example, the rear portion of the central unit 400 (such as, in the direction shown by the arrows) by attaching the fasteners 654 and 660 to each other.

FIG. 8H illustrates the drape 600 wrapped around the central unit 400. As shown, the drape 600 can cover a portion of the arm 300, such as the bottom portion of the arm. The arrow in FIG. 8H can illustrate the location for positioning the sterile drivers 232 (for example, on the interface 500 of the central unit 400).

FIG. 8I illustrates moving the central unit 400 (such as, in the direction of the arrows) for positioning one or more sterile adapters 680. The central unit 400 can be rotated. FIG. 8J illustrates positioning of the one or more sterile adapters 680, for example, as illustrated by the arrow. The central unit 400 can be moved (as illustrated in FIG. 8I) and/or tilted (as illustrated in FIG. 8J) by activating one or more controls 452 positioned on the one or more handles 450. For example, a button 452 (or any two or more buttons 452) can be pressed to move and/or tilt the central unit 400. FIGS. 8K-8M illustrate, in greater details, attaching the one or more sterile adapters 680 to the one or more instrument interfaces 420.

As described herein, the actuators 422 can be positioned in a default alignment to facilitate engagement with the surgical instrument actuators 322 when the surgical instrument is loaded. The surgical instrument actuators 322 can also be positioned in a default alignment. As illustrated in FIG. 8L, the actuators 422 can be centrally aligned in the default alignment. The surgical instrument actuators 322 can also be centrally aligned in the default alignment. The actuator covers 622 of the adapter 680 can be maintained or fixed in a default alignment, which can match the default alignment of the actuators 422 (and/or the instrument actuators 322). As illustrated in FIG. 8N, a retainer 698 can maintain the actuator covers 622 in the default alignment. The retainer 698 can surround the actuators covers 622 as shown. The retainer 698 can be removable. The retainer 698 can be attached to the surface of the adapter configured to face away from the instrument interface 420. After the adapter 680 is attached to the instrument interface 420 (and the actuator covers 622 are engaged with the actuators 422), the retainer can be removed. In some cases, the retainer 698 can include adhesive tape attached to one or more surfaces of the adapter 680 surrounding the actuator covers as shown. The adhesive tape can be removed after installation of the adapter 680.

In some cases, the actuator covers 622 can be maintained in the default alignment by being connected together with one or more strips. The strips can include material that can be removed easily, such as plastic. For example, adjacent actuator covers can be connected together with plastic strips or pieces. When the actuator covers 622 are moved due to movement of the actuators 422, the plastic pieces would break off. The actuator covers 622 can include groves or channels for attaching the plastic pieces. The channels can be formed during, for example, molding of the actuator covers. In some cases, a removable cover can be used to maintain default alignment of the actuator covers. After the adapter 680 is attached to the instrument interface, the cover can be removed to permit independent movement of the actuator covers 622.

FIGS. 8O-8U illustrate covering the arm 300 with the drape 700. FIGS. 8O-8P illustrate attaching the fasteners 710, 712, and 714 to the fasteners 402, 404, and 406 of the arm 300 with use of the pockets 720 and 722 (for example, in the direction of the arrow in FIG. 8O). In this step, the user can affix the top portion of the drape 700 on or to the arm 300. FIG. 8Q illustrates detaching the flap 760 from the drape 700, such as, in the direction of the arrow. FIG. 8R illustrates wrapping the flap 760 (and in some cases other portions of the drape) around the arm 300 with use of the pocket 724, such as, in the direction of the arrow. For example, the left hand (or portion thereof) of the user can be positioned in the pocket 724. The user can use the other hand (such as, the right hand) to assist with the wrapping of the drape 700. A pocket for positioning the other hand may not be needed since the risk the other hand of coming into contact with a non-sterile surface may be low or not present because any of the flaps 760 or 762 is unlikely to have come into contact with a non-sterile surface.

FIGS. 8S-8T illustrate wrapping the drape around the arm 300. FIG. 8S illustrates the flap 760 (and in some cases other portions of the drape) being wrapped around the arm 300, such as, in the direction illustrated by the arrow. The user's hand can remain in the pocket 724. The other flap 762 is illustrated as being wrapped around a portion of the drape (such as, the flap 760), such as, in the direction shown by the arrow in FIG. 8T. The user can wrap the flap 762 with the other hand not positioned in the pocket 724 (such as, the right hand). FIG. 8T illustrates attaching fasteners 740 and 742 to each other to secure (such as, tighten) at least the top portion of the drape 700. As described herein, the middle portion of the drape can be similarly secured by attaching the fasteners 748 and 750. FIG. 8U illustrates securing (for example, tightening) the bottom portion of the drape 700 by attaching the fasteners 744 and 746 to each other with the use of the pocket 726. The drape 700 can be tightened in the direction of the illustrated arrows. The bottom portion of the drape 700 can partially overlap the top portion of the drape 600, as described herein. FIGS. 8Q-8T illustrate the additional drape portion 770, which may be optional.

FIGS. 8V-8W illustrate covering the column 200 with the drape 800. The fasteners 810, 812, and 814 are attached (such as, in the direction of the illustrated arrows) to three of the four fasteners 202, 204, 206, and 208 of the column 200 with use of the pockets 820 and 822 to position the drape 800 in the desired orientation. FIGS. 8V-8W illustrate the additional drape portion 870, which may be optional.

In some cases, sterile barrier for the central unit 400 can be installed first. Installation of the sterile barrier for the central unit 400 can be performed in the following order: sterile barrier 650, followed by one or more sterile drivers 232, and followed by one or more sterile adapters 680. Sterile barrier 700 for the arm 300 can be installed next. Sterile barrier 800 for the column 200 can be installed last. In some cases, steps can be performed in different order, certain steps can be omitted or replaced, additional steps can be added, or the like.

Sterile barriers described herein can be removable. The user, such as, the sterile nurse (and/or non-sterile nurse), can remove the sterile barriers. For example, the user can follow reverse steps for removing the sterile barriers.

Sterile Barrier Fasteners for Robotic Surgery System Components

As described herein, the components of the robotic surgery system can include fasteners for attaching fasteners of the sterile barriers. For example, the column 200 can include fasteners 202, 204, 206, and 208, the central unit 300 can include fasteners 302 and 304 of the central unit, and the arm can include fasteners 402, 404, and 406. The fasteners can be positioned on the external surfaces of the components. The fasteners can be configured to support the sterile barriers. The fasteners can be configured to withstand the sheer forces that may be applied to the sterile barriers during the medical procedure while maintaining secure attachment.

In some cases, any of the fasteners can be magnetic fasteners. The magnetic fasteners can be configured to provide secure support for the sterile barriers during the medical procedure. One or more magnetic materials of a fastener can be selected to have sufficient strength to support the sterile barrier attached to the component. Alternatively or additionally, a configuration of the fastener can be important for providing secure support for the sterile barrier.

Figure 9:
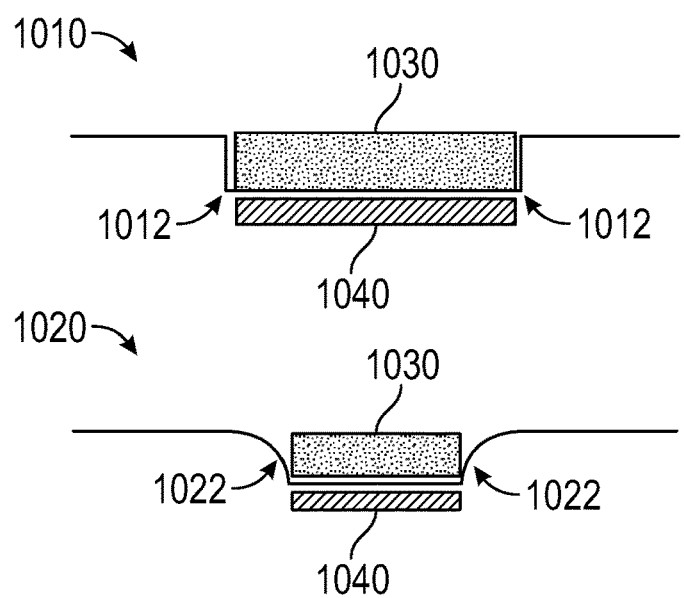
FIG. 9 illustrates fasteners of the robotic surgery system.

FIG. 9 illustrates configurations 1010 and 1020 of a fastener. The fastener can include a recess defined by a bottom surface and side surfaces or walls 1012 in the configuration 1010 and side surfaces or walls 1022 in the configuration 1020. Corresponding fastener 1030 of the sterile barrier can be at least partially received or positioned in the recess. This can facilitate secure attachment.

Magnetic material 1040 (such as, a permanent magnet) can be positioned in the recess (such as, at the bottom of the recess) in the configurations 1010 and 1020. The side walls 1012 in the configuration 1010 can form a right (or substantially right angle) with the bottom of the recess. The side walls 1012 in the configuration 1010 can form a right (or substantially right) angle with the exterior surface of the robotic surgery system component. In this configuration, the fastener 1030 of a sterile barrier may be more securely attached to the fastener of the robotic surgery component due to, for example, presence in the recess of one or more edges, including sharp edges (such as, edges formed at a right angle or substantially right angle). This can facilitate secure attachment by preventing an unintended dislodging or disengagement of the fastener 1030, while facilitating efficient disengagement by the user when the sterile barrier is being repositioned or removed.

The side walls 1022 in the configuration 1020 can be curved as illustrated. The transitions made by the side walls 1022 can be smooth. The angle formed by the side walls 1022 with the bottom of the recess (and/or the exterior surface of the robotic surgery system component) can be more acute than a right (or substantially right) angle, which may cause the fastener 1030 to dislodge or disengage more easily than in the configuration 1010. In some cases, the side walls in the configuration 1020 can be straight (rather than curved), but form an acute angle with the bottom of the recess (and/or the exterior surface of the robotic surgery system component).

Detection of Positioning and Orientation of Sterile Barriers

The robotic surgery system can be configured to detect one or more of positioning and orientation of the sterile barriers. This can be advantageous for verifying that the robotic surgery system is properly covered prior to the start of the medical procedure. In some cases, the electronic circuitry 114 alone or in combination with the electronic circuitry 118 can perform the detection of one or more of the positioning or orientation. Indication corresponding to the detection can be provided to the user visually (such as, via any of the displays 120 or 123), audibly, tactilely, and/or the like.

One or more detectors or sensors can be used to facilitate the detection. The sensors can include proximity sensors, such as one or more of capacitive sensors, photoelectric sensors, inductive sensors (which may be used for detecting a metal object, such as a fastener or metal tracing, of the sterile barrier), RFID detectors, or the like. The one or more sensors can be coupled to the electronic circuitry 118 and/or 114. A sensor can detect whether a sterile barrier (or portion of the sterile barrier) is in contact with a fastener of any of the components of the robotic surgery system or present within a threshold distance of the sensor. In some cases, the threshold distance may be a few millimeters, a few centimeters, or a few inches. In some cases, the sensor can detect contact of the sterile barrier (or portion thereof) with a fastener. For example, the sensor can detect positioning of ferromagnetic material, such as metal washer, metal trace, or the like of the sterile barrier on the fastener of the robotic surgery system. The electronic circuitry 118 and/or 114 can use data provided by the one or more proximity sensors to determine one or more of positioning or orientation of the sterile barrier.

One or more sensors can be positioned on the one or more robotic surgery system components. For example, one or more sensors can be positioned in or adjacent to the recesses described in connection with FIGS. 9A-9B. One or more sensors can be calibrated to perform the detection. For example, a sensor can be calibrated to perform the detection when the sterile barrier is attached to (such as, makes contact with) or positioned within threshold distance of one or more fasteners of the components of robotic surgery system, but not when the sterile barrier is positioned at a distance farther than the threshold distance.

In some cases, orientation of the sterile barrier can be detected based on a determination of which of the one or more fasteners of the components of the robotic surgery system the sterile barrier is attached to. For example, as described herein, the sterile drape 800 can be attached (or positioned) in multiple orientations. Determination that the drape fasteners are attached to (or coupled with) a set of the fasteners 202, 204, 206, and 208 of the column 200 can be used to indicate that the drape 800 is positioned. Depending on the determination of which of the fasteners 202, 204, 206, and 208 the drape fasteners are attached to, orientation of the drape can be determined. For instance, determination of attachment of the drape fasteners to the fasteners 208, 202, and 204 of the column 200 can indicate front orientation of the drape, as described herein. As another example, one or more RFID tags of the sterile barrier can be detected by one or more RFID detectors of the robotic surgery system. Different portions of the sterile barrier can include different RFID tags (for example, different tags can transmit different unique identifiers). Detection of a particular RFID tag from a set of different RFID tag by an RFID tag detector can indicate positioning and orientation of the sterile barrier.

Based on the detection of one or more of positioning and orientation of a sterile barrier, a determination of whether the sterile barrier is correctly attached can be made. For example, if the correct orientation of the sterile drape 800 is the front orientation, determination that the drape 800 is attached in the front orientation can indicate that the attachment of the drape is correct, or otherwise in the desired orientation. Indication of whether the attachment is correct or not can be provided to the user visually (such as, via any of the displays 120 or 123), audibly, tactilely, and/or the like.

Sterile Barrier Kit

Figure 10:
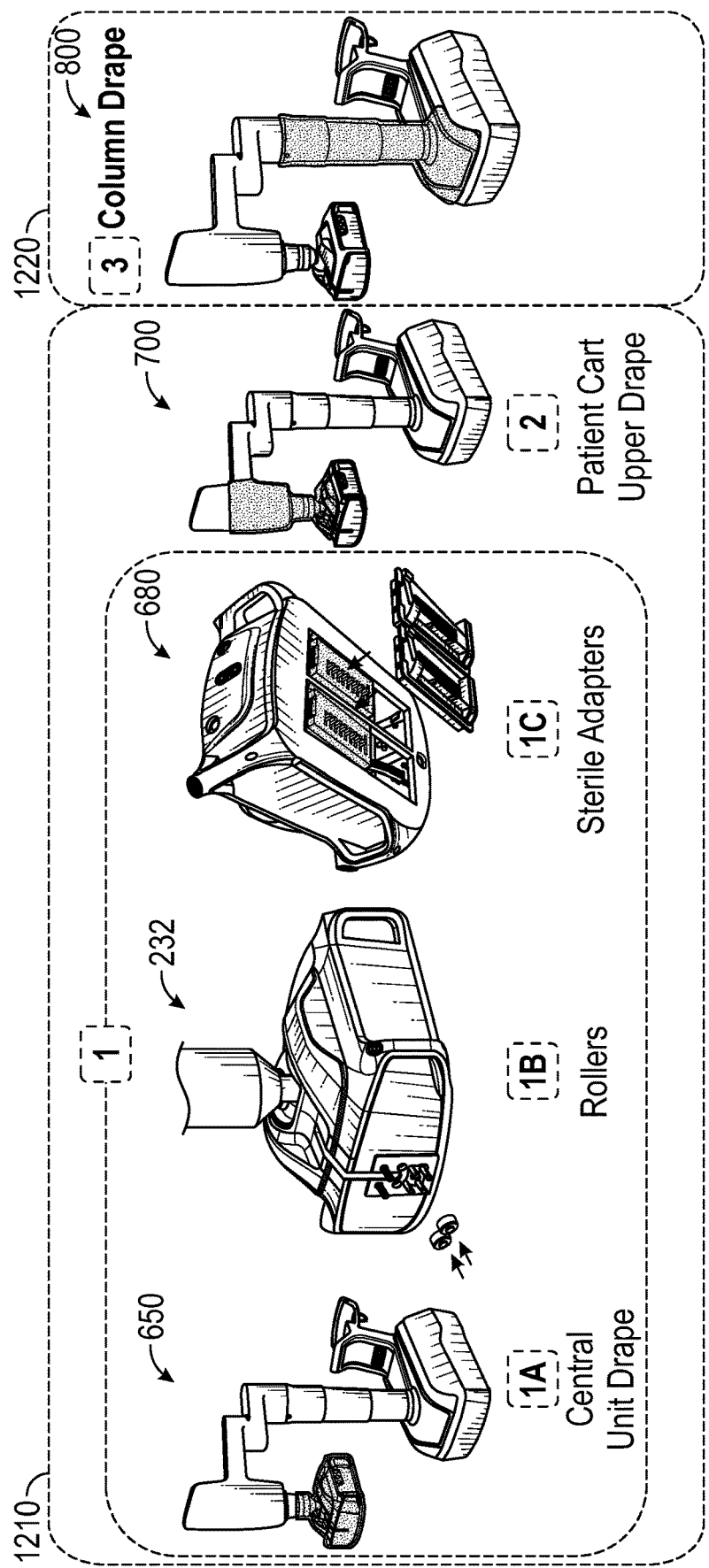
FIG. 10 illustrates sterile barrier kits.

The sterile barriers described herein can be packaged in sterile packaging and provided as a one or more kits. The packaging can include one or more bags, pouches, boxes, trays, or the like. FIG. 10 illustrates a kit 1210, which can include the sterile barrier 650, one or more sterile drivers 232, and one or more sterile adapters 680 for the central unit 400. The kit 1210 can include the sterile barrier 700 for the arm 300. A kit 1220 can include the sterile barrier 700 for the column 200. In some cases, kits 1210 and 1220 can be combined into a single kit. Each sterile barrier in any of the kits can be sterile. Each sterile barrier in any of the kits can be packaged into sterile packaging. The illustrations shown in FIG. 10 can correspond to labels included in or on the packaging for the sterile barriers.

In some cases, the numbering 1 (1A, 1B, 1C), 2, and 3 can indicate the order of steps for covering the robotic surgery system with sterile barriers, as described herein in connection with FIGS. 8A-8W. One or more numbers can be omitted in some cases, different numbers can be used, the numbers can be in different order, or the like. The illustrated text can be fully or partially omitted, different text can be used, or the like.

Other Variations

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical devices and medical procedures in general, among other uses.

In some cases, one or more surfaces of one or more components of the robotic surgery system may be sterilized (for example, one or more external surfaces and/or other parts can be sterilized), and any of the sterile barriers described herein may not be used. In some cases, magnetic material can be included in the fasteners of the sterile barriers and ferromagnetic material can be included in the fasteners of the one or more components of the robotic surgery system. In some cases, in addition to or instead of using magnetic force(s) for attachment, one or more fasteners can include adhesive, buttons, VELCRO, zippers, or the like. Although certain sterile barriers are described as drapes, barriers other than drapes can be used. Any of the fasteners disclosed herein can be referred to as a closure, attachment, or the like. In some cases, one or more pockets described herein can be omitted. The user may be able to grip a particular fastener through the sterile surface of the drape, such as the outer facing surface. Although certain components are illustrated as being circular, the components can have any shape, such as square, rectangular, or the like.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B."

Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A sterile barrier system for a robotic surgery apparatus, the system comprising:
    a drape coupler comprising:
        an external surface configured to face a first surface of a first portion of the robotic surgery apparatus,
        at least one drape coupler fastener positioned at least partially on the external surface of the drape coupler and configured to removably attach the drape coupler to the first surface of the first portion of the robotic surgery apparatus, the drape coupler configured to at least partially cover the first surface, and
        an opening configured to expose a surgical instrument interface of the first portion of the robotic surgery apparatus, the surgical instrument interface configured to cause actuation of a surgical instrument mounted on the surgical instrument interface;
    a drape made of a flexible material and coupled to the drape coupler, the drape configured to wrap around a second surface of the first portion of the robotic surgery apparatus, the second surface different from the first surface; and
    a sterile adapter configured to be received at the opening and to be removably attached to the surgical instrument interface, the sterile adapter configured to receive and support the surgical instrument and provide a sterile barrier between the surgical instrument interface and the surgical instrument, the sterile adapter including a plurality of actuator covers configured to couple with a plurality of instrument actuators positioned on the surgical instrument interface.

2. The system of claim 1, wherein:
    the first portion of the robotic surgery apparatus comprises a manipulator unit;
    the first surface comprises a manipulating surface of the manipulator unit;
    the at least one drape coupler fastener is configured to removably attach the drape coupler to the manipulating surface of the manipulator unit;
    the second surface comprises at least one side surface of the manipulator unit; and
    the drape is configured to enclose the at least one side surface of the manipulator unit.

3. The system of claim 1, wherein the at least one drape coupler fastener comprises ferromagnetic material configured to be attached to a magnet positioned on the first surface.

4. The system of claim 1, wherein the at least one drape coupler fastener comprises a plurality of fasteners comprising ferromagnetic material and configured to be attached to a plurality of magnets positioned on the first surface.

5. The system of claim 1, wherein the drape is coupled to the drape coupler along a perimeter of the drape coupler.

6. The system of claim 1, wherein the drape coupler further comprises at least one removable protector configured to cover the opening of the drape coupler.

7. The system of claim 1, wherein the drape coupler further comprises at least one region made at least partially of a flexible material, the at least one region positioned adjacent to the opening and configured to collapse and expand.

8. The system of claim 7, wherein the at least one region comprises first and second regions, the first region positioned adjacent to a first side of the opening and the second region positioned adjacent to a second side of the opening opposite the first side, the first and second regions configured to collapse and expand in response to movement of the opening.

9. The system of claim 7, wherein at least one region comprises an insert made at least partially of material that is more rigid than the material of the at least one region, the insert configured to cause the flexible material of the at least one region to fold when the at least one region is collapsed.

10. The system of claim 9, wherein the insert includes at least one tapered edge.

11. The system of claim 1, wherein the drape comprises at least one drape fastener configured to removably attach the drape to a third surface of the first portion of the robotic surgery apparatus.

12. The system of claim 11, wherein the at least one drape fastener comprises a bendable material and is configured to be wrapped around at least one protrusion on the third surface.

13. The system of claim 1, wherein the drape comprises a first region including a first drape fastener and a second region including a second drape fastener, the first region configured to be positioned over the second region and fastened to the second region by attachment of the first drape fastener to the second drape fastener.

14. The system of claim 1, wherein the drape comprises a cover made of a material more rigid than the flexible material of the drape, the cover configured to enclose a pin positioned on a third surface of the first portion of the robotic surgery apparatus and configured to be inserted into an opening of at least one of a surgical instrument insertion device or a camera insertion device of the robotic surgery apparatus, the cover configured to provide a sterile barrier between the pin and the opening of at least one of the surgical instrument insertion device or the camera insertion device of the robotic surgery apparatus.

15. The system of claim 1, wherein the drape comprises an insert made of a material more rigid than the flexible material of the drape, the insert configured to be positioned in an opening in the first portion of the robotic surgery apparatus that receives a portion of an endoscopic camera of the robotic surgery apparatus, the insert configured to provide a sterile barrier between the endoscopic camera and the first portion.

16. The system of claim 15, wherein the insert includes first and second elongated side surfaces connected at one end and not connected at an opposite end to form a slot, the slot configured to be inserted into the opening of the first portion and to receive the endoscopic camera.

17. The system of claim 1, wherein the drape comprises a first pocket configured to receive and at least partially enclose a first hand of a user, the first pocket configured to facilitate positioning of the drape on the first portion of the robotic surgery apparatus.

18. The system of claim 17, wherein the drape further comprises a second pocket configured to receive and at least partially enclose a second hand of a user, the second pocket configured to facilitate positioning of the drape on the first portion of the robotic surgery apparatus.

19. The system of claim 18, wherein the first and second pockets are positioned to allow a user to lift the drape away from the second surface while maintaining a sterile barrier for the first portion of the robotic surgery apparatus.

20. The system of claim 1, wherein the drape coupler is made from material that is more rigid that the flexible material of the drape.

21. The system of claim 1, wherein the actuator covers are configured to be positioned in a first position prior to attaching the sterile adapter to the surgical instrument interface, the actuator covers being aligned in the first position.

22. The system of claim 21, wherein the sterile adapter includes a retainer surrounding the actuator covers, the retainer being configured to maintain positioning of the actuator covers in the first position.

23. The system of claim 22, wherein the retainer is removable to permit at least one of the actuator covers to be moved to a position different than the first position.

24. The system of claim 21, wherein the actuator covers are centrally aligned in the first position.

25. The system of claim 1, wherein the actuator covers are configured to move in at least one direction to facilitate at least one of movement or articulation of the surgical instrument supported by the sterile adapter.

* * * * *